US009963474B2

(12) United States Patent
Murphy et al.

(10) Patent No.: US 9,963,474 B2
(45) Date of Patent: May 8, 2018

(54) MITOCHONDRIA-TARGETED DICARBONYL SEQUESTERING COMPOUNDS

(71) Applicant: MEDICAL RESEARCH COUNCIL, Swindon Wiltshire (GB)

(72) Inventors: Michael Patrick Murphy, Newmarket Cambridgeshire (GB); Robin Andrew James Smith, Dunedin (NZ); Richard Charles Hartley, Glasgow (GB)

(73) Assignee: Medical Research Council, Swindon Wiltshire (GB)

( * ) Notice: Subject to any disclaimer, the term of this patent is extended or adjusted under 35 U.S.C. 154(b) by 0 days. days.

(21) Appl. No.: 15/037,941

(22) PCT Filed: Nov. 21, 2014

(86) PCT No.: PCT/EP2014/075323
§ 371 (c)(1),
(2) Date: May 19, 2016

(87) PCT Pub. No.: WO2015/075200
PCT Pub. Date: May 28, 2015

(65) Prior Publication Data

US 2016/0289252 A1 Oct. 6, 2016

(30) Foreign Application Priority Data

Nov. 22, 2013 (GB) .................................. 1320636.2

(51) Int. Cl.
*C07F 9/54* (2006.01)
*A01N 1/02* (2006.01)
*G01N 33/58* (2006.01)

(52) U.S. Cl.
CPC .......... *C07F 9/5442* (2013.01); *A01N 1/0226* (2013.01); *G01N 33/58* (2013.01)

(58) Field of Classification Search
None
See application file for complete search history.

(56) References Cited

U.S. PATENT DOCUMENTS 6,419,711 B1 7/2002 Genet et al.
7,956,193 B2 * 6/2011 Zhang ................. C07D 275/02 540/145
2010/0063277 A1 3/2010 Zhang et al.
2015/0202135 A1 * 7/2015 Fadli ................... A61K 8/4913 8/416

FOREIGN PATENT DOCUMENTS

CN 102617467 8/2012
GB 926998 * 5/1963

OTHER PUBLICATIONS

Zhang, Kun. Novel aromatic polyimides with pendent triphenylamine units: Synthesis, photophysical, electrochromic properties. Journal of Electroanalytical Chemistry. 682 (2012) 101-109.*

Boone, Pamela, et al. “Pathological Significance of Mitochondrial Glycation” International Journal of Cell Biology, vol. 2012, Article ID 843505; pp. 1-14.

Boone, Pamela, et al. “A mitochondria-targeted mass spectrometry probe to detect glyoxals: implications for diabetes” Free Radical Biology and Medicine 67 (2014); pp. 437-450.

Duval, Eric “International Search Report and Written Opinion of the International Searching Authority—PCT application No. PCT/EP2014/075323” European Patent Office; dated Mar. 13, 2015; pp. 1-13.

Mamidi, Narsimha, et al. “Zn(OTF)2-Promoted Chemoselective Esterification of Hydroxyl Group Bearing Carboxylic Acids” J. Org. Chem. (2013) pp. 2386-2396.

Robinson, K.M. et al. “Selective Fluorescent Imaging of Superoxide in Vivo using Ethidium-based Probes,” Proceedings of the National Academy of Sciences, vol. 103, No. 41, Oct. 10, 2006, pp. 15038-15043.

* cited by examiner

*Primary Examiner* — Samantha L Shterengarts
(74) *Attorney, Agent, or Firm* — Thomas G. Peterson; Bradley Arant Boult Cummings LLP

(57) ABSTRACT

The invention relates to compounds having Formula (1): A-L-B or pharmaceutically acceptable salts thereof, wherein: A is a dicarbonyl sequestering moiety comprising a substituted aryl group or a substituted heteroaryl group; L is an optional linker moiety; and B is a mitochondrial targeting moiety. The invention also relates to pharmaceutical compositions containing such compounds and salts, and to the use of such compounds and salts for treating diabetes, preferably hyperglycemic diabetes. A mass spectrometry probe and to a method of labelling a biological molecule 1 for mass spectrometry detection are also described.

16 Claims, 18 Drawing Sheets

MITOCHONDRIA-TARGETED DICARBONYL SEQUESTERING COMPOUNDS

CROSS-REFERENCE TO RELATED APPLICATIONS

This application is a national stage under 35 U.S.C. 371 of International Application PCT/EP2014/075323, filed on Nov. 21, 2014 (currently published). International Application PCT/EP2014/075323 cites the priority of British Patent Application No. 1320636.2, filed Nov. 22, 2013 (expired).

FIELD OF THE INVENTION

The invention relates to compounds and pharmaceutically acceptable salts thereof comprising a dicarbonyl sequestering moiety; an optional linker moiety; and a mitochondrial targeting moiety. The invention also relates to pharmaceutical compositions containing such compounds and salts, and to the use of such compounds and salts for treating diabetes, preferably hyperglycemic diabetes. The invention also relates to the provision of a mass spectrometry probe and to a method of labelling a biological molecule for mass spectrometry detection.

BACKGROUND

Hyperglycaemia is a damaging medical condition. Hyperglycaemia wreaks its effects via inappropriate glycation of molecules within cells. This glycation occurs following generation of reactive 1,2-dicarbonyls such as glyoxal and methylglyoxal. These reactive species modify molecules in the cell and cause negative pathology.

Glycation, the non-enzymatic formation of sugar-protein and sugar-nucleotide adducts, plays a major role in disrupting cell function and causing tissue damage in a range of pathologies such as diabetes, aging and neurodegeneration [1-3]. Glycation increases in response to the elevation of glucose that occurs in unregulated diabetes and is a major cause of diabetic complications [4, 5]. Within the cell excessive glucose can lead to molecular damage through the formation of 1,2-dicarbonyl compounds such as methylglyoxal from the triose phosphate intermediates of glycolysis [1, 6] or from the metabolism of acetone generated during ketosis [7]. These reactive 1,2-dicarbonyls often exist in modified chemical forms in situ including reversible hemiacetals, hemithioacetals and hemiaminals with small biomolecules and with reactive moieties on proteins and nucleic acids [8, 9]. In addition they can react directly with free amine functions on proteins and nucleic acids, thereby generating substantial permanent modifications such as arginine-derived hydroimidazolones and lysine cross-links on proteins [10], and guanine-derived imidazopurinones on DNA [11]. Such modifications are thought to result in biochemical dysfunction by altering protein structure and activity, and by inducing genomic mutations [2]. These markers of glycation damage are elevated in many clinical samples from diabetic patients and also in animal models of diabetes and aging [2,4,9,12,13], consistent with a contribution from these reactions to cell damage and pathology. An important role for methylglyoxal and glyoxal in pathology is further supported by the existence of the glyoxalase enzyme system, which specifically degrades these two dicarbonyls [14]. Loss of the glyoxalase degradation pathway renders organisms more susceptible to glycation and subsequent damage while its over-expression increases lifespan in *Caenorhabditis elegans* [15]. Thus dicarbonyl-associated glycation of proteins and nucleic acids is a significant contributing factor in a range of pathologies, particularly those associated with diabetes or aging.

In hyperglycaemia, there is considerable evidence for mitochondrial damage and elevated oxidative stress that contributes to pathology, and this has been in part ascribed to mitochondrial glycation due to methylglyoxal and glyoxal [16-21]. Furthermore these reactive dicarbonyls disrupt mitochondrial function in vitro [22-24]. Therefore, understanding the contribution from glycation damage by reactive dicarbonyls to mitochondrial dysfunction is important for analyzing and understanding the pathology associated with hyperglycaemia. However, the mechanistic details are uncertain, and it has proven difficult to specifically evaluate the importance of these processes. This is in part due to the uncertainties related to the distribution of methylglyoxal and glyoxal between the cytosol and mitochondria. In known approaches to combating the effects of hyperglycaemia, it has been attempted to use reactive guanidine groups. This forms a generalised "mopping" approach. The guanidine groups react with glyoxal/methylglyoxal groups. However, this guanidine approach is entirely untargeted. This is a drawback in the art.

SUMMARY

In addressing problem(s) associated with the prior art, the solution provided by the inventors includes compounds of the invention which specifically target molecular groups capable of sequestering the dicarbonyls that are found within mitochondria under conditions of hyperglycaemia.

These compounds couple a targeting moiety to a sequestering moiety so that the compounds preferentially accumulate in the mitochondria, where they are maximally effective in reducing and/or preventing the damage caused by the reactive dicarbonyls. Optionally, the sequestering moiety may be attached to the targeting moiety via a linker moiety. It should be noted that the approach of sequestering the reactive groups within mitochondria is new. This approach has not been contemplated in any known treatment. It should be noted that the approach underlying the invention of sequestering the reactive groups within mitochondria themselves is a departure from known techniques. These and other benefits flow from the invention as explained below.

Thus, in a broad aspect the invention relates to a compound of Formula 1:

A-L-B    Formula 1 or a pharmaceutically acceptable salt thereof, wherein:

A is a dicarbonyl sequestering moiety comprising a substituted aryl group or a substituted heteroaryl group;

L is a linker moiety; and

B is a mitochondrial targeting moiety;

wherein the substituted aryl group, or the substituted heteroaryl group comprises two or more substituent groups independently selected from —OH, —$OR_1$, —$NH_2$, —$NHR_1$, —$NR_1R_1$, —$^{1}X$—$NH_2$, —$^{1}X$—$NHR_1$, —O—$NH_2$, —O—$NHR_1$, —$^{1}X$—O—$NH_2$, —$^{1}X$—O—$NHR_1$, —NR'—NHR', —$^{1}X$—NR'—NHR', —$NHCOR_1$ and —O—C(O)—$R_1$; and wherein the substituted aryl group, or the substituted heteroaryl group may optionally comprise one or more optional substituent groups selected from —$C_{1-6}$ alkyl, —$C_{2-6}$ alkenyl, —$C_{2-6}$ alkynyl, -halogen, —$^{1}X$—OH, —$^{1}X$—O—$R_1$, —$CO_2H$, —$^{1}X$—$CO_2H$, —$CO_2R_1$, —$^{1}X$—$CO_2R_1$, —$^{1}X$—O—C(O)—$R_1$, —CH(OH)—C (O)—$R_1$, —$^1X$—$NR_1R_1$, —$^1X$—CH(OH)—C(O)—$R_1$, —CHO, —C(O)—$R_1$, —C(O)$NH_2$, —C(O)$NHR_1$, —$SO_2NH_2$ and —$SO_2NHR_1$; and wherein each $R_1$ is independently selected from —$C_{1-6}$ alkyl, —$C_{2-6}$ alkenyl, —$C_{2-6}$ alkynyl, and Formula 2

Formula 2

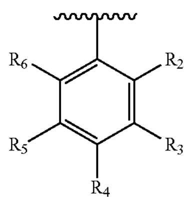

wherein each group $R_2$-$R_6$ is independently selected from —H, —$C_{1-6}$ alkyl, —$C_{2-6}$ alkenyl, —$C_{2-6}$ alkynyl, -halogen, —OH, —$^1X$—OH, —O—$C_{1-6}$ alkyl, —$^1X$—O—$C_{1-6}$ alkyl, —NR'R', —$^1X$—NR'R', —$^1X$—NH—$C_{1-6}$ alkyl, —O—$NH_2$, —O—NH—$C_{1-6}$ alkyl, —$^1X$—O—$NH_2$, —$^1X$—O—NH—$C_{1-6}$ alkyl, —NR'—NHR', —$^1X$—NR'—NHR', —NHC(O)—$C_{1-6}$ alkyl, —O—C(O)—$C_{1-6}$ alkyl, —$CO_2H$, —$^1X$—$CO_2H$, —$CO_2C_{1-6}$ alkyl, —$^1X$—$CO_2C_{1-6}$ alkyl, —$^1X$—O—C(O)—$C_{1-6}$ alkyl, —CH(OH)—C(O)—$C_{1-6}$ alkyl, —CHO, —C(O)—$C_{1-6}$ alkyl, —$^1X$—CH(OH)—C(O)—$C_{1-6}$ alkyl, —C(O)$NH_2$, —C(O)NH $C_{1-6}$ alkyl, —$SO_2NH_2$ and —$SO_2$NH $C_{1-6}$ alkyl;

each R' is independently selected from —H and —$C_{1-6}$ alkyl; and each $^1X$ is independently selected from $C_{1-6}$ alkylene, $C_{2-6}$ alkenylene and $C_{2-6}$ alkynylene.

In one aspect the invention provides a pharmaceutical composition which comprises: a compound of Formula 1, as defined above, or a pharmaceutically acceptable salt thereof, and a pharmaceutically acceptable excipient, carrier or diluent.

A further aspect of the invention provides a compound of Formula 1, as defined above, or a pharmaceutically acceptable salt thereof, for use as a medicament.

A further aspect of the invention provides a compound of Formula 1, as defined above, or a pharmaceutically acceptable salt thereof, for use in the treatment of diabetes, preferably hyperglycemic diabetes.

A further aspect of the invention provides a compound of Formula 1, as defined above, or a pharmaceutically acceptable salt thereof, for the preparation of a medicament for the treatment of diabetes, preferably hyperglycemic diabetes.

A further aspect of the invention provides a method of treating a disease or condition in a subject, the method comprising administering to the subject an effective amount of a compound of Formula 1, as defined above, or a pharmaceutically acceptable salt thereof, wherein the disease or condition is diabetes, preferably hyperglycemic diabetes.

A further aspect of the invention provides a compound of formula 1, as defined above, or a pharmaceutically acceptable salt thereof, for use in the preservation of organ and tissue for surgical transplants.

A further aspect of the invention provides a compound of formula 1, as defined above, or a pharmaceutically acceptable salt thereof, for use in the storage of blood.

A further aspect of the invention provides a compound of formula 1, as defined above, or a pharmaceutically acceptable salt thereof, for use in the prevention or treatment of hyperglycaemia.

A further aspect of the invention provides a compound of Formula 1, as defined above, or a pharmaceutically acceptable salt thereof, for use as a mass spectrometry probe.

A further aspect of the invention provides a method of labelling a biological molecule for mass spectrometry detection comprising contacting said molecules with a compound of formula 1 or a pharmaceutically acceptable salt thereof.

DETAILED DESCRIPTION OF THE INVENTION

"Substituted", when used in connection with a chemical substituent or moiety (e.g., an alkyl group), means that one or more hydrogen atoms of the substituent or moiety have been replaced with one or more non-hydrogen atoms or groups, provided that valence requirements are met and that a chemically stable compound results from the substitution.

"Alkyl" refers to straight chain and branched saturated hydrocarbon groups, generally having a specified number of carbon atoms (e.g., $C_{1-3}$ alkyl refers to an alkyl group having 1 to 3 carbon atoms, $C_{1-6}$ alkyl refers to an alkyl group having 1 to 6 carbon atoms, and so on). Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkylene" refers to a divalent radical derived from an alkane which may be a straight chain or branched, as exemplified by —$CH_2CH_2CH_2CH_2$—.

The terms "cycloalkyl" by itself or in combination with other terms, represent, unless otherwise stated, a cyclic versions of "alkyl". Examples of cycloalkyl include cyclopentyl, cyclohexyl, 1-cyclohexenyl, 3-cyclohexenyl, cycloheptyl, and the like.

The term "alkenyl", as used herein, means a hydrocarbon radical having at least one double bond including, but not limited to, ethenyl, propenyl, 1-butenyl, 2-butenyl and the like.

The term "alkenylene" refers to a divalent radical derived from an alkenyl which may be a straight chain or branched, containing one or more double bonds, as exemplified by, —$CH_2CH$═CH—, or —$CH_2CH(CH_3)CH$═CH—$CH_2$—.

The term "alkynyl", as used herein, means a hydrocarbon radical having at least one triple bond including, but not limited to, ethynyl, propynyl, 1-butynyl, 2-butynyl and the like.

The term "alkynylene" refers to a divalent unsaturated hydrocarbon group which may be linear or branched, containing one or more carbon-carbon triple bonds, as exemplified by, ethyne-1,2-diyl.

"Aryl" employed alone or in combination with other terms (e.g., aryloxy, arylthioxy, arylalkyl) refers to fully unsaturated monocyclic aromatic hydrocarbons and to polycyclic hydrocarbons having at least one aromatic ring, both monocyclic and polycyclic aryl groups generally having a specified number of carbon atoms that comprise their ring members (e.g., $C_{6-14}$ aryl refers to an aryl group having 6 to 14 carbon atoms as ring members). The aryl group may be attached to a parent group or to a substrate at any ring atom and may include one or more non-hydrogen substituents unless such attachment or substitution would violate valence requirements. Examples of aryl groups include phenyl, biphenyl, cyclobutabenzenyl, indenyl, naphthalenyl, benzocycloheptenyl, biphenylenyl, fluorenyl, groups derived from cycloheptatriene cation, and the like.

"Arylene" refers to a divalent radical derived from an aryl group.

The term "alkoxy", as used herein, means an O-alkyl group wherein "alkyl" is defined above.

The term "aralkyl" or "arylalkyl" means an aryl-alkyl-group in which the aryl and alkyl are as previously described. Preferred aralkyls comprise a lower alkyl group attached to the aryl group. Non-limiting examples of suitable aralkyl groups include phenylmethylene, 2-phenethyl and naphthalenylmethyl. The bond to the parent moiety is through the alkyl.

"Cycloalkyl" refers to saturated monocyclic and bicyclic hydrocarbon groups, generally having a specified number of carbon atoms that comprise the ring or rings (e.g., $C_{3-8}$ cycloalkyl refers to a cycloalkyl group having 3 to 8 carbon atoms as ring members). Bicyclic hydrocarbon groups may include isolated rings (two rings sharing no carbon atoms), spiro rings (two rings sharing one carbon atom), fused rings (two rings sharing two carbon atoms and the bond between the two common carbon atoms), and bridged rings (two rings sharing two carbon atoms, but not a common bond). The cycloalkyl group may be attached to a parent group or to a substrate at any ring atom unless such attachment would violate valence requirements. In addition, the cycloalkyl group may include one or more non-hydrogen substituents unless such substitution would violate valence requirements.

Examples of monocyclic cycloalkyl groups include cyclopropyl, cyclobutyl, cyclopentyl, cyclohexyl, and the like. Examples of fused bicyclic cycloalkyl groups include bicyclo[2.1.0]pentanyl (i.e., bicyclo[2.1.0]pentan-1-yl, bicyclo [2.1.0]pentan-2-yl, and bicyclo[2.1.0]pentan-5-yl), bicyclo [3.1.0]hexanyl, bicyclo[3.2.0]heptanyl, bicyclo[4.1.0] heptanyl, bicyclo[3.3.0]octanyl, bicyclo[4.2.0]octanyl, bicyclo[4.3.0]nonanyl, bicyclo[4.4.0]decanyl, and the like. Examples of bridged cycloalkyl groups include bicyclo [2.1.1]hexanyl, bicyclo[2.2.1]heptanyl, bicyclo[3.1.1]heptanyl, bicyclo[2.2.2]octanyl, bicyclo[3.2.1]octanyl, bicyclo [4.1.1]octanyl, bicyclo[3.3.1]nonanyl, bicyclo[4.2.1] nonanyl, bicyclo[3.3.2]decanyl, bicyclo[4.2.2]decanyl, bicyclo[4.3.1]decanyl, bicyclo[3.3.3]undecanyl, bicyclo [4.3.2]undecanyl, bicyclo[4.3.3]dodecanyl, and the like. Examples of spiro cycloalkyl groups include spiro[3.3] heptanyl, spiro[2.4]heptanyl, spiro[3.4]octanyl, spiro[2.5] octanyl, spiro[3.5]nonanyl, and the like. Examples of isolated bicyclic cycloalkyl groups include those derived from bi(cyclobutane), cyclobutanecyclopentane, bi(cyclopentane), cyclobutanecyclohexane, cyclopentanecyclohexane, bi(cyclohexane), etc.

"Drug", "drug substance", "active pharmaceutical ingredient", and the like, refer to a compound (e.g., compounds of Formula 1 and compounds specifically named above) that may be used for treating a subject in need of treatment.

"Excipient" refers to any substance that may influence the bioavailability of a drug, but is otherwise pharmacologically inactive.

"Halo", "halogen" and "halogeno" may be used interchangeably and refer to fluoro, chloro, bromo, and iodo. Additionally, terms such as "fluoroalkyl", are meant to include monofluoroalkyl and polyfluoroalkyl.

"Heteroaryl" refers to unsaturated monocyclic aromatic groups and to polycyclic groups having at least one aromatic ring, each of the groups having ring atoms composed of carbon atoms and 1 to 4 heteroatoms independently selected from nitrogen, oxygen, and sulfur. Both the monocyclic and polycyclic groups generally have a specified number of carbon atoms as ring members (e.g., $C_{1-9}$ heteroaryl refers to a heteroaryl group having 1 to 9 carbon atoms and 1 to 4 heteroatoms as ring members) and may include any bicyclic group in which any of the above-listed monocyclic heterocycles are fused to a benzene ring. The heteroaryl group may be attached to a parent group or to a substrate at any ring atom and may include one or more non-hydrogen substituents unless such attachment or substitution would violate valence requirements or result in a chemically unstable compound. Examples of heteroaryl groups include monocyclic groups such as pyrrolyl (e.g., pyrrol-1-yl, pyrrol-2-yl, and pyrrol-3-yl), furanyl, thiophenyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, and pyrazinyl.

Examples of heteroaryl groups also include bicyclic groups such as benzofuranyl, isobenzofuranyl, benzothiophenyl, benzo[c]thiophenyl, indolyl, 3H-indolyl, isoindolyl, 1H-isoindolyl, indolinyl, isoindolinyl, benzimidazolyl, indazolyl, benzotriazolyl, chromanyl, 2-phenylchromanyl, 3-phenylchromanyl, 4-phenylchromanyl, chromen-4-only, 2-phenylchromen-4-only, 3-phenylchromen-4-only, coumarinyl, 3-phenylcoumarinyl, 4-phenylcoumarinyl, 1,8-bis [2-chromanyl]-6-benzo[7]annuleonyl, 1H-pyrrolo[2,3-b] pyridinyl, 1H-pyrrolo[2,3-c]pyridinyl, 1H-pyrrolo[3,2-c] pyridinyl, 1H-pyrrolo[3,2-b]pyridinyl, 3H-imidazo[4,5-b] pyridinyl, 3H-imidazo[4,5-c]pyridinyl, 1H-pyrazolo[4,3-b] pyridinyl, 1H-pyrazolo[4,3-c]pyridinyl, 1H-pyrazolo[3,4-c] pyridinyl, 1H-pyrazolo[3,4-b]pyridinyl, 7H-purinyl, indolizinyl, imidazo[1,2-c]pyridinyl, imidazo[1,5-c]pyridinyl, pyrazolo[1,5-c]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3, 2-c]pyrimidinyl, pyrido[4,3-c]pyrimidinyl, pyrido[3,4-c] pyrimidinyl, pyrido[2,3-c]pyrimidinyl, pyrido[2,3-b] pyrazinyl, pyrido[3,4-b]pyrazinyl, pyrimido[5,4-c] pyrimidinyl, pyrazino[2,3-b]pyrazinyl, and pyrimido[4,5-c] pyrimidinyl.

"Heterocycle" and "heterocyclyl" may be used interchangeably and refer to saturated or partially unsaturated monocyclic or bicyclic groups having ring atoms composed of carbon atoms and 1 to 4 heteroatoms independently selected from nitrogen, oxygen, and sulfur. Both the monocyclic and bicyclic groups generally have a specified number of carbon atoms in their ring or rings (e.g., $C_{2-5}$ heterocyclyl refers to a heterocyclyl group having 2 to 5 carbon atoms and 1 to 4 heteroatoms as ring members). As with bicyclic cycloalkyl groups, bicyclic heterocyclyl groups may include isolated rings, spiro rings, fused rings, and bridged rings. The heterocyclyl group may be attached to a parent group or to a substrate at any ring atom and may include one or more non-hydrogen substituents unless such attachment or substitution would violate valence requirements or result in a chemically unstable compound. Examples of monocyclic heterocyclyl groups include oxiranyl, thiaranyl, aziridinyl (e.g., aziridin-1-yl and aziridin-2-yl), oxetanyl, thiatanyl, azetidinyl, tetrahydrofuranyl, tetrahydrothiophenyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4- dihydro-2H-pyranyl, 5,6-dihydro-2H-pyranyl, 2H-pyranyl, 1,2,3,4-tetrahydropyridinyl, and 1,2,5,6-tetrahydropyridinyl "Pharmaceutically acceptable" substances refers to those substances which are within the scope of sound medical judgment suitable for use in contact with the tissues of subjects without undue toxicity, irritation, allergic response, and the like, commensurate with a reasonable benefit-to-risk ratio, and effective for their intended use.

"Pharmaceutical composition" refers to the combination of one or more drug substances and one or more excipients.

The term "sulfonyl" refers to a radical —$S(O)_2R$ where R is an alkyl, substituted alkyl, substituted cycloalkyl, substituted heterocycloalkyl, substituted aryl, or substituted heteroaryl group as defined herein. Representative examples include, but are not limited to methylsulfonyl, ethylsulfonyl, propylsulfonyl, butylsulfonyl, and the like.

The term "sulfinyl" refers to a radical —S(O)R where R is an alkyl, substituted alkyl, substituted cycloalkyl, substituted heterocycloalkyl, substituted aryl, or substituted heteroaryl group as defined herein. Representative examples include, but are not limited to, methylsulfinyl, ethylsulfinyl, propylsulfinyl, butylsulfinyl, and the like.

The term "subject" as used herein refers to a human or non-human mammal. Examples of non-human mammals include livestock animals such as sheep, horses, cows, pigs, goats, rabbits, deer, ostriches and emus; and companion animals such as cats, dogs, rodents, and horses.

"Therapeutically effective amount" of a drug refers to the quantity of the drug that may be used for treating a subject and may depend on the weight and age of the subject and the route of administration, among other things.

"Treating" refers to reversing, alleviating, inhibiting the progress of, or preventing a disorder, disease or condition to which such term applies, or to reversing, alleviating, inhibiting the progress of, or preventing one or more symptoms of such disorder, disease or condition.

"Treatment" refers to the act of "treating", as defined immediately above.

As used herein the term "comprising" means "consisting at least in part of". When interpreting each statement in this specification that includes the term "comprising", features other than that or those prefaced by the term may also be present. Related terms such as "comprise" and "comprises" are to be interpreted in the same manner.

Dicarbonyl Sequestering Moiety

The dicarbonyl sequestering moiety A comprises a substituted aryl group or a substituted heteroaryl group. A diacarbonyl sequestering moiety is a moiety that forms a stable compound, such as a quinoxaline compound, with a dicarbonyl molecule, suitably, with a 1,2-dicarbonyl molecule. The dicarbonyl sequestering moiety is used to sequester dicarbonyl molecules in biological systems, such as the dilute solutions found in cells. In order for the dicarbonyl sequestering moiety to form a stable compound with a dicarbonyl molecule under the conditions found in cells, the dicarbonyl sequestering moiety must be sufficiently nucleophilic to form adducts spontaneously with the dicarbonyl molecule at low concentrations in water at body temperature. In the dilute solutions of biological systems, such as those found in cells, the first step to produce a stable compound with a dicarbonyl compound is to form a hemiacetal, hemiaminal or hemithioacetal which is a reversible reaction with the equilibrium in favour of the starting materials.

Suitably the substituted aryl group, or the substituted heteroaryl group comprises two or more substituent groups independently selected from —$NH_2$, —$NHR_1$, —$NR_1R_1$, —$^1X$—$NH_2$, —$^1X$—$NHR_1$, —O—$NH_2$, —O—$NHR_1$, —$^1X$—O—$NH_2$, —$^1X$—O—$NHR_1$, —NR'—NHR', —$^1X$—NR'—NHR' and —$NHCOR_1$.

Suitably the substituted aryl group or substituted heteroaryl group comprises from two to nine substituent groups. More suitably, the substituted aryl group or substituted heteroaryl group comprises from two to eight substituent groups; from two to seven substituent groups; from two to six substituent groups; or from two to five substituent groups.

Suitably the substituted aryl group or substituted heteroaryl group comprises from two to nine substituent groups independently selected from —OH, —$OR_1$, —$NH_2$, —$NHR_1$, —$NR_1R_1$, —$^1X$—$NH_2$, —$^1X$—$NHR_1$, —O—$NH_2$, —O—$NHR_1$, —$^1X$—O—$NH_2$, —$^1X$—O—$NHR_1$, —NR'—NHR', —$^1X$—NR'—NHR', —$NHCOR_1$ and —O—C(O)—$R_1$.

Thus, the substituent groups may comprise hydrazine derivatives such as —NH—$NH_2$, —NH—NH($C_{1-6}$ alkyl), —N($C_{1-6}$ alkyl)-$NH_2$, —N($C_{1-6}$ alkyl)-NH($C_{1-6}$ alkyl), —$^1X$—NH—$NH_2$, —$^1X$—NH—NH($C_{1-6}$ alkyl), —$^1X$—N($C_{1-6}$ alkyl)-$NH_2$ and —$^1X$—N($C_{1-6}$ alkyl)-NH($C_{1-6}$ alkyl).

Suitably the substituted aryl group, or the substituted heteroaryl group comprises two or more substituent groups independently selected from —OH, —$OR_1$, —$NH_2$, —$NHR_1$, —$NR_1R_1$, —$^1X$—$NH_2$, —$^1X$—$NHR_1$, —$NHCOR_1$, and —O—C(O)—$R_1$.

Suitably the substituted aryl group, or the substituted heteroaryl group comprises two or more substituent groups independently selected from —$NH_2$, —$NHR_1$, —$NR_1R_1$, —$^1X$—$NH_2$, —$^1X$—$NHR_1$ and —$NHCOR_1$.

Suitably the substituted aryl group, or the substituted heteroaryl group comprises two or more substituent groups independently selected from —OH, —$OR_1$, —$NH_2$, —$NHR_1$, —$NR_1R_1$, —$C_{1-6}$ alkylene-$NH_2$, —$C_{1-6}$ alkylene-$NHR_1$, —$NHCOR_1$, and —O—C(O)—$R_1$.

More suitably the substituted aryl group, or the substituted heteroaryl group comprises two or more substituent groups independently selected from —OH, —$OR_1$, —$NH_2$ and —$C_{1-6}$ alkylene-$NH_2$.

More suitably the substituted aryl group, or the substituted heteroaryl group comprises two or more substituent groups independently selected from —$NH_2$ and —$C_{1-6}$ alkylene-$NH_2$.

Suitably the substituted aryl group, or the substituted heteroaryl group comprises from one to seven of the optional substituent groups; from one to six of the optional substituent groups; from one to five of the optional substituent groups; from one to four of the optional substituent groups; from one to three of the optional substituent groups.

Suitably, the substituted aryl group, or the substituted heteroaryl group comprises one or more of the optional substituent groups selected from —$C_{1-6}$ alkyl, —$C_{2-6}$ alkenyl, —$C_{2-6}$ alkynyl, -halogen, —$^1X$—OH, —$^1X$—O—$R_1$, —$CO_2H$, —$^1X$—$CO_2H$, —$CO_2R_1$, —$^1X$—$CO_2R_1$, —C(O)$NH_1$, —C(O)$NHR_1$, —$SO_2NH_2$ and —$SO_2NHR_1$.

Suitably, the substituted aryl group, or the substituted heteroaryl group comprises one or more of the optional substituent groups selected from —$C_{1-6}$ alkyl, -halogen, —$C_{1-6}$ alkylene-OH, —$C_{1-6}$ alkylene-O—$R_1$, —$CO_2H$, —$C_{1-6}$ alkylene-$CO_2H$, —$CO_2R_1$, —$C_{1-6}$ alkylene-$CO_2R_1$, —$C_{1-6}$ alkylene-O—C(O)—$R_1$, —CHO and —C(O)—$R_1$, —C(O)$NH_2$, —C(O)$NHR_1$, —$SO_2NH_2$ and —$SO_2NHR_1$.

Suitably, the substituted aryl group, or the substituted heteroaryl group comprises one or more of the optional substituent groups selected from —$C_{1-6}$ alkyl, -halogen, —$C_{1-6}$ alkylene-OH, —$C_{1-6}$ alkylene-O—$R_1$, —$CO_2H$, —$CO_2R_1$.

More suitably, $R_1$ is a —$C_{1-6}$ alkyl. More suitably, $R_1$ is selected from methyl, ethyl, n-propy, i-propyl, n-butyl, s-butyl, i-butyl and t-butyl.

More suitably, $R_1$ has the structure of Formula 2:

Formula 2

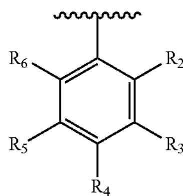

wherein each group $R_2$-$R_6$ is independently selected from —H, —$C_{1-6}$ alkyl, -halogen, —OH, —$C_{1-6}$ alkylene-OH, —O—$C_{1-6}$ alkyl, —$C_{1-6}$ alkylene-O—$C_{1-6}$ alkyl, —$NH_2$, —($C_1$-$C_6$)alkylene-$NH_2$, —$CO_2H$ and —$CO_2C_{1-6}$ alkyl.

More suitably, two or more of $R_2$-$R_6$ are —H.

More suitably, $R_2$ and $R_6$ are —H.

More suitably, $R_2$ and $R_6$ are —H and $R_3$, $R_4$ and $R_5$ are —OH

Suitably, A is a dicarbonyl sequestering moiety comprising a substituted aryl group selected from substituted phenyl, biphenyl and naphthalenyl; or a substituted heteroaryl group selected from substituted pyrrolyl, furanyl, thiophenyl, pyrazolyl, imidazolyl, pyridinyl, pyridazinyl, pyrimidinyl, chromanyl, 2-phenylchromanyl, 3-phenylchromanyl, 4-phenylchromanyl, chromen-4-only, 2-phenylchromen-4-only, 3-phenylchromen-4-only, coumarinyl, 3-phenylcoumarinyl, 4-phenylcoumarinyl and 1,8-bis[2-chromanyl]-6-benzo [7]annuleonyl.

More suitably, A is a dicarbonyl sequestering moiety comprising a substituted aryl group selected from substituted phenyl and naphthalenyl; or a substituted heteroaryl group selected from substituted pyridinyl, chromanyl, 2-phenylchromanyl, 3-phenylchromanyl, 4-phenylchromanyl, chromen-4-only, 2-phenylchromen-4-only, 3-phenylchromen-4-only, coumarinyl, 3-phenylcoumarinyl, 4-phenylcoumarinyl and 1,8-bis[2-chromanyl]-6-benzo [7]annuleonyl.

More suitably, A is a dicarbonyl sequestering moiety comprising a substituted aryl group selected from substituted phenyl and naphthalenyl; or a substituted heteroaryl group selected from substituted pyridinyl.

More suitably, the dicarbonyl sequestering moiety A is a substituted phenyl.

More suitably, the dicarbonyl sequestering moiety A is a substituted phenyl comprising from two to five substituent groups; more suitably, from two to four substituent groups; more suitably, from two to three substituent groups.

More suitably, the dicarbonyl sequestering moiety A is a substituted aryl group comprising Formula 3:

Formula 3

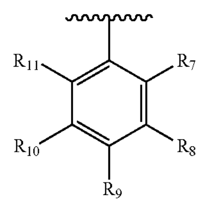

wherein two or more of $R_7$-$R_{11}$ are independently selected from —OH, —$OR_1$, —$NH_2$, —$NHR_1$, —$NR_1R_1$, —$C_{1-6}$ alkylene-$NH_2$, —$C_{1-6}$ alkylene-$NHR_1$, —O—$NH_2$, —O—$NHR_1$, —$C_{1-6}$ alkylene-O—$NH_2$, —$C_{1-6}$ alkylene-O—$NHR_1$, —$NHCOR_1$, —O—C(O)—$R_1$, —NR'—NHR', —$C_{1-6}$ alkylene —NR'—NHR'; and the remaining groups $R_7$-$R_{11}$ are independently selected from —H, —$C_{1-6}$ alkyl, —$C_{2-6}$ alkenyl, —$C_{2-6}$ alkynyl, -halogen, —$C_{1-6}$ alkylene-OH, —$C_{1-6}$ alkylene-O—$R_1$, —$CO_2H$, —$C_{1-6}$ alkylene-$CO_2H$, —$CO_2R_1$, —$C_{1-6}$ alkylene-$CO_2R_1$, —$C_{1-6}$ alkylene-O—C(O)—$R_1$, —CH(OH)—C(O)—$R_1$, —$C_{1-6}$ alkylene-CH(OH)—C(O)—$R_1$, —CHO, —C(O)—$R_1$, —C(O)$NH_2$, —C(O)$NHR_1$, —$SO_2NH_2$ and —$SO_2NHR_1$.

More suitably two or more of $R_7$-$R_{11}$ are independently selected from —OH, —$NH_2$, —O$C_1$-$C_6$ alkyl, —NH($C_1$-$C_6$ alkyl), —$C_1$-$C_6$ alkylene-$NH_2$, —$C_1$-$C_6$ alkylene-NH($C_1$-$C_6$ alkyl).

More suitably two or more of $R_7$-$R_{11}$ are independently selected from —OH, —O$C_1$-$C_6$ alkyl, —$NH_2$, —NH($C_1$-$C_6$ alkyl), —$C_1$-$C_6$ alkylene-$NH_2$ and —$C_1$-$C_6$ alkylene-NH ($C_1$-$C_6$ alkyl); and the remaining groups $R_7$-$R_{11}$ are independently selected from —H, —$C_{1-6}$ alkyl, —$C_{1-6}$ alkylene-OH, —$C_{1-6}$ alkylene-O—$C_{1-6}$ alkyl, —$CO_2H$, —$CO_2C_{1-6}$ alkyl, —CH(OH)—C(O)—$C_{1-6}$ alkyl and —CHO.

Suitably, from one to three of $R_7$-$R_{11}$ are —H.

More suitably two or more of $R_7$-$R_{11}$ is independently selected from —OH, —O$C_1$-$C_6$ alkyl, —$NH_2$, —NH($C_1$-$C_6$ alkyl), —$C_1$-$C_6$ alkylene-$NH_2$ and —$C_1$-$C_6$ alkylene-NH ($C_1$-$C_6$ alkyl); and the remaining groups $R_7$-$R_{11}$ are independently selected from —H, —$C_{1-6}$ alkyl, —$C_{1-6}$ alkylene-OH and —$C_{1-6}$ alkylene-O$C_{1-6}$ alkyl.

More suitably, $R_7$=—H, $R_{10}$=—H, and $R_{11}$=—H, and $R_8$ and $R_9$ are independently selected from —OH, —$OR_1$, —$NH_2$, —$NHR_1$, —$C_{1-6}$ alkylene-$NH_2$, —$C_{1-6}$ alkylene-$NHR_1$, —O—$NH_2$, —O—$NHR_1$, —$C_{1-6}$ alkylene-O—$NH_2$, —$C_{1-6}$ alkylene-O—$NHR_1$, —$NHCOR_1$ and —O—C(O)—$R_1$.

More suitably, $R_7$=—H, $R_{10}$=—H, and $R_{11}$=—H, and $R_8$ and $R_9$ are independently selected from OH, —O$C_1$-$C_6$ alkyl, —$NH_2$, —NH($C_1$-$C_6$ alkyl), —$C_1$-$C_6$ alkylene-$NH_2$ and —$C_1$-$C_6$ alkylene-NH($C_1$-$C_6$ alkyl).

More suitably, $R_7$=—H, $R_{10}$=—H, and $R_{11}$=—H, and $R_8$ and $R_9$ are independently selected from —OH, —$C_1$-$C_6$ alkylene-OH, —$NH_2$ and —$C_1$-$C_6$ alkylene-$NH_2$.

More suitably, $R_7$=—H, $R_8$=—$NH_2$, $R_9$=—$NH_2$, $R_{10}$=—H, and $R_{11}$=—H. This results in a dicarbonyl sequestering moiety A of Formula 4:

Formula 4

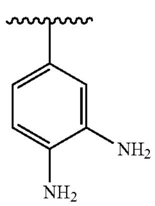

In one aspect, the dicarbonyl sequestering moiety A comprises a substituted flavonoid or theaflavin compound which comprises a heteroaryl group selected from substituted chromanyl, 2-phenylchromanyl, 3-phenylchromanyl, 4-phenylchromanyl, chromen-4-only, 2-phenylchromen-4-only, 3-phenylchromen-4-only, coumarinyl, 3-phenylcoumarinyl, 4-phenylcoumarinyl and 1,8-bis[2-chromanyl]-6-benzo[7]annuleonyl.

The trapping of species such as glyoxal and methylglyoxal with various flavonoid or theaflavin compounds have been described [55]-[57].

More suitably, the substituted flavonoid or theaflavin compound comprises one or more substituent groups independently selected from —OH, —$OR_1$, —$NHCOR_1$ and —O—C(O)—$R_1$; and may optionally comprises one or more substituent groups selected from —$C_{1-6}$ alkyl, -halogen, —$C_{1-6}$ alkylene-OH, —$C_{1-6}$ alkylene-O—$R_1$, —$CO_2H$, —$CO_2R_1$, —CH(OH)—C(O)—$R_1$ and —CHO, and wherein $R_1$ is a —$C_{1-6}$ alkyl or has Formula 2:

Formula 2

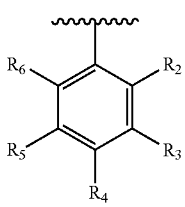

wherein the or each group $R_2$-$R_6$ is independently selected from —H, —$C_{1-6}$ alkyl, -halogen, —OH and —O—$C_{1-6}$ alkyl.

More suitably, the substituted flavonoid compound comprises one or more substituent groups independently selected from —OH, —$OR_1$ and —O—C(O)—$R_1$; and may optionally comprises one or more substituent groups selected from —$C_{1-6}$ alkyl, —$C_{1-6}$ alkylene-OH, —$C_{1-6}$ alkylene-O—$R_1$, —$CO_2H$ and —$CO_2R_1$, and wherein $R_1$ is a —$C_{1-6}$ alkyl or has Formula 2:

Formula 2

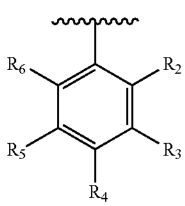

wherein the or each group $R_2$-$R_6$ is independently selected from —H, —$C_{1-6}$ alkyl and —OH.

In some aspects, A is a dicarbonyl sequestering moiety that does not include a benzoquinone moiety.

Suitably, $^1X$ is selected from $C_{1-6}$ alkylene and $C_{2-6}$ alkenylene.

More suitably, $^1X$ is a $C_{1-6}$ alkylene.

The ability of a diacarbonyl sequestering moiety to form a stable compound with a dicarbonyl molecule, such as methylglyoxal, could be tested by carrying out a competition assay with a detection system [64] where the methylglyoxal produces a fluorescent product that can be detected by HPLC.

Linker Moiety

The linker moiety -L- is divalent and may be any chemically non-active distance-making group (spacer) which joins the mitochondrial targeting moiety to the dicarbonyl sequestering moiety, and enables the two moieties to remain bonded together when crossing the plasma and mitochondrial membranes. In particular, -L- is stable under physiological conditions and must be pharmaceutically acceptable.

Suitably -L- is a linker moiety of Formula 5:

$$—(Z_1)_m—X_1—Y_n—[X_2]_s—(Z_2)_t— \quad \text{Formula 5}$$

wherein:

$Z_1$ and $Z_2$ are independently selected from O, $NR_{12}$, $NR_{12}$—C(O), C(O)$NR_{12}$, O—C(O), C(O)—O and S;

Y is selected from O, $NR_{12}$, $NR_{12}$—C(O), C(O)$NR_{12}$, O—C(O), C(O)—O, S and arylene;

wherein $R_{12}$ is selected from —H, —$C_1$-$C_6$ alkyl and -aryl;

$X_1$ is selected from $C_1$-$C_p$ alkylene, $C_2$-$C_p$ alkenylene, $C_2$-$C_p$ alkynylene and $C_3$-$C_p$ cycloalkylene;

$X_2$ is selected from $C_1$-$C_q$ alkylene, $C_2$-$C_q$ alkenylene, $C_2$-$C_q$ alkynylene and $C_3$-$C_q$ cycloalkylene;

each of m, n, s and t is independently selected from 0 or 1;

wherein p+q=30 and wherein $X_1$ and $X_2$ are optionally substituted with one or more functional groups independently selected from the group consisting of hydrogen, alkyl, cycloalkyl, alkenyl, alkynyl, haloalkyl, aryl, aminoalkyl, hydroxyalkyl, alkoxyalkyl, alkylthio, alkylsulfinyl, alkylsulfonyl, carboxyalkyl, cyano, oxy, amino, alkylamino, aminocarbonyl, alkoxycarbonyl, aryloxycarbonyl, alkylaminocarbonyl, arylaminocarbonyl, aralkylaminocarbonyl, alkylcarbonylamino, arylcarbonylamino, aralkylcarbonylamino, alkylcarbonyl, heterocyclocarbonyl, aminosulfonyl, alkylaminosulfonyl, alkylsulfonyl, and heterocyclosulfonyl, or the substituent groups of adjacent carbon atoms in the linker group can be taken together with the carbon atoms to which they are attached to form a carbocycle or a heterocycle.

Suitably, $Z_1$ is adjacent to the dicarbonyl sequestering moiety and $Z_2$ is adjacent to the mitochondrial targeting moiety.

More suitably, $X_1$ is substituted with one or more functional groups independently selected from the group consisting of alkyl, aryl, alkoxycarbonyl, aryloxycarbonyl, alkylaminocarbonyl, arylaminocarbonyl, alkylcarbonylamino and arylcarbonylamino.

More suitably, $X_2$ is substituted with one or more functional groups independently selected from the group consisting of alkyl, aryl, alkoxycarbonyl, aryloxycarbonyl, alkylaminocarbonyl, arylaminocarbonyl, alkylcarbonylamino and arylcarbonylamino.

More suitably, the linker moiety is of Formula 5, wherein:

$Z_1$ and $Z_2$ are as described above;

$X_1$ and $X_2$ are as described above;

Y is selected from $NR_{12}$—C(O), C(O)$NR_{12}$ and O—C(O);

$R_{12}$ is as described above;

p=12;

q=5;

m, n, s and t are as described above; and $X_1$ and $X_2$ are optionally substituted with one or more functional groups independently selected from the group consisting alkyl, aryl, alkoxycarbonyl, aryloxycarbonyl, alkylaminocarbonyl, arylaminocarbonyl, alkylcarbonylamino and arylcarbonylamino.

More suitably, $X_1$ is selected from $C_1$-$C_p$ alkylene.

More suitably, $X_2$ is selected from $C_1$-$C_p$ alkylene.

More suitably, m is 1.

More suitably, -L- is a linker moiety of Formula 6:

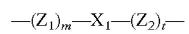

Formula 6 wherein $Z_1$, m, $Z_2$ and t have the same meanings as defined above, $X_1$ is selected from $C_1$-$C_p$ alkylene, $C_2$-$C_p$ alkenylene, $C_2$-$C_p$ alkynylene and $C_3$-$C_p$ cycloalkylene and Cp=30.

More suitably, -L- is a linker moiety of Formula 6 and $Z_1$ and $Z_2$ are independently selected from O, $NR_{12}$, $NR_{12}$—C(═O) and C(═O)$NR_{12}$.

More suitably, $X_1$ is selected from $C_1$-$C_p$ alkylene.

More suitably, -L- is a linker moiety of Formula 6, wherein Cp=25; more suitably, Cp=20; more suitably, Cp=15; more suitably, Cp=12; more suitably, Cp=10; more suitably, Cp=9; more suitably, Cp=8; more suitably, Cp=7; more suitably, Cp=6.

More suitably -L- is a linker moiety of Formula 7:

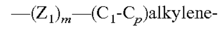

Formula 7 wherein $Z_1$ and m have the same meanings as defined above and Cp=30.

Suitably, $Z_1$ is adjacent to the dicarbonyl sequestering moiety and the $C_1$-$C_p$ alkylene is adjacent to the mitochondrial targeting moiety.

More suitably, -L- is a linker moiety of Formula 7 and m is 1 and $Z_1$ is selected from O and C(O)$NR_{12}$.

More suitably, -L- is a linker moiety of Formula 7 and $R_{12}$ is selected from —H and —$C_1$-$C_6$ alkyl.

More suitably, -L- is a linker moiety of Formula 7 and m is 1 and $Z_1$ is C(O)NH.

More suitably, -L- is a linker moiety of Formula 7 wherein Cp=25; more suitably, Cp=20; more suitably, Cp=15; more suitably, Cp=10; more suitably, Cp=9; more suitably, Cp=8; more suitably, Cp=7; more suitably, Cp=6

More suitably, -L- is a linker moiety of Formula 7 and the $C_1$-$C_p$ alkylene is a $C_3$-$C_6$ alkylene.

More suitably, -L- is a linker moiety of Formula 7, wherein m is 1, $Z_1$ is selected from O and C(O)$NR_{12}$; and the $C_1$-$C_p$ alkylene is selected from a $C_3$-$C_6$ alkylene.

More suitably, -L- is a linker moiety of Formula 7, wherein m is 1, $Z_1$ is C(O)NH; and the $C_1$-$C_p$ alkylene is selected from a $C_3$-$C_6$ alkylene.

In one aspect, -L- is a linker moiety of Formula 8:

Formula 8

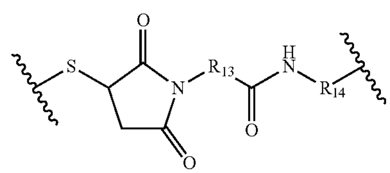

wherein $R_{13}$ is a $C_1$-$C_6$ alkylene, and $R_{14}$ is a $C_1$-$C_6$ alkylene.

In one aspect, -L- is a linker moiety of Formula 9:

Formula 9

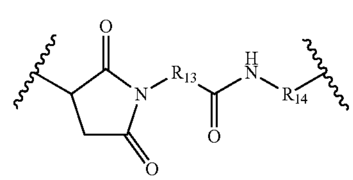

wherein $R_{13}$ is a $C_1$-$C_6$ alkylene, and $R_{14}$ is a $C_1$-$C_6$ alkylene.

More suitably, for Formula 8 or 9 $R_{13}$ is —$CH_2$—$CH_2$—$CH_2$—.

More suitably, for Formula 8 or 9 $R_{14}$ is —$CH_2$—$CH_2$—$CH_2$—.

Linker moieties of Formula 8 or 9 are described in US 2009/0099080.

Mitochondrial Targeting Moiety

Many mitochondrial targeting moieties are known in the art. Compounds comprising mitochondrial targeting moieties accumulate in high concentrations within mitochondria following administration.

The accumulation of compounds comprising mitochondrial targeting moieties within mitochondria may, for example, be driven by plasma membrane potential and/or mitochondrial membrane potentials. Such accumulation can often be adequately described by the Nernst equation and, for example, for compounds comprising a triphenylphosphonium cation may be 10-fold per 60 mV membrane potential under typical biological conditions [25-27]. As a result, compounds comprising a mitochondrial targeting moiety, such as the triphenylphosphonium cation, may accumulate several hundred-fold or more within mitochondria in vivo assuming plasma and mitochondrial membrane potentials of 30 mV and 160 mV respectively [28, 29].

Suitably, the mitochondrial targeting moiety B is a cationic mitochondrial targeting moiety or a mitochondrial targeting peptide.

A range of mitochondrial targeting peptides are known in the art. Suitable examples are disclosed in US 2009/0099080.

Suitably, the mitochondrial targeting moiety B is a cationic mitochondrial targeting moiety. A cationic mitochondrial targeting moiety will also be associated with a pharmaceutically acceptable anion.

Suitably, the anion is selected from acetate, hydrochloride/chloride, hydrobromide/bromide, hydroiodide/iodide, bisulfate, sulfate, methylsulfonate, nitrate, phosphate, hydrogen phosphate, dihydrogen phosphate and trifluoroacetate salts.

Suitably, the mitochondrial targeting moiety B is a lipophilic cation.

Liphophilic cations are suitable mitochondrial targeting moieties because they can readily pass directly through phospholipid bilayers without having to overcome large energy barriers or requiring a specific uptake mechanism, and they accumulate substantially within mitochondria due to the large membrane potential.

Without wishing to be bound to one theory, it is believed that lipophilic cations are taken up from a positively charged cellular compartment into a negatively charged compartment until a sufficiently large concentration gradient is built up to equalize the electrochemical potential of the molecules in the two compartments. For every 60 mV increase in membrane potential, there will be approximately tenfold accumulation of the lipophilic cation within mitochondria. Because the plasma membrane has a negative 30-60 mV potential on the inside, lipophilic cations will accumulate 5 to 10 fold in the cytosol. Lipophilic cations within the cytosol will accumulate in mitochondria because the mitochondrial membrane potential is typically about 140 to 180 mV.

Suitably, the mitochondrial targeting moiety B is selected from:

(i) cationic mitochondrial targeting moieties comprising a quaternary ammonium or phosphonium cation;

(ii) cationic mitochondrial targeting moieties comprising a 1,4a,8-triaza-2,3,4,5,6,7-hexahydro-1H-napthalene compound; and (iii) cationic mitochondrial targeting moieties comprising a Rhodamine compound.

More suitably B is (i) a cationic mitochondrial targeting moiety comprising a quaternary ammonium or phosphonium cation of Formula 10:

Formula 10

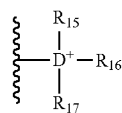

wherein:

D is phosphorous, nitrogen or arsenic; and each of $R_{15}$, $R_{16}$ and $R_{17}$ is independently selected from substituted or unsubstituted alkyl, benzyl, aryl and heteroaryl.

More suitably D is phosphorous.

More suitably, each of $R_{15}$, $R_{16}$ and $R_{17}$ is independently selected from substituted or unsubstituted alkyl, benzyl, phenyl, naphthyl, furanyl, pyridyl and thiophenyl.

More suitably, where any of $R_{15}$, $R_{16}$ and $R_{17}$ are substituted, the substituted alkyl, benzyl, aryl or heteroaryl are substituted with from 1 to 3 substitutents selected from the group consisting of -halogen, —OH, —SH, —$OC_{1-6}$ alkyl, —$SC_{1-6}$ alkyl, —SPh, —$C_{1-6}$ alkyl, —$C_{2-6}$ alkenyl, —$C_{1-6}$ alkynyl, —$C_{1-6}$ hydroxyalkyl, —$C_{1-6}$ aminoalkyl, —$C_{6-18}$ aralkyl, —$C_{6-12}$ aryl, —$C_{3-8}$ cycloalkyl, —$C_{1-12}$ heteroaryl and —$C_{1-12}$ heterocyclyl.

Suitably, where one or more of $R_{15}$, $R_{16}$ and $R_{17}$ is independently selected from substituted or unsubstituted alkyl, each alkyl group is independently selected from a substituted or unsubstituted $C_{1-30}$ alkyl. More suitably, each alkyl group is independently selected from a substituted or unsubstituted $C_{1-25}$ alkyl; from a substituted or unsubstituted $C_{1-20}$ alkyl; from a substituted or unsubstituted $C_{1-15}$ alkyl; from a substituted or unsubstituted $C_{1-10}$ alkyl.

More suitably each of $R_{15}$, $R_{16}$ and $R_{17}$ are the same.

More suitably each $R_{15}$, $R_{16}$ and $R_{17}$ is an unsubstituted or a substituted aryl group.

More suitably each $R_{15}$, $R_{16}$ and $R_{17}$ is an unsubstituted aryl group.

More suitably each aryl group is phenyl.

Most suitably, B is a triphenylphosphonium (TPP) cation, which has the Formula 11:

Formula 11

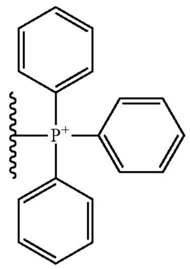

The large hydrophobic radius of the TPP cation enables it to pass easily through the phospholipid bilayer relative to other cations.

Lipophilic triphenylphosphonium (TPP) cation functionality is suitable to target mitochondria and it has been shown to direct a wide variety of antioxidants, probes and bioactive molecules to mitochondria in cells, animal models and patients following intravenous, oral or intraperitoneal administration [25-27]. Uptake occurs directly through the phospholipid bilayer and does not require a protein carrier, while the extent of accumulation into mitochondria is determined by the membrane potential.

More suitably, B is (ii) a cationic mitochondrial targeting moiety comprising 1,4a,8-triaza-2,3,4,5,6,7-hexahydro-1H-napthalene compound of Formula 12

Formula 12

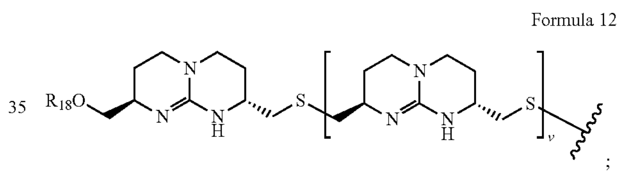

wherein $R_{18}$ is —H, —$C_1$-$C_6$ alkyl, —$C_1$-$C_6$ alkenyl, —$C_1$-$C_6$ alkynyl, —$C_1$-$C_6$ alkylene-halogen, -aryl, -aryl-$C_1$-$C_6$alkyl or $R_{19}R_{20}R_{21}Si$ wherein $R_{19}$, $R_{20}$ and $R_{21}$ are independently selected from —$C_1$-$C_6$ alkyl and -aryl; and v is 1, 2 or 3. Such cationic mitochondrial targeting moieties are described in US 2009/099080.

As disclosed in US 2009/099080, linker moieties of Formula 9 are suitable for use with cationic mitochondrial targeting moieties of Formula 12

More suitably, B is (iii) a cationic mitochondrial targeting moiety comprising a Rhodamine compound of Formula 13:

Formula 13

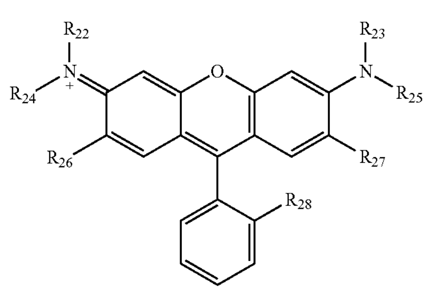

wherein $R_{22}$, $R_{23}$ and $R_{24}$ are independently selected from —H and —$C_1$-$C_6$ alkyl;

$R_{26}$ and $R_{27}$ are independently selected from —H or —$CH_3$;

$R_{28}$ is selected from —$CO_2R_{29}$, —O—C(O)—$R_{29}$, —C(O)—$NHR_{29}$ and —NH—C(O)—$R_{29}$; and one of $R_{25}$ and $R_{29}$ is a bond to the linker L and the other of $R_{25}$ and $R_{28}$ is selected from —H and —$C_1$-$C_6$ alkyl.

A large number of Rhodamine derivatives such as Rhodamine 123, Rhodamine B, Rhodamine 6G, Rhodamine 19, Rhodamine 110, and Rhodamine 116 are commercially available from suppliers such as Acos Organics, Aldrich and Fluka. The synthesis of Rhodamine derivatives has also been reviewed [54].

Further Compounds of Formula 1

Suitably, the compound or pharmaceutically acceptable salt of Formula 1 is a salt of Formula 14:

Formula 14

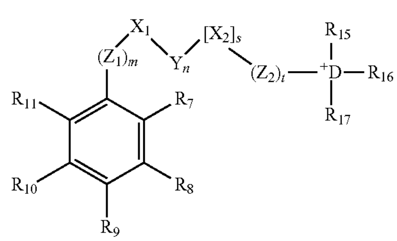

wherein $R_7$, $R_8$, $R_9$, $R_{10}$, $R_{11}$, $R_{15}$, $R_{16}$, $R_{17}$, $Z_1$, $X_1$, Y, $X_2$, $Z_2$, D, m, n, s and t have the same meanings as described above. The salt of Formula 14 may optionally further comprise a pharmaceutically acceptable anion.

More suitably, the compound or pharmaceutically acceptable salt of Formula 1 is a salt of Formula 15:

Formula 15

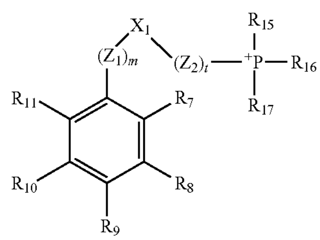

wherein $R_7$, $R_8$, $R_9$, $R_{10}$, $R_{11}$, $R_{15}$, $R_{16}$, $R_{17}$, $Z_1$, $X_1$, $Z_2$, m and t have the same meanings as described above. The salt of Formula 15 may optionally further comprise a pharmaceutically acceptable anion.

More suitably, the compound of Formula 1 is MitoG which has the structure shown in Formula 16:

Formula 16

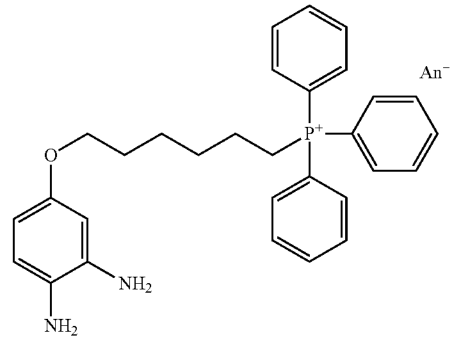

wherein $An^-$ represents an optional pharmaceutically acceptable anion.

Another example of a compound of Formula 1 is MitoGamide, (3-(3,4-diaminobenoylamino)propyl)triphenylphosphonium salt, which has the structure shown in Formula 17:

Formula 17

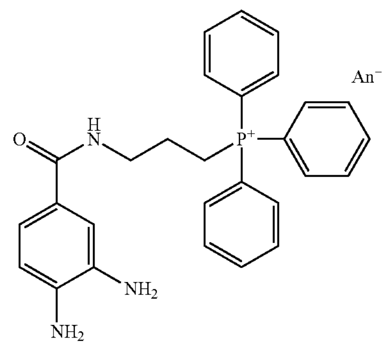

wherein $An^-$ represents an optional pharmaceutically acceptable anion.

Suitably, the anion $An^-$ is selected from acetate, hydrochloride/chloride, hydrobromide/bromide, hydroiodide/iodide, bisulfate, sulfate, methylsulfonate, nitrate, phosphate, hydrogen phosphate, dihydrogen phosphate and trifluoroacetate salts.

More suitably, the anion $An^-$ is the chloride salt.

These molecules comprise a mitochondrial targeting group, such as a triphenylphosphonium ion (TPP), linked through an oxygen atom to a sequestering group, such as an o-phenylenediamine, that reacts selectively with methylglyoxal and glyoxal. Alkoxy-substituted phenylenediamines have been used for detecting 1,2-dicarbonyls because of the enhanced reactivity due to the electron donating alkoxy substituent [28, 29]. These have been as used derivatizing agents for the detection of dicarbonyls, reacting to form stable quinoxaline products [12, 13, 28].

Compounds such as MitoG are demonstrated to be protective, as shown in the examples section.

Compounds such as MitoGamide are also protective and show increased stability.

In designing the MitoG compounds such as MitoG-amides, the characteristics required to bring about the therapeutic benefits of the invention were considered. A need to pull electrons into a separate part of the molecular structure was identified. The inventors identified molecular groups which could be substituted in order to tune the reactivity of the diamine group. Solutions to this problem are provided by the compounds of Formula 1. Preferred solutions include the MitoGamide molecule which provides benefits including enhanced stability.

Compounds of Formula 1, which include compounds specifically named above, may form pharmaceutically acceptable salts. These salts include acid addition salts (including di-acids) and base salts. Pharmaceutically acceptable acid addition salts include nontoxic salts derived from inorganic acids such as hydrochloric acid, nitric acid, phosphoric acid, sulfuric acid, hydrobromic acid, hydroiodic acid, hydrofluoric acid, and phosphorous acids, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfonate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

Pharmaceutically acceptable base salts include nontoxic salts derived from bases, including metal cations, such as an alkali or alkaline earth metal cation, as well as amines. Examples of suitable metal cations include sodium ($Na^+$) potassium ($K^+$), magnesium ($Mg^{2+}$), calcium ($Ca^{2+}$), zinc ($Zn^{2+}$), and aluminum ($Al^{3+}$). Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., J. Pharm. Sci. (1977) 66:1-19; see also Stahl and Wermuth, Handbook of Pharmaceutical Salts: Properties, Selection, and Use (2002).

Pharmaceutically acceptable salts may be prepared using various methods. For example, one may react a compound of Formula 1 with an appropriate acid or base to give the desired salt. One may also react a precursor of the compound of Formula 1 with an acid or base to remove an acid- or base-labile protecting group or to open a lactone or lactam group of the precursor. Additionally, one may convert a salt of the compound of Formula 1 to another salt through treatment with an appropriate acid or base or through contact with an ion exchange resin. Following reaction, one may then isolate the salt by filtration if it precipitates from solution, or by evaporation to recover the salt. The degree of ionization of the salt may vary from completely ionized to almost non-ionized.

Compounds of Formula 1 may also exist in unsolvated and solvated forms. The term "solvate" describes a molecular complex comprising the compound and one or more pharmaceutically acceptable solvent molecules (e.g., EtOH). The term "hydrate" is a solvate in which the solvent is water. Pharmaceutically acceptable solvates include those in which the solvent may be isotopically substituted (e.g., $D_2O$, acetone-d6, DMSO-d6).

A currently accepted classification system for solvates and hydrates of organic compounds is one that distinguishes between isolated site, channel, and metal-ion coordinated solvates and hydrates. See, e.g., K. R. Morris (H. G. Brittain ed.) Polymorphism in Pharmaceutical Solids (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Compounds of Formula 1 may also exist as multi-component complexes (other than salts and solvates) in which the compound (drug) and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together. See, e.g., O. Almarsson and M. J. Zaworotko, Chem. Commun. (2004) 17:1889-1896. For a general review of multi-component complexes, see J. K. Haleblian, J. Pharm. Sci. (1975) 64(8):1269-88.

Synthetic Methods

Methods for the chemical synthesis of compounds of the present invention are described herein. These methods may be modified and/or adapted in known ways in order to facilitate the synthesis of additional compounds within the scope of the present invention. The amounts of reactants given are for guidance. Descriptions of general laboratory methods and procedures, useful for the preparation of the compounds of the present invention, are described in *Vogel's Textbook of Practical Organic Chemistry* (5th edition, Ed. Furniss, B. S., Hannaford, A. J., Smith, P. W. G., Tatchell, A. R., Longmann, UK).

The synthesis of compounds of the present invention may have three key steps:

(i) formation of the dicarbonyl sequestering moiety;

(ii) attachment of the linking group to the dicarbonyl sequestering moiety; and (iii) attachment of the linking group to the mitochondrial targeting moiety.

In some cases, the starting material for formation of the dicarbonyl sequestering moiety may already include part or all of the linking group. Where all of the linking group is included, then step (ii) is omitted.

These three steps can be carried out in any order, which will be dependent on the methods used and the nature of each of the three groups. It is possible that the formation of the dicarbonyl sequestering moiety can be interrupted by linking a precursor to the linking group. If necessary, protecting groups can be employed to avoid any unwanted reactions occurring during the synthesis.

Formation of the dicarbonyl sequestering moiety: this will depend on the nature of the dicarbonyl sequestering moiety, and can usually be based on the disclosed routes for forming that moiety. It is sometimes convenient to synthesise the dicarbonyl sequestering moiety with a heteroatom (O, S or NH) already attached to the dicarbonyl sequestering moiety in the position where this moiety is desired to be attached to the linker moiety. Such a heteroatom can aid the joining of the linking group to the dicarbonyl sequestering moiety. The dicarbonyl sequestering moiety may also be synthesised with a functional group present, such as a carboxylic acid, which is suitable for further functionalization.

Linking the linking group to the mitochondrial targeting moiety: it is generally preferred to carry this step out by heating an halogenated precursor, preferably an iodinated or brominated precursor (RBr or RI), or a precursor with a strong leaving group, such as a mesylate, sometimes in an appropriate solvent with 2-3 equivalents of the mitochondrial targeting moiety precursor under argon for up to several days. R can either be the linking group, the linking group already attached to the dicarbonyl sequestering moiety, or the linking group attached to a precursor of the dicarbonyl sequestering moiety. Where an halogenated precursor is used in the reaction, the product compound is then isolated as its bromide or iodide salt. To do this the solvent is removed (if necessary), the product is then triturated repeatedly with a compound such as diethyl ether, until an solid remains. This can then dissolved in a solvent, e.g. dichloromethane, and precipitated with diethyl ether to remove the excess unreacted material. This can be repeated. Purification can involve recrystallisation, for example, from methylene chloride/diethyl ether or chromatography on silica gel eluting with dichloromethane/ethanol mixtures.

Linking the linking group to the dicarbonyl sequestering moiety: this will depend on the nature of the dicarbonyl sequestering moiety. One method of achieving this linking is to synthesise the linking group as part of the dicarbonyl sequestering moiety. In this case, the linking group would suitably have a functional group at the end of the linking group that is to be attached to the mitochondrial targeting moiety. Such a functional group may, for example, be a good leaving group such as a mesylate group which could then be reacted with the precursor of the mitochondrial targeting moiety. Alternatively, if the dicarbonyl sequestering moiety has been synthesised with a suitable functional group in place (see above), it may be reacted with a combined mitochondrial targeting-linker precursor moiety using a coupling agent or following activation of one partner as a sulfonyl halide or acid halide. The combined mitochondrial targeting-linker precursor moiety would have an appropriate functional group on the linker, such as an amine. Thus, a carbodiimide or other coupling agent may be used to form an amide from these moieties. For example, in the synthesis of MitoGamide, the dicarbonyl sequestering group armed with a carboxylic acid can be reacted with a TPP-linker-amine using a coupling agent to form an amide. In theory, a dicarbonyl sequestering group-amine could be reacted with TPP-linker-carboxylic acid using a coupling agent provided that the reacting amine is more nucleophilic than the dicarbonyl sequestering unit, or the latter is protected. Similarly, sulfonyl chlorides react rapidly with amines to form sulfonamides in the presence of relatively weak bases to remove HCl, again the sequestering group may need protection to avoid reacting with the sulfonyl chloride.

The compounds of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in a number of treatises, including Richard Larock, *Comprehensive Organic Transformations, A Guide to Functional Group Preparations,* 2nd Ed (2010), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a diacid, etc.). In addition, in some instances, reaction intermediates may be used in subsequent steps without isolation or purification (i.e., in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry,* 4th Edition, (2006) and P. Kocienski, *Protective Groups,* 3rd Edition (2005).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure to a stoichiometric range, a temperature range, a pH range, etc., whether or not expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

Applications

A key aspect of the invention is the blocking or amelioration of damage caused by hyperglycaemia. The invention finds application in the treatment or prevention of downstream consequences of hyperglycaemia.

One application for a compound of formula 1, as defined above, or a pharmaceutically acceptable salt thereof, is for use in the prevention or treatment of hyperglycaemia.

Hyperglycaemia can occur as an age related syndrome. Hyperglycaemia can occur in sepsis, and/or in intensive care/emergency room admissions. Hyperglycaemia can occur as a complication of pregnancy.

Thus, prevention of hyperglycaemia can be important for subjects with a health state that increases the risk of hyperglycaemia compared to a normal healthy subject who does not have that health state. Suitably, there may be provided a compound of formula 1, as defined above, or a pharmaceutically acceptable salt thereof, for use in the prevention or treatment of hyperglycaemia in a subject with a health state selected from sepsis, pregnancy or a health state requiring critical care.

Most specifically, the invention is applied in diabetes such as hyperglycemic diabetes. The invention finds application in the treatment or prevention of the downstream consequences of hyperglycaemia and diabetes (such as hyperglycemic diabetes), for example, to prevent or reduce damage to any suitable organs and tissues such as eyes, heart, kidneys, nervous system and/or pancreas.

The invention is applied to the treatment or prevention of mitochondrial damage associated with dysfunction or dysregulation of glycaemic control, for example mitochondrial damage associated with hyperglycaemia.

Most suitably the invention is applied to the treatment or prevention of molecular consequences of hyperglycaemia.

In one aspect, the invention relates to a compound of Formula 1 or a pharmaceutical salt thereof, for use in slowing the deleterious effects of aging in a subject.

In another aspect, the invention relates to a compound of Formula 1 or a pharmaceutical salt thereof, for use in preventing or reducing glycation-induced toxicity.

In another aspect, the invention relates the invention relates to a compound of Formula 1 or a pharmaceutical salt thereof, for use in preventing or reducing respiratory depression, in particular dicarbonyl-induced respiratory depression.

In another aspect, the invention relates the invention relates to a compound of Formula 1 or a pharmaceutical salt thereof, for use to protect against cell death, in particular to protect against glycation-induced cell death.

A further aspect of the invention provides a compound of formula 1, as defined above, or a pharmaceutically acceptable salt thereof, for use in the preservation of organ and tissue for surgical transplants. In such an application the compound of formula 1 or a pharmaceutically acceptable salt thereof may suitably be administered as a component of a tissue preservation fluid. In this aspect, any suitable organ and tissue for surgical transplants may be preserved; illustrative organ transplants include eyes (e.g. cornea), heart, kidney, nerve cells and pancreas.

A further aspect of the invention provides a compound of formula 1, as defined above, or a pharmaceutically acceptable salt thereof, for use in the storage of blood. In such an application the compound of formula 1 or a pharmaceutically acceptable salt thereof may suitably be administered as a component of a preservation fluid.

Suitably the invention is applied to mammals, most suitably humans.

The invention may be applied to retinal degeneration. Retinal degeneration is a correlate of diabetic complications. The invention may be usefully applied to any other complication of diabetes, specifically hyperglycemic diabetes.

Administration

The compound of the invention can be administered in solid or liquid form such as tablets, powders, capsules, pellets, solutions, suspensions elixirs, emulsions, gels, creams, or suppositories, including rectal and urethral suppositories.

Suitably compounds of the invention may be used to treat humans.

Suitably the dose for humans is orally administered.

Suitably the dose for humans is one per day.

Suitably the dose for humans is provided in tablet form.

The compounds or compositions of the invention may be administered by parenteral administration.

The compound of the invention may be administered intravenously.

The compound of the invention can be administered in a dose of approximately 20-40 mgs per day. Suitably the dose for humans is approximately 80 mgs per day.

Dosing information is provided for an average adult human unless otherwise stated. It is well within the skill of a physician to vary the dose according to characteristics of the patient being treated, for example age, weight, gender etc.

The compound of the invention may be administered intraocularly.

The compound of the invention may be administered intravenously.

The compound of the invention may be administered intraperitoneally.

The compound of the invention may be administered as eye drops.

Administration may be to any suitable tissue or organ, for example, the compounds or compositions of the invention may be administered to the eye, heart, kidney, nervous system and/or pancreas.

The compound of the invention may be administered in combination with one or more pharmaceutically acceptable excipients, carriers or diluents.

Suitable excipients, carriers and diluents can be found in standard pharmaceutical texts. See, for example, *Handbook for Pharmaceutical Additives,* 3rd Edition (eds. M. Ash and I. Ash), 2007 (Synapse Information Resources, Inc., Endicott, N.Y., USA) and *Remington: The Science and Practice of Pharmacy,* 21st Edition (ed. D. B. Troy) 2006 (Lippincott, Williams and Wilkins, Philadelphia, USA) which are incorporated herein by reference.

Excipients for use in the compositions of the invention include, but are not limited to microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavouring agents, colouring matter or dyes, and, if so desired, emulsifying and/or suspending agents as well, together with such diluents as water, ethanol, propylene glycol, glycerin and various like combinations thereof.

Pharmaceutical carriers include solid diluents or fillers, sterile aqueous media and various non-toxic organic solvents, and the like.

Pharmaceutically acceptable carriers include gums, starches, sugars, cellulosic materials, and mixtures thereof. The compound can be administered to a subject by, for example, subcutaneous implantation of a pellet. The preparation can also be administered by intravenous, intra-arterial, or intramuscular injection of a liquid preparation oral administration of a liquid or solid preparation, or by topical application. Administration can also be accomplished by use of a rectal suppository or a urethral suppository.

Further, as used herein "pharmaceutically acceptable carriers" are well known to those skilled in the art and include, but are not limited to, 0.01-0.1M and preferably 0.05M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Pharmaceutically acceptable parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Pharmaceutically acceptable carriers for controlled or sustained release compositions administrable according to the invention include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Pharmaceutically acceptable carriers include compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski and Davis, *Soluble Polymer-Enzyme Adducts, Enzymes as Drugs*, Hocenberg and Roberts, eds., Wiley-Interscience, New York, N.Y., (1981), pp 367-383; and [65]). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Mass Spectrometry

The invention also finds application as a mass spectrometry probe for detection of reactive dicarbonyls.

These mass spectrometry methods enable the assessment of the importance of mitochondrial damage caused by methylglyoxal and glyoxal. Hence, the compounds of Formula 1, for example, the mitochondria-selective molecule MitoG, may be used to assess relative changes in the levels of these damaging species within mitochondria in cells and in vivo.

The mode of action of MitoG, is shown in FIG. 1B. The ability to quantify the accumulation of the quinoxaline products from the in situ reaction of MitoG with methylglyoxal and glyoxal provides an opportunity to assess changes in the levels of these compounds in mitochondria in cells and in vivo. This can be done by an extension of an approach recently developed to assess levels of mitochondrial hydrogen peroxide in vivo by the use of a mitochondria-targeted peroxide reactive compound, MitoB [30, 31]. In this methodology, a diagnostic exomarker product, MitoP, was formed from MitoB, and its levels were determined ex vivo by liquid chromatography-tandem mass spectrometry (LC-MS/MS) of tissue homogenates relative to deuterated internal standards [30, 31]. The sensitivity of such an approach is greatly enhanced by the inherent positive charge of the TPP moiety that decreases the threshold for detection by mass spectrometry (MS), enabling the analysis of femtomol compound/g wet weight tissue [30, 31]. Thus relative changes in methylglyoxal and glyoxal levels within mitochondria can be assessed based upon the extent of accumulation of the MitoG-dicarbonyl quinoxaline reaction products (FIG. 1B). Hence, compounds such as MitoG, provide a mitochondria-targeted probe for methylglyoxal and glyoxal that can be used for the evaluation of 1,2-dicarbonyl production within mitochondria in cells and in vivo. These findings are consistent with mitochondrial glycation contributing to the underlying pathology of hyperglycaemia in diabetes and related disorders.

Further particular and preferred aspects are set out in the accompanying independent and dependent claims. Features of the dependent claims may be combined with features of the independent claims as appropriate, and in combinations other than those explicitly set out in the claims.

Where an apparatus feature is described as being operable to provide a function, it will be appreciated that this includes an apparatus feature which provides that function or which is adapted or configured to provide that function.

BRIEF DESCRIPTION OF THE DRAWINGS

Embodiments of the present invention will now be described further, with reference to the accompanying drawings, in which.

DESCRIPTION OF THE EMBODIMENTS

Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents.

EXPERIMENTAL

Materials and Methods

Chemical Syntheses

Figure 2:
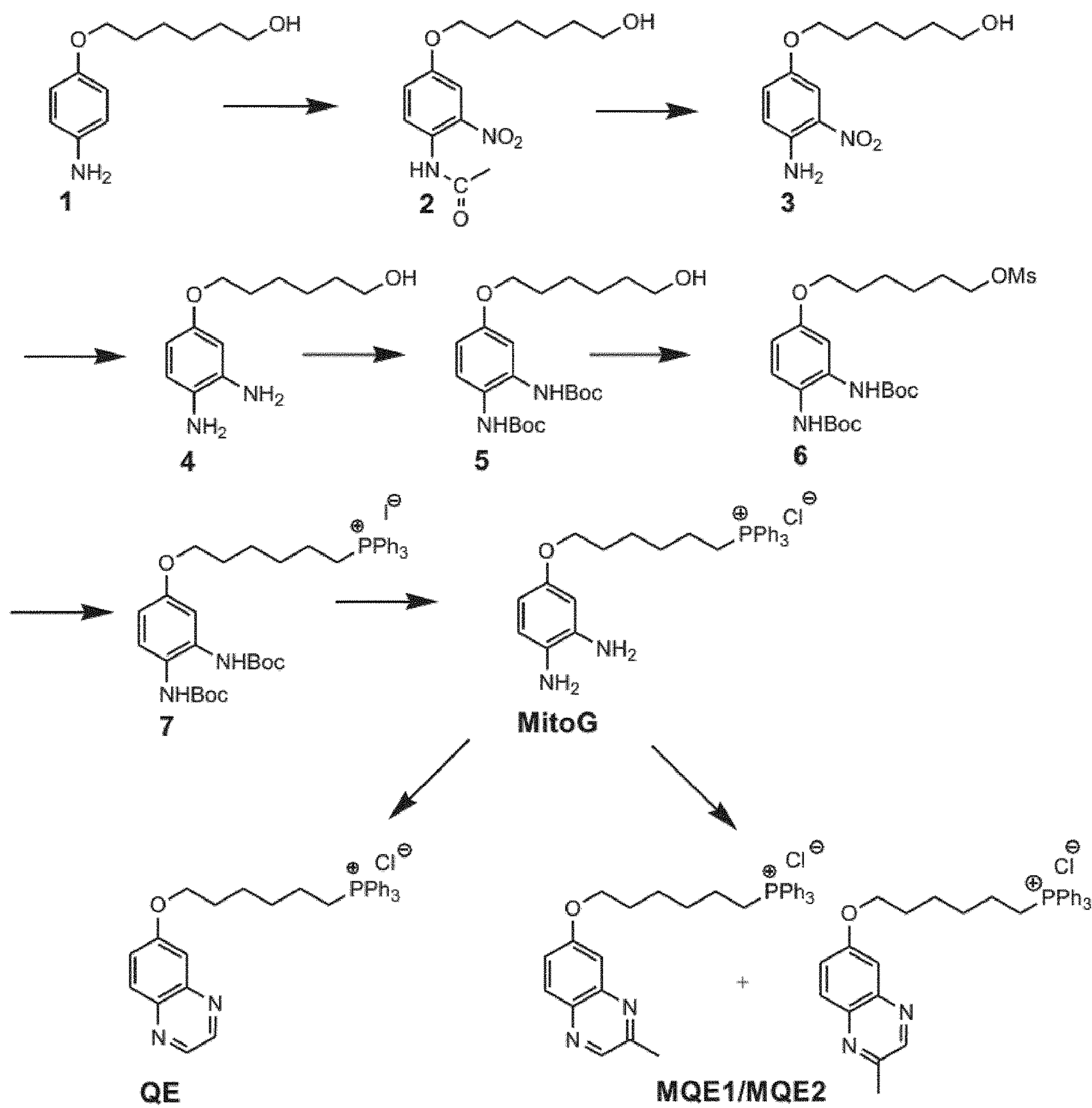
FIG. 2. shows the syntheses of MitoG, MQE and QE.

A schematic of the syntheses of MitoG, quinoxaline ether (QE) and the methylquinoxaline ethers 1 and 2 (MQE1/MQE2) is shown in FIG. 2. In summary, 6-(4-aminophenoxy)hexanol (1) was synthesized using the reported method [32]. Nitration of 1 was achieved as described [33] and involved conversion of 1 to the acetamide followed by nitration with concentrated nitric acid to give 2. Deprotection then gave the nitroaniline (3) in 48% overall yield from 1. The basic o-phenylenediamine skeleton was obtained by catalytic hydrogenation of the nitroaniline 3 over palladium on carbon. The air and light sensitive diamine (4) was immediately protected with tert-butyloxycarbonyl (Boc) groups by treatment with di-tert-butyldicarbonate in tetrahydrofuran [34]. The primary alcohol in 5 was mesylated to give 6 then converted to the phosphonium functional group by reaction with triphenylphosphine and sodium iodide in acetonitrile. The product 7 was obtained by precipitation from ether and column chromatography to give a white solid in 80% yield. In order to obtain a robust analytical sample, anion exchange to the tetraphenylborate was carried out by treatment of 7 with sodium tetraphenylborate in dichloromethane. Deprotection of the amino groups to give MitoG was accomplished by treatment of 7 in 1,4-dioxane with 9.8 M hydrochloric acid. MitoG was then reacted with either glyoxal to give the quinoxaline QE, or with methyl glyoxal to give the two methylquinoxaline products, MQE1 and MQE2, which were formed in a ratio of 10:1 (by $^{1}$H NMR) although they gave a single HPLC peak. Data are quoted for the major isomer.

N-(4-(6-Hydroxy hexyloxy)-2-nitrophenyl)acetamide (2)

To a solution of 6-(4-aminophenoxy)hexan-1-ol 1 (2.12 g, 10.0 mmol) in glacial acetic acid (3.20 mL) and water (2.40 mL) with ice (3.70 g) at 0-5° C. was added acetic anhydride (1.20 mL) with rapid stirring. The resulting crystalline mixture was dissolved by heating in a water bath. The reaction mixture was then cooled to about 45° C. before the addition of concentrated nitric acid (1.10 mL) with stirring. The reaction mixture was heated at 65° C. for 10 min, cooled to room temperature, placed in an ice bath for 18 h, diluted with water and extracted into dichloromethane. The organic phase was dried ($MgSO_4$) and evaporated in vacuo to give a mixture of 2, together with an intermediate acetate, as a yellow oil (2.98 g). Purification by column chromatography on silica gel eluting with diethyl ether gave 2 as a yellow crystalline solid (1.279 g, 43%).

$^{1}$H NMR (500 MHz, $CDCl_3$): δ 10.03 (1H, bs, NH), 8.61 (1H, d, J=8 Hz), 7.64 (1H, d, J=2 Hz), 7.21 (1H, dd, J=2, 8 Hz), 3.99 (2H, t, J=6 Hz, $CH_2O$), 3.67 (2H, t, J=6 Hz, $CH_2OH$), 2.26 (3H, s, Ac), 1.79-1.82 (2H, m), 1.58-1.64 (2H, m), 1.41-1.54 (4H, m), 1.30 (1H, bs, OH) ppm; $^{13}$C NMR (125 MHz, $CDCl_3$): δ 168.8, 154.5, 137.1, 128.4, 123.9, 123.8, 109.2, 68.7 ($CH_2O$), 62.9 ($CH_2OH$), 32.7, 29.0, 25.9, 25.6, 25.5 ppm; MS m/z found: 319.1261, calcd. for $C_{14}H_{20}N_2O_5.Na^+$, 319.1264.

6-(4-Amino-3-nitrophenoxy)hexan-1-ol (3)

Claisen's alkali (0.45 mL) was added to the total crude product from 2 (0.527 g, 1.78 mmol) and heated to 70° C. with stirring for 15 min. Hot water (0.45 mL) was then added to the reaction mixture with stirring and this was heated for another 15 min. The reaction mixture was cooled to 0-5° C. in an ice bath, diluted with water and extracted into dichloromethane. The organic phase was dried ($MgSO_4$) and evaporated in vacuo to give an orange/red solid (0.390 g). Purification by column chromatography on silica gel eluting with diethyl ether gave 3 as an orange/red solid (0.236 g, 52%).

$^{1}$H NMR (500 MHz, $CDCl_3$): δ 7.53 (1H, d, J=2 Hz), 7.06 (1H, dd, J=2, 8 Hz), 6.75 (1H, d, J=8 Hz), 5.88 (2H, bs, $NH_2$), 3.92 (2H, t, J=6 Hz, $CH_2O$), 3.66 (2H, bt, J=6 Hz, $CH_2OH$), 1.76-1.81 (2H, m, $CH_2CH_2O$), 1.58-1.65 (2H, m, $CH_2CH_2OH$), 1.40-1.52 (4H, m), 1.30 (1H, bs, OH); $^{13}$C NMR (125 MHz, $CDCl_3$): δ 150.3, 139.9, 131.6, 127.1, 120.1, 107.2, 68.7 ($CH_2O$), 62.9 ($CH_2OH$), 32.7, 29.1, 25.9, 25.6; MS m/z found: 277.1161, calcd. for $C_{12}H_{18}N_2O_4.Na^+$: 277.1159. Microanalysis found: C, 56.83; H, 6.94; N, 10.99; calcd. for $C_{12}H_{18}N_2O_4$: C, 56.68; H, 7.13; N, 11.02.

6-(3,4-Diaminophenoxy)hexan-1-ol (4)

Palladium on carbon (0.20 g) was added to a solution of the nitroaniline (3) (2.22 g, 8.7 mmol) in dry ethanol (200 mL) and the mixture stirred for 18 h under an atmosphere of hydrogen. The reaction mixture was filtered through Celite® and evaporated in vacuo to give 4 as a red solid (1.83 g, 93%). The crude product was used without further purification.

$^{1}$H NMR (500 MHz, $CDCl_3$): δ 6.62 (1H, d, J=8 Hz), 6.32 (1H, d, J=2 Hz), 6.25 (1H, dd, J=2, 8 Hz), 3.87 (2H, t, J=6 Hz, $CH_2O$), 3.65 (2H, t, J=6 Hz, $CH_2OH$), 1.72-1.77 (2H, m, $CH_2CH_2O$), 1.55-1.65 (2H, m, $CH_2CH_2OH$), 1.38-1.51 (4H, m); $^{13}$C NMR (125 MHz, $CDCl_3$): δ 154.0, 137.1, 127.3, 118.4, 105.1, 103.8, 68.3 ($CH_2O$), 63.0 ($CH_2OH$), 32.8, 29.4, 26.0, 25.6; MS m/z found: 225.1592, calcd. for $C_{12}H_{21}N_2O_2^+$, 225.1596; Microanalysis found: C, 64.15; H, 8.94, 12.29; calcd. for $C_{12}H_{20}N_2O_2$: C, 64.26; H, 8.99; N, 12.49.

tert-Butyl-4-(6-hydroxyhexyloxy)-1,2-phenylenedicarbamate (5)

Di-tert-butyldicarbonate (0.48 g, 2.2 mmol) was added to a solution of 4 (0.16 g, 0.73 mmol) in tetrahydrofuran (5 mL) and stirred under an atmosphere of argon at room temperature for 18 h. Sodium bicarbonate (0.31 g, 3.6 mmol) was added to the reaction mixture which was stirred for another 30 min. The reaction mixture was filtered and evaporated in vacuo to give a yellow oil (0.621 g). Purification by column chromatography on silica gel eluting with 1% triethylamine in diethyl ether gave 5 as a yellow oil (0.228 g, 74%).

$^1$H NMR (500 MHz, $CDCl_3$): δ 7.29 (1H, bs), 7.14 (1H, m), 6.91 (1H, bs, NH), 6.59 (1H, dd, J=2, 8 Hz), 6.35 (1H, bs, NH), 3.93 (2H, t, J=6 Hz, $CH_2O$), 3.63 (2H, t, J=6 Hz, $CH_2OH$), 1.72-1.78 (2H, m), 1.54-1.63 (2H, m), 1.50 (9H, s), 1.49 (9H, s), 1.36-1.47 (4H, m) ppm; $^{13}$C NMR (125 MHz, $CDCl_3$): δ 157.6 (C4), 154.6, 153.3, 133.6 (C2), 126.7 (C6), 121.0 (C1), 110.8 (C5), 108.4 (C3), 80.8, 80.7, 68.1 ($CH_2O$), 62.9 ($CH_2OH$), 32.7 ($CH_2CH_2O$), 29.2 ($CH_2CH_2OH$), 28.4, 28.3, 25.9, 25.5; MS m/z found: 447.2451, calcd. for $C_{22}H_{36}N_2O_6.Na^+$: 447.2466; Microanalysis found: C, 62.50; H, 8.86; N, 6.35; calcd. for $C_{22}H_{36}N_2O_6$: C, 62.24; H, 8.86; N, 6.35.

6-(3,4-Bis(tert-butoxycarbonylamino)phenoxy)hexylmethanesulfonate (6)

A solution of 5 (0.23 g, 0.53 mmol) and triethylamine (150 μL, 0.110 g, 1.06 mmol) was stirred in anhydrous dichloromethane (10 mL) at room temperature. Methanesulfonyl chloride (50 μL, 0.074 g, 0.64 mmol) was added and the reaction was stirred for 1 h. The reaction mixture was diluted with dichloromethane, washed with water and aqueous sodium bicarbonate, dried ($MgSO_4$) and evaporated in vacuo to give 6 as a yellow oil (0.213 g, 80%). The crude product was used without further purification.

$^1$H NMR (500 MHz, $CDCl_3$): δ 7.31 (1H, bs), 7.15 (1H, m), 6.89 (1H, bs, NH), 6.59 (1H, dd, J=2, 8 Hz), 6.29 (1H, bs, NH), 4.23 (2H, t, J=8 Hz, $CH_2OMs$), 3.94 (2H, t, J=6 Hz, $CH_2O$), 2.99 (3H, s, Ms), 1.74-1.80 (4H, m), 1.46-1.51 (22H, m) ppm; $^{13}$C NMR (125 MHz, $CDCl_3$): δ 157.6, 154.6, 153.3, 133.6, 126.8, 121.0, 110.8, 108.3, 80.8, 80.7, 70.0 ($CH_2OMs$), 67.9 ($CH_2O$), 37.4, 29.1, 29.0, 28.4, 28.3, 25.6, 25.3 ppm; MS m/z found: 525.2240, calcd. for $C_{23}H_{38}N_2O_8S.Na^+$: 525.2241.

(6-(3,4-Bis(tert-butoxycarbonylamino)phenoxy)hexyl)triphenylphosphonium iodide (7)

A solution of mesylate 6 (0.59 g, 1.17 mmol) and triphenylphosphine (0.34 g, 1.29 mmol) with sodium iodide (0.260 g, 1.76 mmol) in dry acetonitrile (100 mL) was heated to 80° C. with stirring for 48 h. The reaction mixture was cooled to room temperature and the white solid was removed by filtration and washed with acetonitrile. The solvent was then reduced to about 30 mL and ether (400 mL) added slowly with stirring to precipitate the product. The ether was decanted from the oily solid and the process was repeated. The oily solids were dried at <0.5 mm Hg for 1 h to give a yellow solid (0.680 g). Purification by column chromatography on silica gel eluting with 5 to 15% methanol in chloroform gave 7 as a white solid (0.585 g, 63%).

$^1$H NMR (500 MHz, $CD_2Cl_2$): δ 7.84-7.80 (3H, m, Ar), 7.73-7.67 (12H, m, Ar), 7.54 (1H, bs, NH), 7.25 (1H, bs), 7.19 (1H, d, J=8 Hz), 6.94 (1H, bs, NH), 6.55 (1H, dd, J=2, 8 Hz), 3.91 (2H, t, J=6 Hz, $CH_2O$), 3.31 (2H, m, $CH_2P$), 1.59-1.72 (6H, m), 1.26-1.47 (20H, m); $^{13}$C NMR (125 MHz, $CDCl_3$): δ 157.3, 154.8, 153.8, 135.6 (d, $J_{C4P}$=3 Hz, p-Ph), 133.9 (d, $J_{C2P}$=10 Hz, o-Ph), 130.9 (d, $J_{C3P}$=13 Hz, m-Ph), 126.9, 122.4, 118.5 (d, $J_{CP}$=86 Hz, i-Ph), 110.7, 109.0, 80.5, 80.4, 68.1 ($CH_2O$), 30.2 (d, $J_{C3P}$=16 Hz, $CH_2CH_2CH_2P$), 28.9, 28.4, 28.3, 25.6, 22.7 (d, $J_{C2P}$=4 Hz, $CH_2CH_2P$), 22.6 (d, $J_{CP}$=51 Hz, $CH_2P$); $^{31}$P NMR (162 MHz, $CD_2Cl_2$): δ 24.4 ppm; MS m/z found: 669.3506, calcd. for $C_{40}H_{50}N_2H_5P^+$: 669.3452;

A sample of the tetraphenylborate salt of 7 for analysis was prepared by anion exchange with sodium tetraphenylborate in dichloromethane. The product was recrystallised from ethanol at −78° C., filtered and dried in vacuo at 40° C. for 4 days to give (6-(3,4-bis(tert-butoxycarbonylamino)phenoxy)hexyl)triphenylphosphonium tetraphenylborate as white crystals.

Microanalysis found: C, 77.43; H, 7.35; N, 2.80; calcd. for $C_{64}H_{70}N_2O_5BP$: C, 77.72; H, 7.13; N, 2.83; MS m/z found: 669.3442, calcd. for $C_{40}H_{50}N_2H_5P^+$: 669.3452. found: 319.1680, calcd. for $C_{24}H_{20}B^-$: 319.1664. $^1$H and $^{31}$P NMR spectra were consistent with 7.

(6-(3,4-Bis(tert-butoxycarbonylamino)phenoxy)hexyl)-$D_{15}$-triphenylphosphonium iodide ($d_{15}$-7)

Similarly mesylate (6) (290 mg) with sodium iodide (110 mg) and $d_{15}$ labelled triphenylphosphine (100 mg) gave $d_{15}$-7 as an off white gum (0.274 g, 90%). HPLC 13.24 min 99+% pure. $^1$H NMR (500 MHz, $CDCl_3$): δ 7.25 (1H, bs), 7.16 (1H, bd, J=8 Hz), 6.96 (1H, bs, NH), 6.57 (1H, dd, J=2, 8 Hz), 6.38 (1H, bs, NH), 3.89 (2H, t, J=6 Hz, $CH_2O$), 3.74 (2H, m, $CH_2P$), 1.59-1.72 (6H, m), 1.55 (6H, s) and 1.38-1.48 (14H, m). MS m/z found: 684.396, calcd. for $C_{40}H_{35}D_{15}N_2O_5P^+$: 684.4393.

(6-(3,4-Diaminophenoxy)hexyl)triphenylphosphonium chloride (MitoG)

Hydrochloric acid (9.8 M, 1.0 mL) was added to a solution of 7 (0.050 g, 0.065 mmol) in 1,4-dioxane (1 mL) and stood at room temperature under argon for 1 h. The reaction mixture was concentrated under reduced pressure (<0.5 mmHg) to give MitoG as a pale yellow solid (0.035 g, 98%).

HPLC 8.9 min 95% pure, $^1$H NMR (500 MHz, $(CD_3)_2SO$): δ 7.86-7.90 (3H, m, Ar), 7.73-7.80 (12H, m, Ar), 6.39 (1H, d, J=8 Hz), 6.12 (1H, d, J=2 Hz), 5.92 (1H, dd, J=2, 8 Hz), 4.47 (4H, bs, $NH_2$), 3.70 (2H, t, J=6 Hz, $CH_2O$), 3.57 (2H, m, $CH_2P$), 1.45-1.58 (6H, m), 1.34-1.40 (2H, m); $^{13}$C NMR (125 MHz, $(CD_3)_2SO$): δ 151.6, 136.7, 134.8 (d, $J_{C4P}$=3 Hz, p-Ph), 133.5 (d, $J_{C2P}$=10 Hz, o-Ph), 130.2 (d, $J_{C3P}$=12 Hz, m-Ph), 127.8, 118.5 (d, $J_{CP}$=86 Hz, i-Ph), 115.5, 102.4, 101.9, 67.2 ($CH_2O$), 29.6 (d, $J_{C3P}$=17 Hz, $CH_2CH_2CH_2P$), 28.6, 24.8, 21.7 (d, $J_{C2P}$=4 Hz, $CH_2CH_2P$), 20.2 (d, $J_{CP}$=50 Hz, $CH_2P$) ppm; $^{31}$P NMR (162 MHz, $CD_2Cl_2$): δ 23.8 ppm; MS m/z found: 469.2404, calcd. for $C_{30}H_{34}N_2OP^+$: 469.2403.

(6-(3,4-Diaminophenoxy)hexyl)-$D_{15}$-triphenylphosphonium chloride ($d_{15}$-MitoG)

Similarly (6-(3,4-bis(tert-butoxycarbonylamino)phenoxy)hexyl)triphenylphosphonium iodide ($d_{15}$-7) (0.021 g, 0.026 mmol) gave $d_{15}$-MitoG as a pale yellow solid. The crude product was used without further purification.

HPLC: 9.0 min 89% pure. MS m/z found: 484.3332, calcd. for $C_{30}H_{19}D_{15}N_2OP^+$: 484.3345.

(6-(6-Quinoxalinyloxy)hexyl)triphenylphosphonium trifluoroacetate (QE)

Triethylamine (50 μL) was added to a stirred solution of 8 (0.007 g, 14 μmol) in ethanol (96%, 1 mL) under argon at room temperature. After 5 min a solution of glyoxal (40%, 50 μL) in ethanol (96%, 0.5 mL) was added and the mixture stirred under argon for 2 h. The reaction mixture was evaporated in vacuo to give the product as a pale yellow gum. Purification by column chromatography on an SPE C18 silica column (10 g), eluting stepwise with 10 to 100% acetonitrile in water (0.1% TFA) gave QE in the 50% fraction as a brown gum (5 mg, 68%).

HPLC 11.2 min 99+% pure; $^1$H NMR (500 MHz, $CD_2Cl_2$): δ 8.72 (1H, d, J=2 Hz), 8.68 (1H, d, J=2 Hz), 7.96 (1H, d, J=8 Hz), 7.77-7.84 (3H, m, Ar), 7.69-7.76 (12H, m, Ar), 7.40 (1H, dd, J=2, 8 Hz), 7.38 (1H, d, J=2 Hz), 4.12 (2H, t, J=6 Hz, $CH_2O$), 3.48 (2H, m, $CH_2P$), 1.85 (2H, m), 1.72 (4H, m), 1.56 (2H, m) ppm; $^{13}$C NMR (125 MHz, $CD_2Cl_2$): δ 160.6, 144.9, 144.6, 142.7, 139.6, 135.6 (d, $J_{C4P}$=3 Hz, p-Ph), 134.0 (d, $J_{C2P}$=10 Hz, o-Ph), 130.9 (d, $J_{C3P}$=13 Hz, m-Ph), 130.7, 123.9, 118.4 (d, $J_{CP}$=86 Hz, i-Ph), 107.5, 68.8 ($CH_2O$), 30.6 (d, $J_{C3P}$=16 Hz, $CH_2CH_2CH_2P$), 29.0, 25.9, 23.5 (d, $J_{CP}$=51 Hz, $CH_2P$), 22.9 (d, $J_{C2P}$=4 Hz, $CH_2CH_2P$) ppm; $^{31}$P NMR (162 MHz, $CD_2Cl_2$): δ 23.8 ppm; MS m/z found: 491.2238, calcd. for $C_{32}H_{32}N_2OP^+$: 491.2247.

6-(6-Quinoxalinyloxy)hexyl)-$d_{15}$-triphenylphosphonium trifluoroacetate ($d_{15}$-QE)

Similarly diamine ($d_{15}$-MitoG) (0.036 g, 71 μmol) with glyoxal (40%, 200 μL) gave $d_{15}$-QE in the 50% fraction as a brown gum (14 mg, 37%).

HPLC 11.0 min 99+% pure; $^1$H NMR (500 MHz, $CDCl_3$): δ 8.79 (1H, d, J=2 Hz), 8.74 (1H, d, J=2 Hz), 8.05 (1H, d, J=8 Hz), 7.43 (1H, dd, J=2, 8 Hz), 7.38 (1H, d, J=2 Hz), 4.12 (2H, t, J=6 Hz, $CH_2O$), 3.38 (2H, m, $CH_2P$), 1.82 (2H, m), 1.66 (4H, m), 1.53 (2H, m) ppm; MS m/z found: 506.3201, calcd. for $C_{32}H_{17}D_{15}N_2OP^+$: 506.3188.

(6-(6-(2-Methyl-quinoxalinyloxy))hexyl)triphenylphosphonium trifluoroacetate (MQE1/MQE2)

Similarly reaction of MitoG (0.007 g, 14 μmol) with methylglyoxal (40%, 50 μL) gave the methyl quinoxalines (MQE1/MQE2) in the 50% fraction as a brown gum (5 mg, 68%).

HPLC: 11.1 min. $^1$H NMR (500 MHz, $CD_2Cl_2$): δ 8.78 (1H, s), 8.04 (1H, d, J=8 Hz), 7.77-7.84 (3H, m, Ar), 7.69-7.76 (12H, m, Ar), 7.55 (1H, d, J=2 Hz), 7.44 (1H, dd, J=2, 8 Hz), 4.16 (2H, t, J=6 Hz, $CH_2O$), 3.14 (2H, m, $CH_2P$), 2.83 (3H, s, C-Me), 1.88 (2H, m, $CH_2CH_2O$), 1.75 (2H, m), 1.67 (2H, m) and 1.58 (2H, m) ppm; $^{13}$C NMR (125 MHz, $CD_2Cl_2$): δ 161.91, 160.25 (q, $J_{CF}$=30 Hz, $CF_3CO$), 152.74, 143.20, 141.10, 137-43, 135.80 (d, $J_{C4P}$=3 Hz, p-Ph), 133.58 (d, $J_{C2P}$=10 Hz, o-Ph), 130.92 (d, $J_{C3P}$=13 Hz, m-Ph), 130.08, 123.83, 117.88 (d, $J_{CP}$=86 Hz, i-Ph), 116.21 (d, $J_{CF}$=230 Hz, $CF_3$) 105.01, 68.88 ($CH_2O$), 30.50 (d, $J_{C3P}$=16.0 Hz, $CH_2CH_2CH_2P$), 28.71, 25.58, 23.20 (d, $J_{CP}$=51 Hz, $CH_2P$), 22.69 (d, $J_{C2P}$=4 Hz, $CH_2CH_2P$), 21.06 (CMe) ppm; $^{31}$P NMR (162 MHz, $CD_2Cl_2$): δ 23.8 ppm. MS m/z found: 505.2419, calcd. for $C_{33}H_{34}N_2OP^+$: 505.2403.

(6-(6-(2-Methyl-quinoxalinyloxy))hexyl)-$d_{15}$-triphenylphosphonium trifluoroacetate ($d_{15}$-MQE1/MQE2)

Similarly $d_{15}$-MitoG (0.036 g, 71 μmol) with methylglyoxal (40%, 200 μL) gave $d_{15}$-MQE1/MQE2 in the 50% fraction as a brown gum (16 mg, 43%).

HPLC: 11.1 min 99%$^+$. $^1$H NMR (500 MHz, $CDCl_3$): δ 8.61 (2H, bs), 7.93 (1H, d, J=8 Hz), 7.32 (1H, dd, J=2, 8 Hz), 7.31 (1H, s), 4.07 (2H, t, J=6 Hz, $CH_2O$), 3.50 (2H, m, $CH_2O$), 2.75 (3H, s, CMe), 1.82 (2H, m, $CH_2CH_2O$), 1.66 (4H, m), 1.51 (2H, m) ppm; MS m/z found: 520.3366, calcd. for $C_{33}H_{19}D_{15}N_2OP^+$: 520.3345.

4-Hexyloxybenzene-1,2-diamine (HP)

The control compound (HP) was made as described above for MitoG. The compounds are related to the numbering scheme used in FIG. 2 by addition of the letter b.

Briefly, N-(4-(6-hexyloxy)-2-nitrophenyl)acetamide (2b) [62] was made from the amine 4-(hexyloxy)aniline 1b [32](1.57 g, 8.12 mmol) and gave 2b as a yellow oil (2.05 g). Purification by column chromatography on silica gel eluting with dichloromethane/diethyl ether gave 2b as a yellow solid (1.56 g, 75%). $^1$H NMR (400 MHz, $CDCl_3$): δ 10.04 (1H, bs), 8.62 (1H, d, J=8 Hz), 7.65 (1H, d, J=2 Hz), 7.22 (1H, dd, J=2, 8 Hz), 3.99 (2H, t, J=6 Hz, $CH_2O$), 2.26 (3H, s, Ac), 1.80 (2H, m, $CH_2CH_2O$), 1.46 (2H, m), 1.35 (4H, m) and 0.91 (3H, t, J=6 Hz, $CH_3$) ppm. Reaction of 2b (0.42 g, 1.5 mmol) gave then 4-(hexyloxy)-2-nitroaniline 3b then 4-hexyloxy-1,2-phenylenediamine 4b [63] as a red solid (0.224 g, 72%). This was used directly in the following reaction. For this the diamine 4b (0.34 g, 1.5 mmol) gave 3,4-bis tert-butyl-4-(hexyloxy)-1,2-phenylenedicarbamate 5b as a yellow oil (0.430 g, 71%). HPLC: 17.7 min>99% pure. $^1$H NMR (500 MHz, $CDCl_3$): δ 7.31 (1H, bs), 7.16 (1H, m), 6.84 (1H, bs, NH), 6.62 (1H, dd, J=2, 8 Hz), 6.25 (1H, bs, NH), 3.93 (2H, t, J=6 Hz, $CH_2O$), 1.75 (2H, m, $CH_2CH_2O$), 1.52 (9H, s), 1.50 (9H, s), 1.46 (2H, m), 1.33 (4H, m) and 0.90 (3H, t, J=6 Hz, $CH_3$); MS m/z found: 407.2618, calcd. for $C_{22}H_{35}N_2O_5^-$: 407.2546.

To make 4-hexyloxybenzene-1,2-diamine (HP) 5b (0.022 g, 0.054 mmol) was reacted with hydrochloric acid to give HP as a pale yellow solid. HPLC: 9.67 min>99% pure.

$^1$H NMR (500 MHz, $(CD_3)_2SO$): δ 7.19 (1H, d, J=8 Hz), 6.54 (1H, d, J=2 Hz), 6.37 (1H, dd, J=2, 8 Hz), 5.60 (4H, bs, $NH_2$), 3.95 (2H, t, J=6 Hz, $CH_2O$), 1.79 (2H, m, $CH_2CH_2O$), 1.50 (2H, m), 1.41 (4H, m), 1.51 (3H, t, J=6 Hz, $CH_3$) ppm. $^{13}$C NMR (125 MHz, $(CD_3)_2SO$): δ 159.24, 142.83, 125.17, 111.50, 104.30, 103.01, 67.87 ($CH_2O$), 31.44, 29.04, 25.61, 22.52 and 14.36 ($CH_3$) ppm; MS m/z found: 209.1701, calcd. for $C_{12}H_{21}N_2O^+$: 209.1654.

[3-(3,4'-Diaminobenzoylamino)-prop-1-yl]triphenylphosphonium m esylate (MitoG-amide)

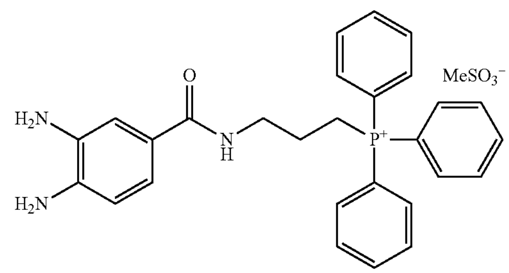 [SMILES: "MeSO3-" ; Nc1ccc(C(=O)NCCC[P+](c2ccccc2)(c2ccccc2)c2ccccc2)cc1N]

A solution of (3-aminopropyl)triphenylphosphonium iodide (1.34 g, 3.0 mmol), 2,4-diaminobenzoic acid (445 mg, 2.9 mmol), and diisopropylcarbodiimide (400 μl, 2.6 mmol) in dry MeCN (10 mL) was stirred at 35° C. under Ar for 48 h. After this, the precipitate was washed with MeCN (3×10 mL). The solid was collected and the residual solvent was removed under high vacuum. The resulting brown solid (1.25 g) was recrystallized twice from ethanol to give the iodide salt as a brown powder (790 mg, 53%). A sample of the iodide was dissolved in MeOH—$H_2O$ (50:50) and passed trough an ion exchange column (Amberlite IRA-400, mesylate counterion) twice. The solvent was removed under vacuum yielding the phosphonium mesylate as an amorphous brown solid (238 mg, 44%). $\delta_H$ ($CD_3OD$, 400 MHz): 7.92-7.87 (m, 3×p-H $PPh_3$), 7.82-7.71 (12H, m, 6×o-H $PPh_3$, 6×m-H $PPh_3$), 7.21 (1H, d, J=1.9 Hz, H-2'), 7.14 (1H, dd, J=8.1, 2.0 Hz, H-6'), 6.68 (1H, d, J=8.1 Hz, H-5'), 3.53 (2H, t, J=6.4 Hz, $NCH_2$), 3.50-3.44 (2H, m, $PCH_2$), 2.70 (3H, s, $CH_3SO_3$) 2.02-1.92 (2H, m, $CH_2CH_2CH_2$). $\delta_C$ ($CD_3OD$, 125 MHz): 170.99 (C), 141.14 (C), 136.34 (d, J=4 Hz, CH), 134.80 (d, J=10 Hz, CH), 131.59 (d, J=12 Hz, CH), 124.42 (C), 120.52 (CH), 119.78 (d, J=86 Hz, C), 116.44 (CH), 115.55 (CH), 40.81 (d, J=18 Hz, $CH_2$), 39.55 ($CH_3$), 24.03 (d, J=4 Hz, $CH_2$), 20.68 (d, J=52 Hz, $CH_2$) (one C presumably coincident with another signal).

The glyoxalase I inhibitor, bromobenzyl glutathione cyclopentyl diester, was synthesised by alkylation of glutathione [35], followed by standard Boc-protection, coupling with cyclopentanol using 2-(1H-benzotriazole-1-yl)-1,1,3,3-tetramethyluronium tetrafluoroborate [36], trifluoroacetic acid (TFA) removal of the Boc group and treatment with sodium bicarbonate to give the free base. Other reagents were obtained from Sigma-Aldrich, unless otherwise stated. $^1H$, $^{13}C$ and $^{31}P$ spectra were acquired on Varian INOVA-400 or Varian INOVA-500 spectrometers. Chemical shifts are reported downfield from TMS, relative to the solvent residual signal. For the chemical synthesis components of this work, high resolution mass spectra were recorded on a Bruker microTOF electrospray mass spectrometer and HPLC analysis was carried out on an Agilent HP1100: Column Phenomenex Prodigy 250×3 mm, gradient elution 10% acetonitrile/water (0.1% TFA) to 100% acetonitrile over 12.5 min at 0.5 mL min-1 with detection at 210 and 254 nm.

Assessment of Compound Properties

TPP-conjugated compounds were made up as 10 mM stock solutions in DMSO, flushed with argon and stored as aliquots at −20° C. UV/Visible spectra and kinetic analyses were done using a Shimadzu UV-2501PC spectrophotometer in a 1 ml-cuvette containing KCl buffer [120 mM KCl, 10 mM HEPES and 1 mM EGTA, pH 7.2 (KOH)]. The molar extinction coefficients were calculated from the absorbance at maximal absorption ($\lambda_{max}$) for the compounds for solutions of known concentration. Reaction rates between MitoG and 1,2-dicarbonyls were determined from the initial linear slope over the first 30 s at the $\lambda_{max}$ for the formation of the relevant quinoxaline. Fluorescence spectra were obtained in 2.5 ml KCl buffer using a Shimadzu RF-301PC fluorimeter with slit widths of 3 nm. Kinetic assays used excitation and emission wavelengths of 344 and 433 nm, respectively, emission spectra used an excitation wavelength of 344 nm and excitation spectra used an emission wavelength of 433 nm.

RP-HPLC was performed using a Gilson 321 pump with a C18 column (Jupiter 300 Å, Phenomenex) with a Widepore C18 guard column (Phenomenex). Samples (1 ml) were injected through a 0.22 μm PVDF filter (Millex, Millipore). HPLC buffer A [0.1% TFA in water] and HPLC buffer B (90% acetonitrile and 0.1% TFA) were used and a gradient was run at 1 ml/min at room temperature as follows: 0-2 min—5% B; 2-17 min—5-100% B; 17-19 min—100% B; 19-22 min—100-5% B. Peaks were detected by absorbance at 220 nm (UV/Vis 151, Gilson) and by fluorescence (excitation and emission wavelengths of 344 and 433 nm; RF-10AXL, Shimadzu). Partition coefficients between PBS and octan-1-ol were determined as previously described [37].

Mitochondrial Preparation and Incubations

Rat liver mitochondria (RLM) were prepared at 4° C. in STE buffer [250 mM sucrose, 5 mM Tris and 1 mM EGTA, pH 7.4 (HCl)] by homogenisation and differential centrifugation. Protein concentration was determined using the biuret assay relative to bovine serum albumin (BSA) and was typically 40-60 mg/ml. A Clark-type oxygen electrode (Rank Brothers, Bottisham, Cambridge, UK) connected to a Powerlab 2/20 data acquisition system (AD Instruments, Australia) was used to measure respiration rates and was calibrated with air-saturated water (210 nmol $O_2$/ml at 37° C.). RLM (2 mg protein/ml) were suspended in 120 mM KCl, 10 mM HEPES, 1 mM EGTA, 1 mM $MgCl_2$ and 5 mM $KH_2PO_4$, pH 7.2 (KOH) in a thermostatted 1 ml-electrode chamber with stirring. MitoG was then added and after 5 min glutamate and malate (5 mM of each) were added, followed 3 min later by 400 μM ADP. Oxygen consumption rates were determined from the slopes using Chart v5.5.6. for Mac (AD Instruments, Australia). An electrode selective for the TPP moiety of MitoG was constructed and used as previously described [38].

Cell Culture

All cells were incubated at 37° C. in a humidified atmosphere of 95% air and 5% $CO_2$ and culture media used were supplemented with 10% (v/v) fetal calf serum (FCS), 100 U/ml penicillin and 100 μg/ml streptomycin. $C_2C_{12}$ cells (mouse myoblast cell line; European Collection of Animal Cell Cultures) were cultured in low glucose (1000 mg/l D-glucose) Dulbecco's modified Eagle's medium (DMEM; Invitrogen). Cells were maintained at sub-confluence (<80%) to prevent differentiation. BAECs (Bovine Aortic Endothelial Cells; Cell Applications Inc, San Diego, Calif.) were maintained in α-minimum essential medium (αMEM; Invitrogen) containing 5 mM D-glucose. All culture flasks and assay plates used for experiments were pre-coated with fibronectin ((25 μg/ml: Sigma) in Hank's balanced salt solution (HBSS; Cell Applications) at 1-4 μg fibronectin/$cm^2$. After 1 h at RT excess coating solution was removed, and flasks and plates were then seeded with cells for experiments. BAECs were used for experiments at passages 4-6.

To assess cell viability, C2C12 cells or BAECs were seeded at a density of 10,000 cells/well and 40,000 cells/well, respectively, in 96-well plates. After an overnight incubation, the medium was replaced with fresh media containing test compounds and incubated for 24 h. To determine cell survival, cells were washed twice with media, then fresh medium (100 μl per well) was added and mixed with 20 μl [3-(4,5-dimethylthiazol-2-yl)-5-(3-carboxymethoxyphenyl)-2-(4-sulfophenyl)-2H-tetrazolium]/phenazine methosulphate (MTS/PMS) (Promega, USA). After 2 h absorbance was read at 490 nm in a plate reader (SpectraMax Plus 384, Molecular Devices). All treatments were conducted in triplicate wells.

The Seahorse XF24 extracellular flux analyser was used to assess cellular oxygen consumption rate (OCR) [39-41]. Cells (40,000 BAECs/well) were cultured and subjected to experimental treatment in Seahorse XF24 V7 assay plates that were coated with fibronectin as described above. OCR was determined as follows: cells were washed twice in assay medium [4.15 g/l DMEM base, 1.85 g/l NaCl, ix glutamax (Invitrogen), 1 mM sodium pyruvate, 5 mM D-glucose, 15 mg/l phenol red, 20 mM HEPES and 0.4% (v/v) FCS, pH 7.4] and incubated in 630 μl assay medium for 1 h at 37° C.

in air. After 20 min equilibration basal OCR was determined and after 3 h incubation with MitoG sequential injections of oligomycin (1 μg/ml), FCCP (2 μM) and rotenone/antimycin A (4 μg/ml and 5 μM, respectively). OCRs were normalized to cell number as measured using the sulphorhodamine B (SRB) assay as follows: cells were fixed (200 μl 5% trichloroacetic acid at 4° C. for 1 h), washes with water (×3), stained for 20 min with 50 μl 0.4% (w/v) SRB in 1% (v/v) acetic acid, washed (3×1% acetic acid) and the incorporated SRB dye solubilised in 100 μl 10 mM Tris base for 5 min. Then 50 μl of each sample was transferred in duplicate to a 96-well plate, mixed with 50 μl 10 mM unbuffered Tris base and absorbance was read at 565 nm in a plate reader (SpectraMax Plus 384, Molecular Devices). A standard curve was constructed by seeding known number of cells in quadruplicate wells and fixing and staining them in parallel with sample wells. To calculate the proportion of oxygen consumption attributable to proton leak and reserve capacity, OCRs following injection of oligomycin, FCCP and rotenone/antimycin A were expressed as a percentage of the total basal OCR [42] [40].

To assess total methylglyoxal formation in cells by RP-HPLC, the cell layers were washed in PBS (1 ml), scraped into 1.5 ml PBS and pelleted by centrifugation (16,000 g for 2 min). The cell pellet was re-suspended in 500 μl KCl buffer, 500 μl 0.1% formic acid was added, protein was pelleted by centrifugation as above, and the supernatant collected. Methylglyoxal was then derivatized to 2-methylquinoxaline by addition 100 μM o-phenylenediamine followed by incubation at 37° C. for 4 h. Samples were dried under vacuum and assessed for 2-methylquinoxaline as previously described [28]. Briefly, dried samples were re-suspended in 1 ml HPLC buffer [68% (v/v) 10 mM $KH_2PO_4$, pH 2.5 and 32% acetonitrile], filtered (0.22 μm PVDF; Millex, Millipore) and separated by isocratic RP-HPLC in the HPLC buffer above at a flow rate of 2 ml/min at room temperature using a Gilson 321 pump with a C18 column (Jupiter 300 Å, Phenomenex) and a Widepore C18 guard column (Phenomenex). Peaks were detected fluorometrically (excitation and emission wavelengths of 352 and 385 nm, respectively; RF-10AXL, Shimadzu).

For LC-MS/MS analysis of MitoG reaction products cells were incubated in T25 flasks (Nunc) with 2 μM MitoG at 37° C. Cell monolayers were washed (1 ml PBS), scraped into 1.5 ml PBS and pelleted by centrifugation (16,000 g for 2 min). The pellet was re-suspended in 250 μl 100% acetonitrile/0.1% spiked with deuterated internal standards (ISs) (100 μmol each of $d_{15}$-MQE and $d_{15}$-QE), vortexed and centrifuged (2×16,000 g for 15 min). Samples were dried under vacuum (Savant SpeedVac), re-suspended in 100 μl 20% acetonitrile/0.1% formic acid, vortexed, centrifuged (16,000 g for 10 min), transferred to silanised autosampler vials [Chromacol #1.5HRRV(S)], flushed and sealed under argon and then stored at −80° C. until LC-MS/MS analysis. Where specified, cells were subjected to acute glycaemia treatment and were incubated either in low glucose (5 mM D-glucose), high glucose (30 mM D-glucose), or in osmotic control medium (5 mM D-glucose+25 mM L-glucose) for 4 h.

Mouse Experiments

The Akita mouse model of type I diabetes ($Ins2^{+/-AkitaJ}$) [43-45] was assessed at the University of Alabama, USA. All procedures were performed in accordance with "The Guide for the Care and Use of Laboratory Animals", and were approved by the Institutional Animal Care and Use Committee at the University of Alabama at Birmingham. Male $Ins2^{+/-AkitaJ}$ and wild type (C57BL/6) mice (4-8 weeks old) from Jackson Laboratory (Bar Harbor, Me., USA) were maintained on laboratory chow and water ad libitum until 14 weeks old when they were used for experiments. For this MitoG (100 nmol in 100 μl saline) was administered by tail vein injection. After 4-6 h the mice were killed and urine samples taken and snap frozen for subsequent analysis of MQE/QE content. Blood glucose levels were measured using an Accu-Chek Advantage blood glucose meter (Roche Diagnostics). Urine creatinine levels were determined at the Core Biochemical Assay Laboratory (Addenbrooke's Hospital, Cambridge, UK). To extract MQE and QE, 20 μl urine was mixed with 500 μl 60% acetonitrile/0.1% formic acid and incubated on ice for 30 min. The extracts were then spiked with deuterated ISs (100 pmol each of $d_{15}$-MQE and $d_{15}$-QE), vortexed for 30 sec and incubated on ice for 30 min with vortexing every 10 min and then centrifuged (16,000 g for 10 min). The supernatants were collected, filtered (0.22 m PVDF, Millex, Millipore) and dried under vacuum (Savant SpeedVac). The dried samples were re-suspended in 150 μl 20% acetonitrile/0.1% formic acid by vortexing for 5 min, followed by centrifugation at 16,000 g for 10 min. Samples were then transferred to silanised autosampler vials [Chromacol #1.5HRRV(S)], flushed and sealed under argon, and stored at −80° C. until LC-MS/MS analysis.

LC-MS/MS Analysis

The MS fragmentation patterns of TPP compounds were determined by direct infusion of compounds [1 μM in 20% acetonitrile (v/v)] at 2 μl/min into a triple quadrupole mass spectrometer (Waters Quattro Ultima). Electrospray ionisation in positive ion mode was used with the following settings: source spray voltage—3 kV; cone voltage—100 V; ion source temperature—80° C.; collision energy—50V. Nitrogen and argon were used as the curtain and collision gases, respectively.

LC-MS/MS analyses were carried out using a triple quadrupole mass spectrometer (Waters Xevo TQ-S) with an I-class Aquity LC system (Waters) attached. Samples were kept at 4° C. prior to injection by the autosampler of 10 μl into a 15 μl flow-through needle and RP-HPLC at 30° C. using a Luna 5 Phenyl-Hexyl column (1×50 mm, 5 μm; Phenomenex) with a Phenyl-Hexyl guard column (2×4 mm; Phenomenex). Buffers used were MS buffer A [0.1% (v/v) formic acid in water] and MS buffer B [95% acetonitrile/0.1% formic acid (both v/v)]. A gradient was run at 50 l/min as follows: 0-2 min—5% B; 2-3 min—5-25% B; 3-5 min—25-75% B; 5-7 min—75-100% B; 7-10 min—100% B; 10-12 min—100-5% B; 12-20 min—5% B. Eluant was diverted to waste from the mass spectrometer at 0-5 min and 16-20 min acquisition time using an in-line divert valve. For MS analysis, electrospray ionization in positive ion mode was used: source spray voltage—2.5 kV; cone voltage—25 V; ion source temperature −100° C.; collision energy—38 V. Nitrogen and argon were used as the curtain and the collision gases respectively. Multiple reaction monitoring in positive ion mode was used for compound detection. Transitions used for quantification were as follows: MQE, 506>262; $d_{15}$-MQE, 521>277; QE, 492>262 and $d_{15}$-QE, 507>277. For each experiment standard curves were prepared using known amounts of MQE and QE, which were spiked with IS and extracted in parallel with the samples. Standards and samples were quantified using MassLynx 4.1 software to determine the peak area for MQE, QE and ISs, and the standard curves used to determine the amount of MQE and QE present in samples.

Statistics

Data analysis was performed with R software environment for statistical computing and graphics (R Foundation for Statistical Computing, Wien, Austria). All data were analyzed using t-tests or one-way analysis of variance (ANOVA) followed by post-hoc Dunnett's test as appropriate, and represented as mean±standard error of mean (S.E.). P-values equal to or less than 0.05 were taken to be statistically significant.

Results and Discussion

Synthesis and Characterization of MitoG and its Reaction Products

Figure 3:
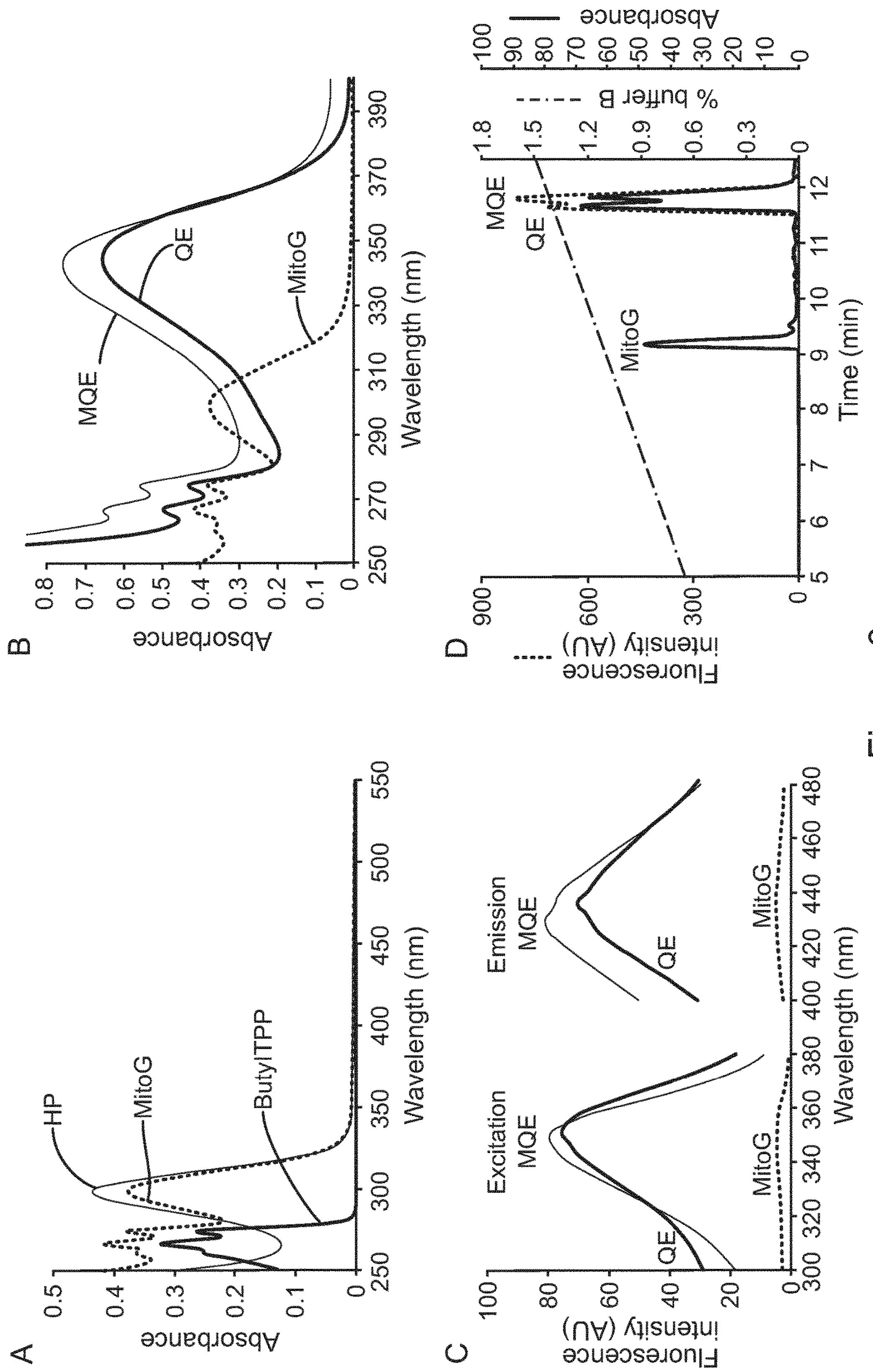
FIG. 3. shows the in vitro characterization of MitoG, MQE and QE. (A) Ultra Violet/Visible (UV/V) is scanning spectra of 100 μM MitoG shows the characteristic of its component TPP and 4-hexyloxyphenylene-1,2-diamine (HP) moieties. (B) UV/Vis scanning spectra of 100 μM MitoG, MQE and QE. (C) Fluorescent excitation spectra (emission 433 nm) and emission spectra (excitation 344 nm) of 10 μM MitoG, MQE and QE. MitoG was not fluorescent. MQE and QE had peak excitation and emission wavelengths of 344 nm and 433 nm, respectively. (D) Reverse Phase-High Performance Liquid Chromatography (RP-HPLC) profile of 10 nmol each of MitoG, MQE and QE. Absorbance (red) at 220 nm, fluorescence (blue) was observed at excitation and emission wavelengths of 344 nm and 433 nm, respectively. (E) UV/Vis scanning spectra of 100 μM MitoG and 1 mM methylglyoxal or glyoxal in KCl buffer after incubation at 37° C. for 2 h. (F) Fluorescent excitation and emission spectra of 10 μM MitoG and 20 μM methylglyoxal, or of 20 μM MitoG and 40 μM glyoxal, in KCl buffer after incubation at 37° C. for 2 h. (G) MitoG (5 mM) and 10 mM methylglyoxal were incubated in 10 μl KCl buffer at 37° C. for 2 h, then 1 μl mixture was assessed by RP-HPLC. (H) The identity of the product peak was confirmed by spiking the reaction mixture with 10 nmol MQE standard. Experiments with glyoxal gave similar results (data not shown).
Figure 3:
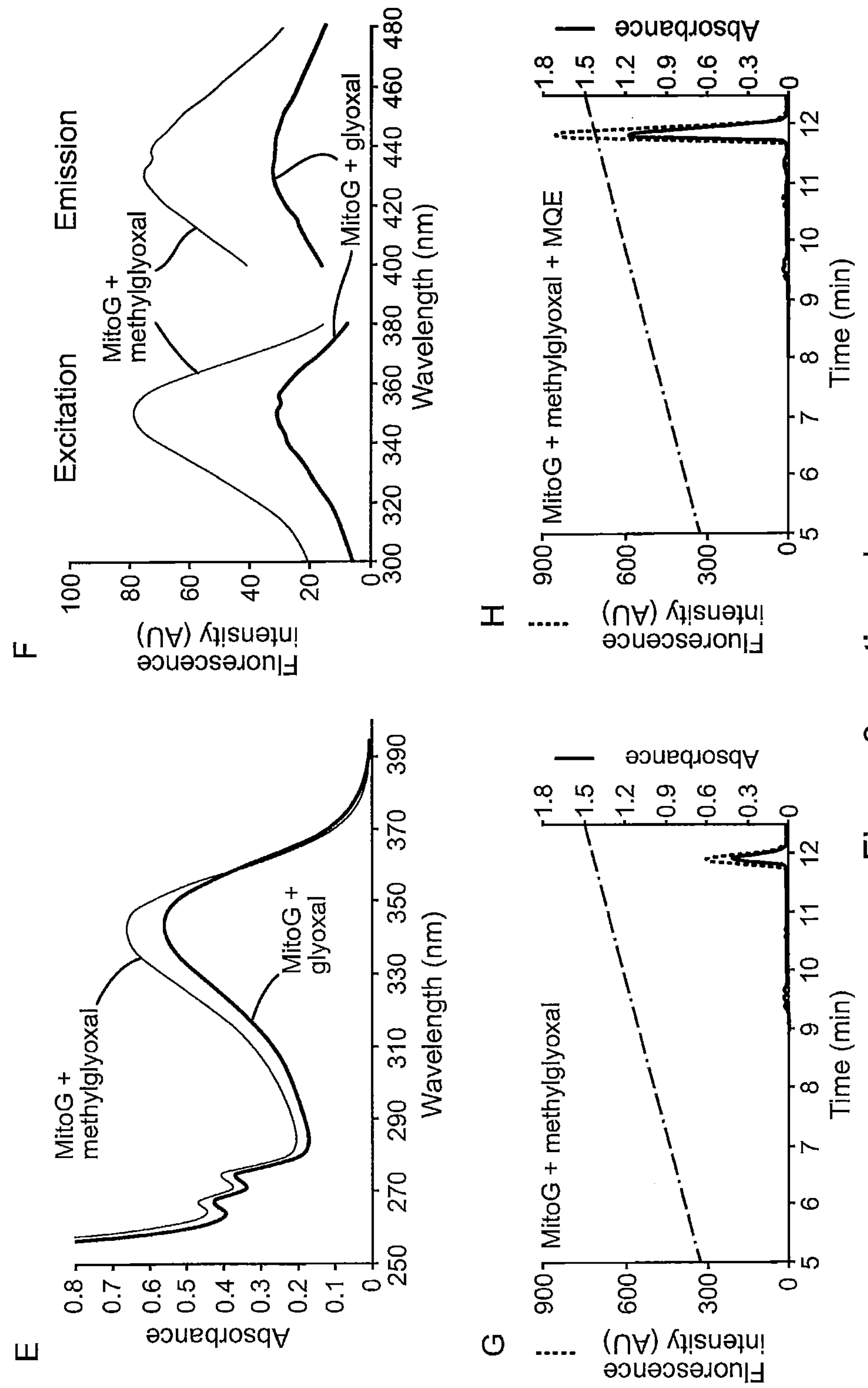

The syntheses of MitoG, its predicted quinoxaline products upon reaction with methylglyoxal and glyoxal, and their deuterated versions are summarized in FIG. 2. The UV/Vis absorption spectra of MitoG and its component TPP and phenylenediamine moieties are shown in FIG. 3A. As expected, the spectrum of MitoG was a summation of those of the phenylenediamine, hexyloxyphenylenediamine (HP), and a simple alkylTPP salt. As o-phenylenediamine undergoes oxidative degradation [2], and since there was literature precedent for the additional reactivity of alkoxy-substituted phenylenediamines, the stability of MitoG by RP-HPLC was assessed and it was found that stock solutions were stable under storage at −20° C. To assess its stability under biologically-relevant conditions, decomposition of dilute solutions of MitoG at 37° C. was measured, and minimal loss by 4 h with significant loss by 24 h were observed, therefore MitoG is sufficiently stable for biological experiments lasting up to ~4 h.

Figure 1:
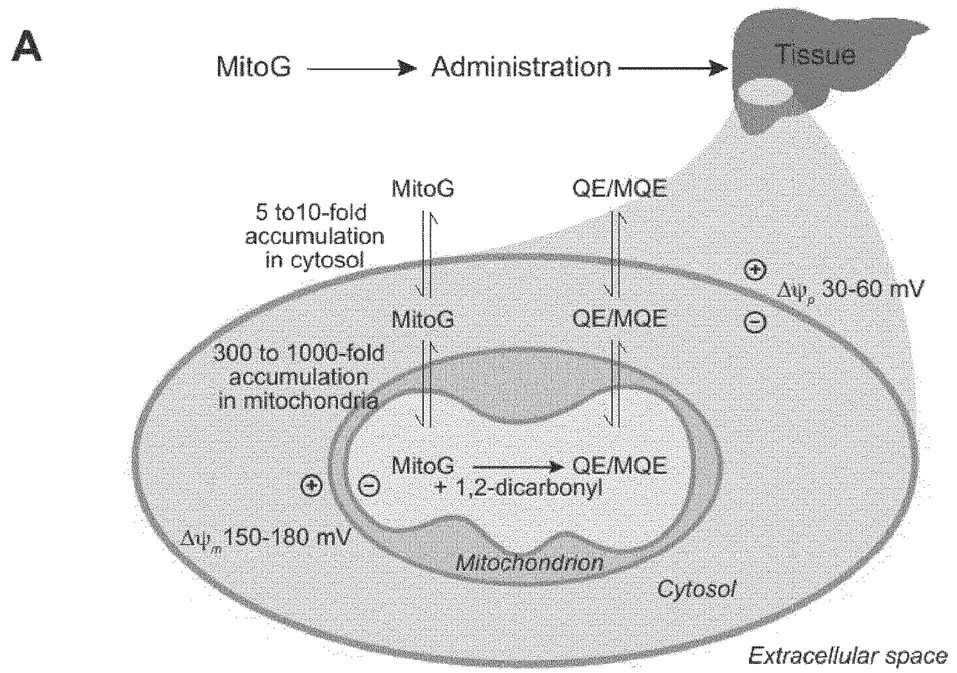
FIG. 1. shows the rationale and mechanism for the detection of intra-mitochondrial dicarbonyls. (A) MitoG, a mitochondria-targeted glyoxal and methylglyoxal trap, consists of a mitochondria-targeting TPP moiety and a phenylenediamine group that reacts with 1,2-dicarbonyls. The TPP moiety of MitoG leads to its uptake into tissues where it accumulates within mitochondria, driven by both the plasma and mitochondrial membrane potentials. (B) Within mitochondria MitoG can then react with glyoxal or methylglyoxal to form the quinoxaline products, quinoxaline ether (QE) and methylquinoxaline ether (MQE) (present as two isomers, MQE1 and MQE2). These products can then be quantified by LC-MS/MS relative to deuterated internal standards (ISs) to provide a measure of the amount of free glyoxal and methylglyoxal present within mitochondria in cells and in vivo.
Figure 1:
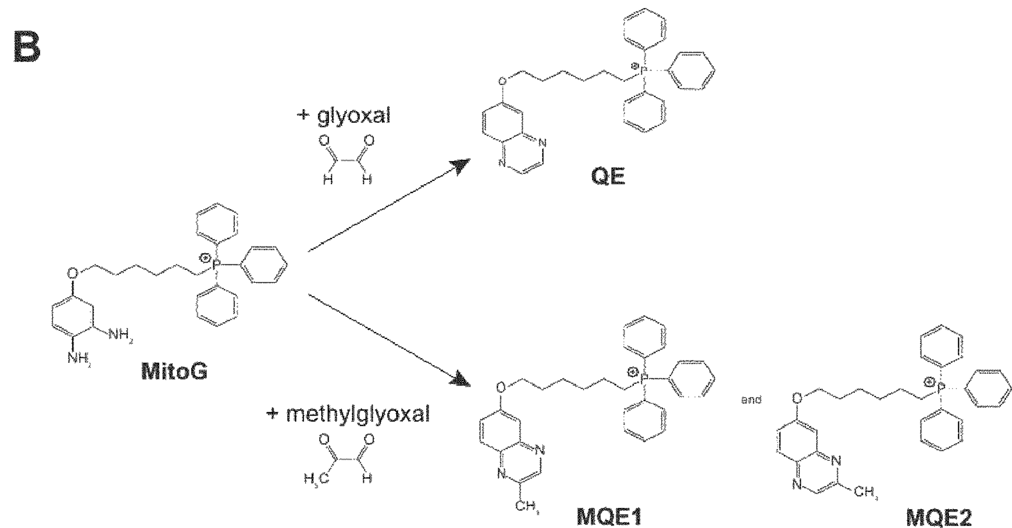

The expected products of the reaction of MitoG with methylglyoxal (MQE) and glyoxal (QE) were synthesized and have UV/Vis absorption spectra distinct from that of MitoG (FIG. 3B). Both QE and MQE were fluorescent, while MitoG was not (FIG. 3C). The three compounds were resolved by RP-HPLC (FIG. 3D) although the MQE regioisomers (MQE1, MQE2; FIG. 1B) were not distinguished. Both MQE and QE were stable after one week at 37° C. as assessed by RP-HPLC (data not shown). The properties of MitoG, MQE and QE are summarized in Table 1. It was concluded that MitoG is sufficiently stable for biological experiments involving trapping of glyoxal and methylglyoxal within mitochondria in cells and in vivo, and the reaction products MQE and QE were both robustly stable for chemical isolation and subsequent LC-MS/MS analyses.

TABLE 1

Table 1: Molar extinction coefficients and partition coefficients of MitoG, MQE and QE. Data are means ± SE of 3 determinations.

| | Molar extinction coefficient at wavelength, λ ($M^{-1}$ $cm^{-1}$) | | | | |
|---|---|---|---|---|---|
| Compound | λ = 267 nm | λ = 274 nm | λ = 299 nm | λ = 345 nm | Partition coefficient |
| MitoG | 4069 ± 206 | 3721 ± 193 | 3679 ± 188 | | 2.4 ± 0.1 |
| MQE | 6463 ± 139 | 5509 ± 127 | | 7466 ± 158 | 12.3 ± 0.5 |
| QE | 5275 ± 293 | 4557 ± 245 | | 6901 ± 375 | 13.6 ± 0.9 |

Reactivity of MitoG with Glyoxal and Methylglyoxal

MitoG reacted with methylglyoxal and glyoxal to form products with identical absorption, fluorescence and RP-HPLC properties (FIGS. 3E, F, G & H) to those of independently synthesized and characterized MQE or QE (FIGS. 3B, C & D). Incubation of MitoG with the biologically important and reactive aldehydes 4-hydroxynonenal (HNE) or acrolein followed by RP-HPLC analysis indicated that while MitoG did react, a number of products were formed some of which were unstable (data not shown). Thus the reaction of MitoG with these aldehydes is not diagnostically useful, in contrast to that with 1,2-dicarbonyls, which generates stable, dominant products.

Figure 4:
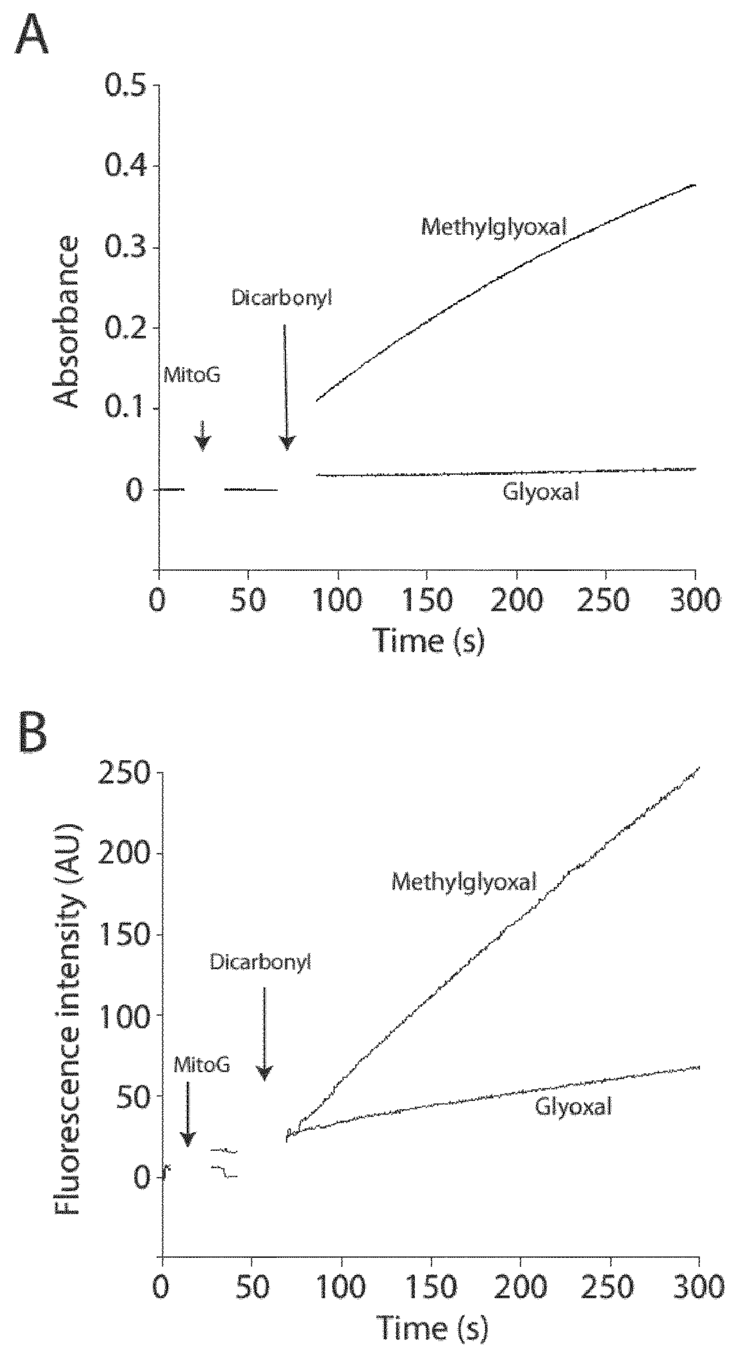
FIG. 4. shows the in vitro reaction of MitoG with methylglyoxal and glyoxal. (A) The reactions between MitoG (100 μM) and 1,2-dicarbonyls (25 μM) at 37° C. were followed from the formation of the quinoxaline products at 345 nm. (B) Fluorimetric detection of the reaction between MitoG and methylglyoxal (40 μM each), and between MitoG and glyoxal (200 μM each) was observed by monitoring the quinoxaline products at excitation and emission wavelengths of 344 and 433 nm, respectively. The changes in fluorescence caused by MQE and QE formation was quantified from calibration curves constructed by plotting fluorescence (excitation and emission wavelengths of 344 and 433 nm, respectively) against known amounts of either quinoxaline and were linear up to at least 20 μM.

Progress of the reaction between MitoG and methylglyoxal could be observed by UV/Vis spectrophotometry, but that of MitoG with glyoxal was too slow (FIG. 4A). However, both reactions could be assessed using a more sensitive fluorometric method (FIG. 4B). The greater reactivity of methylglyoxal over glyoxal with o-phenylenediamines is consistent with the enhanced toxicity of methylglyoxal [46-48]. Aqueous glyoxal exists predominantly as the dihydrate, which is an unreactive tetraol, whereas methylglyoxal is predominantly the monohydrate with only the aldehyde converted into a 1,1-diol. This accounts for the greater reactivity of methylglyoxal, which requires only a single dehydration to generate the highly reactive dicarbonyl [61]. The rate constants for the MitoG-methylglyoxal and the MitoG-glyoxal reactions were: 19±1 $M^{-1}$ $s^{-1}$ and 0.6±0.3 $M^{-1}$ $s^{-1}$ (means±SE, n=3) at 37° C., respectively, compared with the reported value of 1.7±0.3 $M^{-1}$ $s^{-1}$ for the reaction of methylglyoxal with o-phenylenediamine at 25° C. [49]. A competitive rate experiment for methylglyoxal between MitoG and o-phenylenediamine, monitored by $^{1}$H NMR (0.12 mM, DMSO, 25° C.), showed that MitoG was ~1.8× more reactive than o-phenylenediamine, while a similar competition for glyoxal between 4-methoxy-phenylene-1,2-diamine and o-phenylenediamine showed that the 4-methoxy-substitution enhanced reactivity ~3.8-fold. Together these data confirm that MitoG reacts with 1,2-dicarbonyls to form stable diagnostic products and that the electron-donating ether linkage in MitoG enhances the reactivity compared to unsubstituted o-phenylenediamine.

Accumulation of MitoG within Energized Mitochondria

Figure 5:
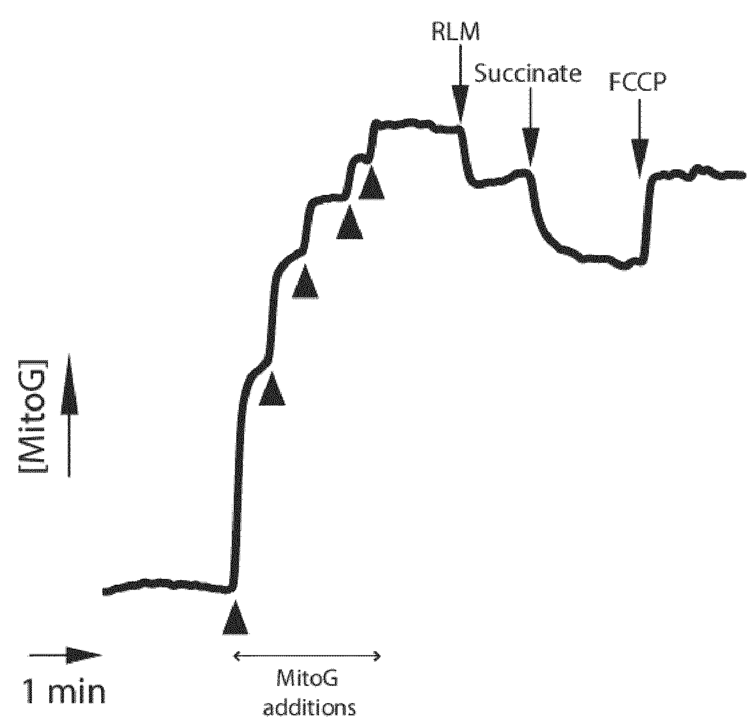
FIG. 5. shows the uptake of MitoG by isolated mitochondria A TPP-selective electrode was placed in a stirred chamber at 37° C. containing 1 ml KCl buffer supplemented with 4 μg/ml rotenone. Following calibration with five additions of 1 μM MitoG (arrowheads) RLM (1 mg protein/ml) were added, followed by 10 mM succinate and 500 nM FCCP (carbonylcyanide p-trifluoromethoxyphenylhydrazone) where indicated. This trace is representative of three independent experiments.

To be a mitochondria-selective probe for 1,2-dicarbonyls in cells and in vivo, the TPP moiety of MitoG should promote its uptake within mitochondria. The uptake of MitoG by isolated mitochondria using an electrode selective for the TPP-moiety of MitoG was measured (FIG. 5). After addition of MitoG to calibrate the electrode response, subsequent addition of mitochondria led to a small decrease in MitoG concentration due to the expected adsorption of MitoG to unenergized mitochondria [38]. Addition of the respiratory substrate, succinate, generated a membrane potential and led to the substantial uptake of MitoG as shown by a decrease in the external concentration. Dissipation of the membrane potential with the uncoupler carbonylcyanide (FCCP) led to the release of MitoG from the mitochondria. The membrane potential-dependent uptake of MitoG into mitochondria was ~2 nmol/mg protein which, assuming a mitochondrial matrix volume of 0.5 μl/mg protein [31], gives a concentration of MitoG within mitochondria of ~4 mM while the external MitoG concentration was ~2 μM. This ~2000-fold accumulation of MitoG indicates that MitoG, like other TPP-conjugated compounds, is selectively accumulated by mitochondria in a membrane potential-dependent manner.

Figure 6:
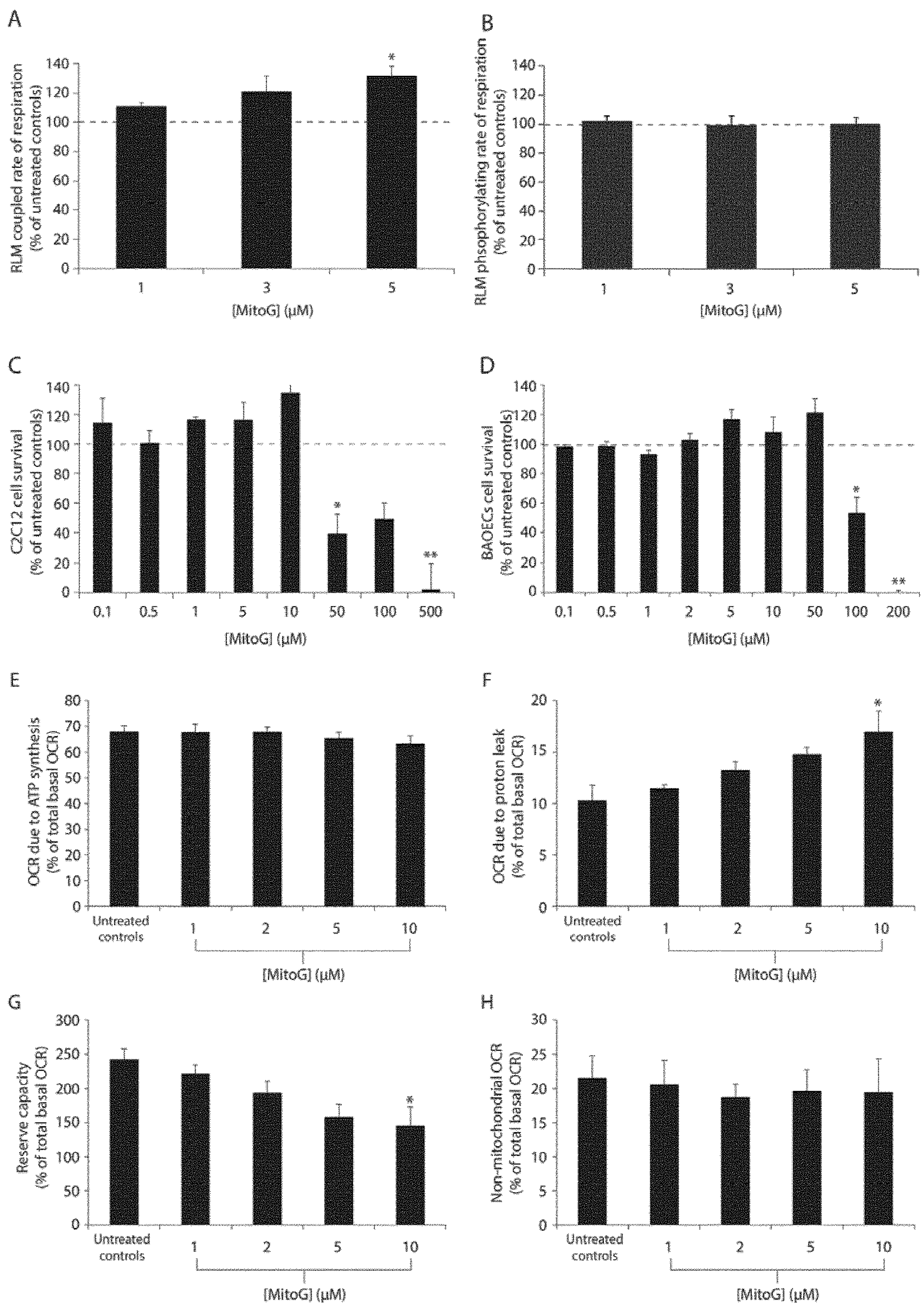
FIG. 6. shows the effects of MitoG on mitochondrial and cell function. (A, B) RLM respiring on glutamate/malate at 37° C. were incubated with various concentrations of MitoG for 7 min in an oxygen electrode to measure coupled respiration (A) before ADP was added to measure phosphorylating respiration (B). Data are the percentage of the respiration rates of untreated controls (dashed lines). (C and D) C2C12 cells (C) or BAECs [Bovine Aortic Endothelial Cells; Cell Applications Inc, San Diego, Calif.] (D) were incubated with MitoG for 24 h and cell survival was then determined using the MTS assay. Data are expressed as a percentage of the untreated controls (dashed line). (E-H) BAECs were incubated with MitoG for 2 h at 37° C. and the cellular oxygen consumption rate (OCR) after the sequential additions of oligomycin, FCCP and antimycin A/rotenone were then measured using a Seahorse XF24 analyser. (E) OCR due to ATP synthesis, (F) OCR due to proton leak, (G) reserve capacity and (H) non-mitochondrial oxygen consumption. Results are means±S.E. of three independent experiments. *, P<0.05 or **, P<0.01 relative to untreated controls.

For MitoG to be useful, it should not disrupt mitochondrial function or cause cell toxicity at the concentrations used. To test this MitoG was incubated with isolated mitochondria and assessed its effect on respiration under different conditions. At 5 μM MitoG there was a slight increase in proton leak as indicated by an increase in coupled respiration (FIG. 6A). This is expected as high levels of TPP cations within biological membranes eventually cause increased proton leak. In contrast, the oxidative phosphorylation complexes themselves were insensitive to MitoG up to 5 μM as there was no effect on phosphorylating respiration (FIG. 6B). MitoG only decreased the viability of C2C12 and BAEC cells at concentrations above 10 and 50 μM, respectively (FIG. 6C, D). To assess the effect of MitoG on mitochondrial function within cells, the oxygen consumption rate (OCR) was measured using a Seahorse XF24 flux analyser (FIG. 6E-H). Concentrations of MitoG above 10 μM slightly decreased OCR due to ATP synthesis and lower concentrations in the range 2-5 μM showed a trend to an increased OCR due to proton leak and a decreased respiratory reserve capacity. Therefore, a MitoG concentration of 2 μM was routinely used for most cell experiments.

Quantification of Reaction of MitoG with 1,2-Dicarbonyls by LC-MS/MS

Figure 7:
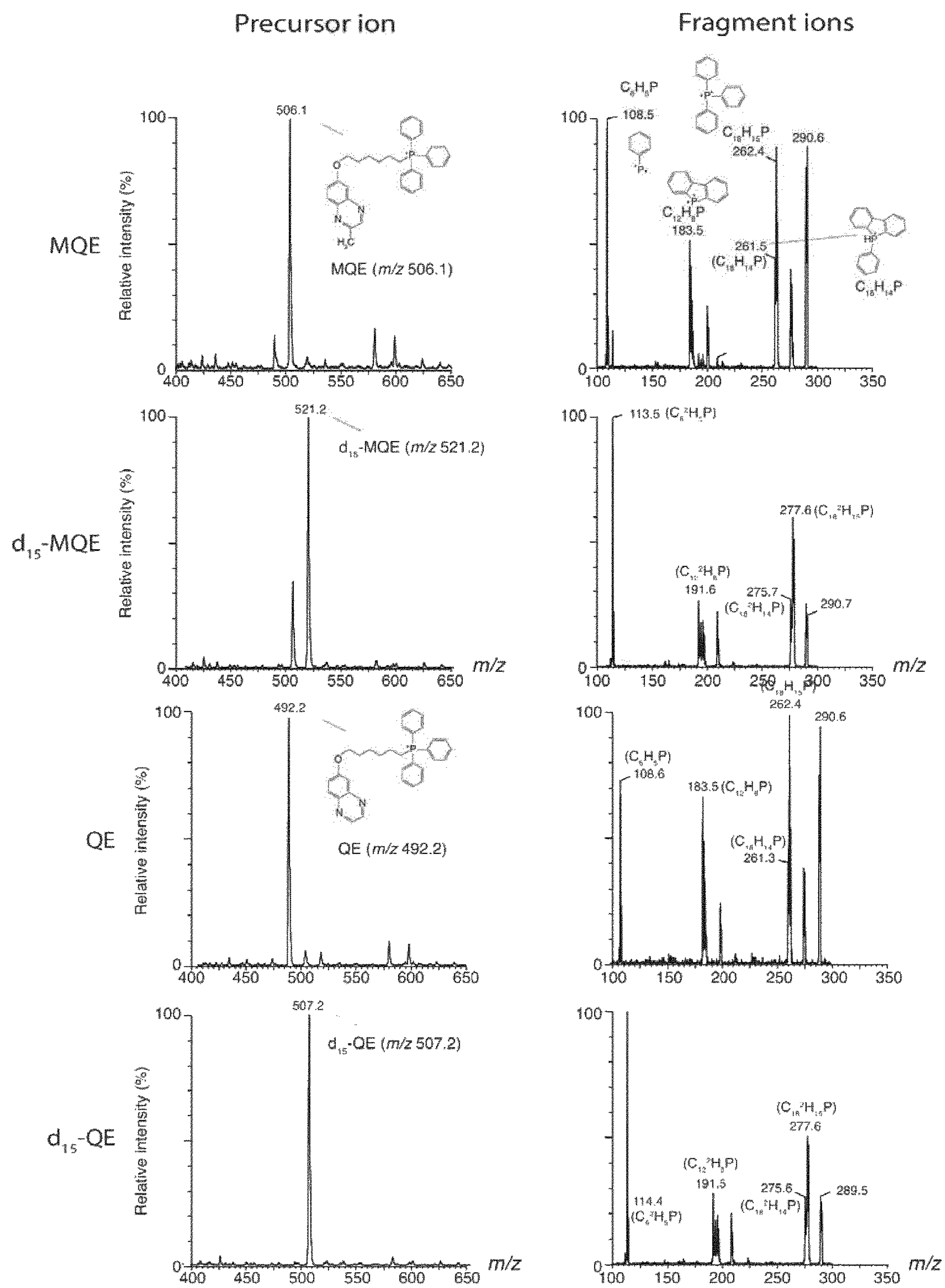
FIG. 7. shows the fragmentation of MQE and QE by tandem mass spectrometry. Compounds (1 μM in 20% acetonitrile) were infused, at 2 μl/min, into a triple quadrupole mass spectrometer. The indicated parent ions of MQE and QE and their corresponding $d_{15}$-variants were fragmented to generate the indicated daughter ions.
Figure 8:
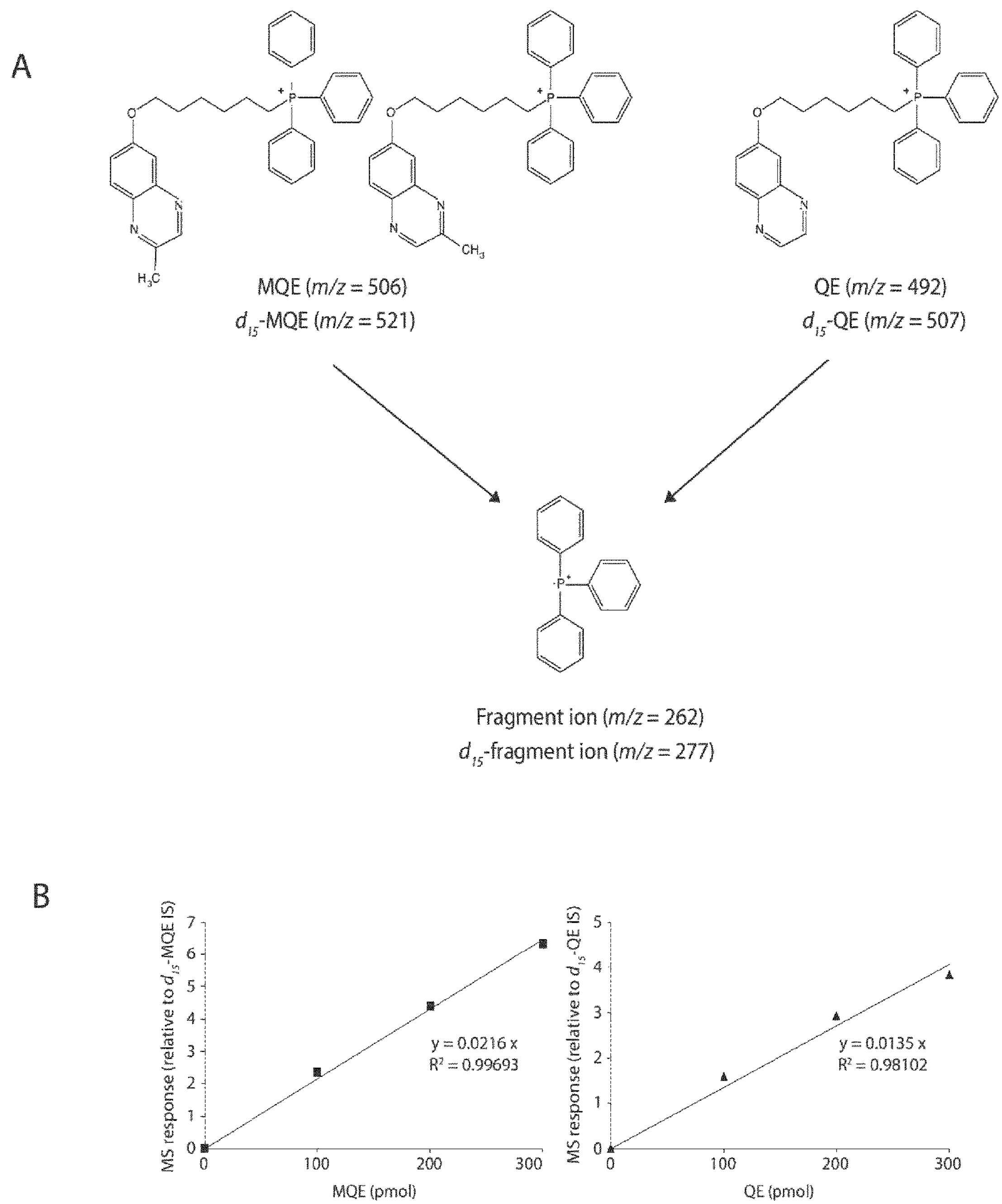
FIG. 8. shows the LC-MS/MS analysis of MQE and QE. (A) QE and both isoforms of MQE have parent ions with distinctive m/z ratios that fragment to form characteristic daughter ions. (B) Standard curves based on the analyses of MQE and QE by LC-MS/MS analysis relative to the corresponding deuterated ISs.

To use MitoG to probe the local concentration of methylglyoxal and glyoxal, it was necessary to measure the amounts of the reaction products (MQE, QE) by LC-MS/MS relative to deuterated internal standards [31]. The fragmentations of MQE and QE and their deuterated versions during tandem MS were determined (FIG. 7), and were as expected for TPP compounds [31]. This fragmentation pattern—to the triphenylphosphorus cation (FIG. 8A)—was used to establish an LC-MS/MS assay for the products of the reaction of MitoG with 1,2-dicarbonyls, and typical standard curves are shown in FIG. 8B. It was concluded that MitoG reaction products can be very sensitively detected, facilitating the use of MitoG to assess mitochondrial methylglyoxal and glyoxal in cells and in vivo.

MitoG as Probe for Mitochondrial Methylglyoxal and Glyoxal in Cells

For MitoG to be an effective probe it should react with methylglyoxal and glyoxal within a biological system to give the diagnostic products, MQE and QE, which can then be extracted and analysed by LC-MS/MS. To assess whether this was possible in cells, BAECs were preincubated with MitoG for 1 h, then methylglyoxal or glyoxal was added and after a further 3 h the cell layers were extracted and analysed by LC-MS/MS to assess the amounts of MQE (FIG. 9A) and QE (FIG. 9B). The levels of both MitoG-derived products, MQE and QE, initially increased with the concentration of exogenous 1,2-dicarbonyls added before showing saturation at supra-physiological 1,2-dicarbonyl concentrations, where MitoG became limiting (FIGS. 9A and B). Treatment with the 1,2-dicarbonyl scavenger, aminoguanidine (AG), or decreasing MitoG mitochondrial uptake using the uncoupler FCCP reduced the amounts of MQE and QE detected (FIGS. 9A and B). As some MitoG is present in the culture medium, there will also be a contribution from MQE/QE formation in the supernatant that is subsequently accumulated by the cells. These findings are consistent with reaction of MitoG with methylglyoxal and glyoxal within cells to form MQE/QE and that this reaction is decreased by AG or by lowering the extent of MitoG uptake into mitochondria within cells by dissipating the membrane potential. It was concluded that MitoG reacts with methylglyoxal or glyoxal in a biological context to form MQE and QE and that these products can be extracted from cells and quantified by LC-MS/MS.

Next MitoG was utilized to determine relative mitochondrial levels of methylglyoxal and glyoxal under hyperglycaemia, a condition in which damaging glycation by 1,2 dicarbonyls is thought to contribute. First it was confirmed that hyperglycaemia did increase the production of cellular methylglyoxal in our system. To do this BAEC cells were incubated under conditions of high (30 mM) and low (5 mM) glucose for 4 h and then measured the formation of methylglyoxal by derivitization with o-phenylenediamine to generate 2-methylquinoxaline, which was assessed by RP-HPLC. This analysis showed that hyperglycaemia in BAEC did indeed increase the formation of methylglyoxal ~2-fold compared to controls (data not shown, n=3). To see whether MitoG could assess a change in mitochondrial methylglyoxal/glyoxal under hyperglycemic conditions the formation of MQE and QE was next compared in cells following incubation with low (5 mM) glucose or high (25 mM) glucose for 4 h (FIGS. 9C & D). There is a gradual increase in the amount of MQE detected over time and this increases substantially on going from low to high glucose, consistent with the increase in methylglyoxal within mitochondria under conditions of hyperglycaemia. This formation of MQE/QE was blocked by the uncoupler FCCP (FIG. 9C,D) and the formation of MQE was also decreased by the methylglyoxal trap AG (FIG. 9E). The increase in MQE upon hyperglycaemia did not occur when the high concentration of D-glucose was replaced with 25 mM of non-physiological L-glucose (along with 5 mM D-glucose to maintain cell viability). This suggests that the increase in MQE caused by a high concentration of D-glucose requires metabolism of the glucose to generate methylglyoxal, and is not due to non-specific effects of a high carbohydrate concentration in the culture medium (FIG. 9E). The reaction between MitoG and methylglyoxal/glyoxal may also occur outside mitochondria, with the subsequent uptake of MQE/QE within mitochondria. However, as the reaction between MitoG and the dicarbonyls is second order the rate of MQE/QE formation within mitochondria is expected to be ~500-1,000-fold greater than in other compartments, even if the methylglyoxal and glyoxal concentrations were the same. Therefore these data are consistent with the formation of MQE/QE occurring primarily within the mitochondria.

When BAECs were incubated under conditions of high glucose in the presence of the glyoxalase I inhibitor bromobenzyl glutathione cyclopentyl diester [35], to suppress degradation of glyoxal and methyl glyoxal, the amount of MQE and QE increased (FIG. 9F). Together these data indicate that MitoG is an effective probe for assessing changes in mitochondrial 1,2-dicarbonyl production within cells. Furthermore, these findings suggest that the mitochondrial methylglyoxal concentration increases ~3-fold under hyperglycemia. Therefore mitochondrial glycation by elevated reactive dicarbonyls is a strong candidate to contribute to the disruption to mitochondrial function that occurs during pathological hyperglycaemia.

MitoG as a Probe for Mitochondrial Levels of Methylglyoxal and Glyoxal In Vivo

Previously it has been shown that the mitochondria-targeted hydrogen peroxide mass spectrometry probe MitoB can be used to assess the production of hydrogen peroxide within mitochondria in living fruit flies [30, 31] and mice [50]. In this, MitoB is acting as a probe to generate the exomarker MitoP [51], that is an exogenous probe compound that when administered to an experimental animal is converted to a diagnostic marker that can be assessed ex vivo and used to infer the production of reactive species within the living organism [51]. Therefore next a study was carried out to see if MitoG could also be used to generate the exomarkers MQE and QE so as to assess the formation of methylglyoxal/glyoxal within mitochondria in vivo. The TPP component of MitoG facilitates this goal, as it is known that following intravenous injection TPP compounds rapidly distribute from the blood to mitochondria within tissues and are then slowly excreted over several hours into the urine and bile [27, 52, 53]. Therefore it may be possible to administer MitoG to mice and then analyze urine to see if there is elevated production of the MQE/QE products under certain conditions, indicating an elevation in reactive dicarbonyls within mitochondria in vivo.

To do this the Akita mouse model ($Ins2^{+/-AkitaJ}$) was used in which a mutation in proinsulin leads to chronic hyperglycaemia and consequent pathological complications similar to those found in type I diabetes. [43-45]. To assess whether there were changes in mitochondrial methylglyoxal/glyoxal in the Akita mice compared to wild type, MitoG (100 nmol) was administered as a tail vein injection and after 4-6 h urine samples were isolated and the MQE and QE contents measured relative to creatinine. These data are shown as a function of blood glucose levels for individual mice (FIGS. 10A & B). As expected, blood glucose was far higher in the Akita mice than in wild type mice, and this increase in blood glucose correlated with a significant increase in both the MQE and QE MitoG adducts, normalized to creatinine (FIGS. 10A & B). These data suggest that MitoG can be used as a probe for the formation of methylglyoxal and glyoxal under conditions of pathologically relevant hyperglycaemia in vivo.

Stability of MitoG

MitoG 100 μM was mixed with 0.07 U horse-radish peroxidase (HRP) in a 1 ml curvette containing 100 mM potassium phosphate buffer (pH 6.0) and 0.5% (w/v) hydrogen peroxide at room temperature. A reference curvette and a blank were similarly set up with DMSO in place of MitoG. Scanning UV/Vis spectra were then taken at 1 min, 5 min and 10 min after mixing using a spectrophotometer (Shimadzu UV-2501PC). Spectra of MitoG-containing mixtures were compared against the spectrum of the blank. To determine if any reaction observed could be prevented by the HRP inhibitor, $NaN_3$ [58, 59] separate incubations were set up as above but containing 8 mg/ml $NaN_3$ as well.

Figure 11:
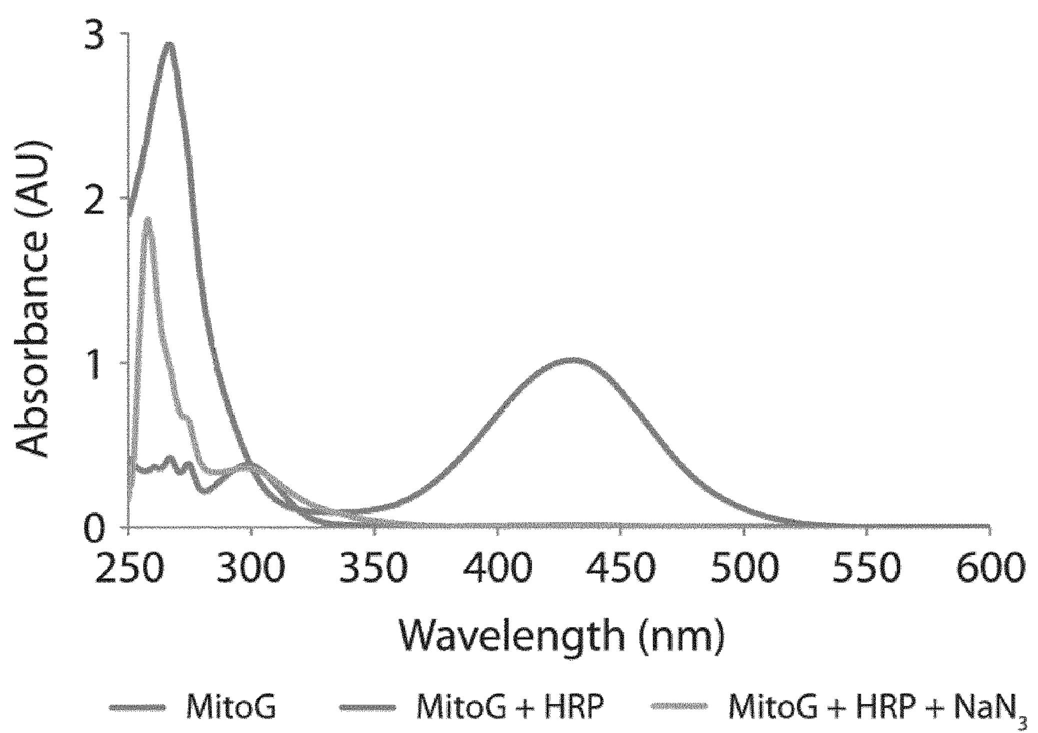
FIG. 11. Shows the stability of MitoG under oxidative conditions.

Oxidative degradation of o-phenylenediamine is known to result in the production of methylglyoxal and glyoxal [60]. This oxidative degradation can lead to an overestimation of dicarbonyl levels in samples if o-phenylenediamine is used to try to quantify methylglyoxal and glyoxal levels in biological samples. To determine if MitoG could undergo similar oxidative degradation to methylglyoxal and glyoxal, MitoG was incubated with HRP and hydrogen peroxide in vitro. Scanning UV/Vis spectra of the reaction mixture were taken before and after the addition of HRP. HRP was used as a representative peroxidase that could catalyse an oxidative degradation in a cellular environment. As shown in FIG. 11, the absorption peak at λ=299 nm due to MitoG disappears after incubation with HRP, while a new peak at λ=430 nm appears. These changes are prevented by the HRP inhibitor, $NaN_3$. These results indicate that MitoG degrades in the presence of HRP to form a product that absorbs at λ=430 nm.

Based upon the differences in the absorption profile (compare FIG. 3B with FIG. 11) this product is neither MQE nor QE which suggests that MitoG does not undergo oxidative degradation to form methylglyoxal and glyoxal. Hence, the reaction of MitoG with peroxidases will not cause the formation of methylglyoxal and glyoxal and, unlike o-phenylenediamine, will not cause artifactual overestimation of mitochondrial dicarbonyl levels in biological samples when MitoG is used as a probe.

Figure 12:
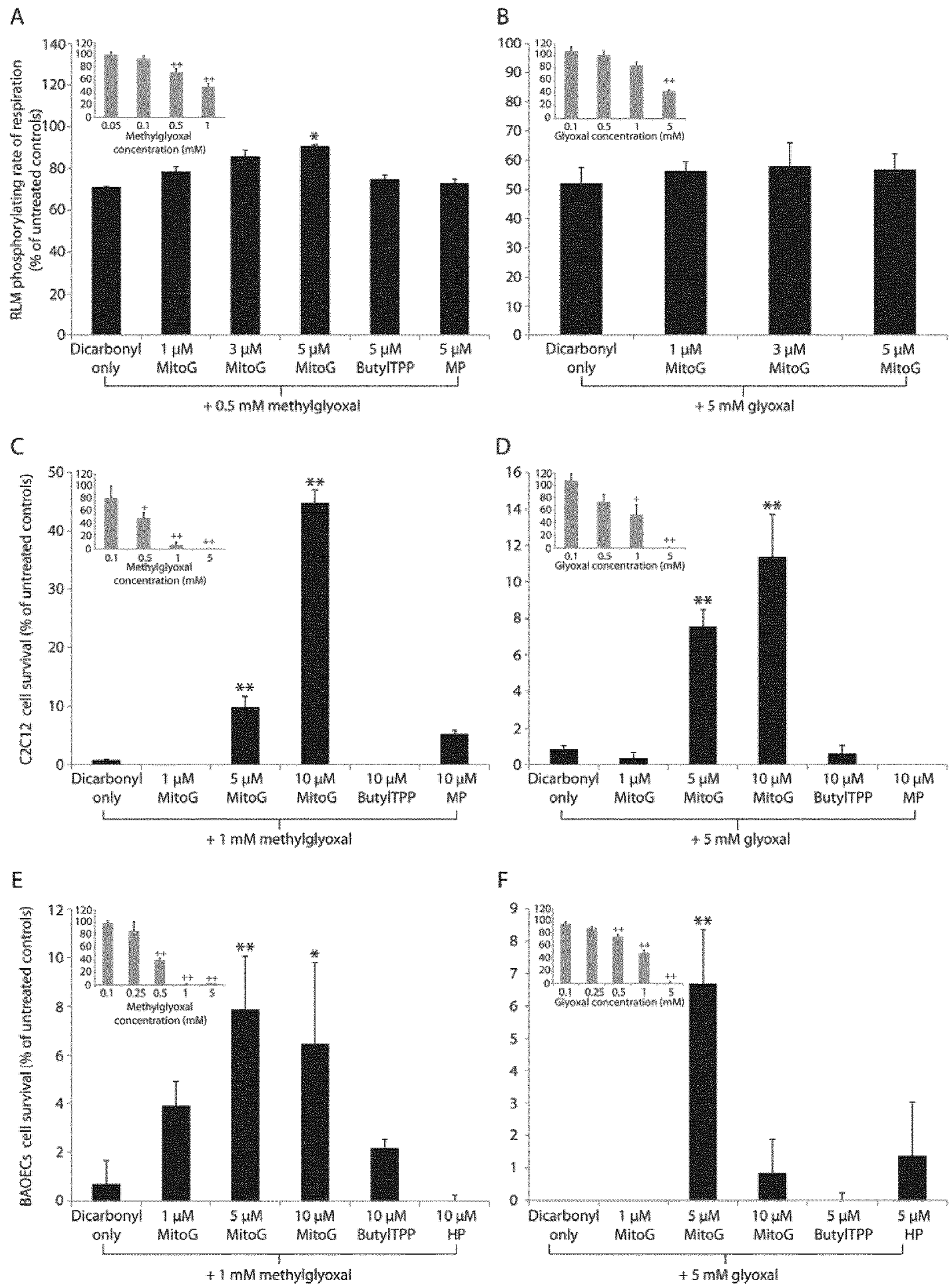
FIG. 12. Shows the protection of MitoG against dicarbony-induced respiratory depression and cell death.

Protection by MitoG Against Dicarbonyl-Induced Respiratory Depression and Cell Death Isolated RLM respiring on glutamate/malate were incubated with MitoG, methoxyphenylenediamine (MP) or butylTPP for 2 min, followed by 0.5 mM methylglyoxal or 5 mM glyoxal for 5 min. ADP was then added and the rate of oxygen consumption monitored at 37° C. (see FIGS. 12A & 12B). C2C12 cells were pre-treated with with MitoG, methoxyphenylenediamine (MP) or butylTPP for 1 h before exposure to 1 mM methylglyoxal or 5 mM glyoxal (see FIGS. 12C & 12D). Following an overnight incubation, cell survival was determined using the MTS assay. Similar experiments were conducted in BAECs pre-treated with MitoG, MP or butylTPP. For all experiments, concentrations of methylglyoxal and glyoxal used were chosen based on results from studies conducted prior to the protection assays. In these prior studies, RLM or cells were exposed to a range of dicarbonyl concentrations, and the phosphorylating rates of respiration or cell survival were evaluated. The results of these earlier experiments are shown in insets, and dicarbonyl concentrations that had caused significant respiratory depression or cell death were chosen for use in the protection assays. Data for all groups were normalized against untreated controls. For RLM, the rate of respiration by untreated controls was taken to be 100%; for cells, cell survival of untreated controls was taken to be 100%. Results are expressed as mean±S.E. of three independent experiments. MitoG was protective against methylglyoxal-induced respiratory depression and both methylglyoxal- and glyoxal-induced cell death in C2C12 cells and BAECs. ButylTPP, MP and HP were not significantly protective in all experiments. In FIG. 12 the symbols *, ** respectively indicate that $P<0.05$ or $P<0.01$ relative to dicarbonyl-only groups; and the symbols +, ++ respectively indicate that $P<0.05$ or $P<0.01$ relative to untreated controls.

To evaluate the usefulness of a mitochondria-targeted approach against glycation-induced toxicity, oxygen consumption by isolated RLM that had been treated with MitoG prior to α,β-dicarbonyl exposure was measured. As shown in FIG. 12A, MitoG protected against methylglyoxal-induced respiratory depression in isolated RLM in a dose-dependent manner, but did not prevent glyoxal damage in this system (FIG. 12B). Analogous experiments were also conducted in cultured cells. C2C12 cells or BAECs were pre-treated with MitoG for 1 h, and then exposed to exogenous methylglyoxal or glyoxal. Cell survival was assessed after an overnight incubation. In these experiments, MitoG was protective against both α,β-dicarbonyls, significantly increasing cell survival in both cell types (FIG. 12C-F). ButylTPP had no significant effect against either dicarbonyl, indicating that the protection observed with MitoG was not due to unspecific effects of the TPP moiety. Equimolar concentrations of the structurally similar but non-targeted compounds, MP and HP, afforded less protection than MitoG, suggesting that specific scavenging of dicarbonyls within mitochondria is a more effective therapeutic strategy than indiscriminate removal of these glycating agents.

Hence, it has been shown that MitoG ameliorates methylglyoxal-induced respiratory depression, and both methylglyoxal- and glyoxal induced cytotoxicity. Non-targeted derivatives of phenylenediamine, MP and HP, were not significantly protective in both isolated mitochondria and cell cultures. Thus, protection by MitoG appears to be related to specific mitochondrial scavenging of these reactive carbonyl species.

Study of the Effects of MitoG-Amide on Diabetic Complications in the Heart

Figures 13, 14:
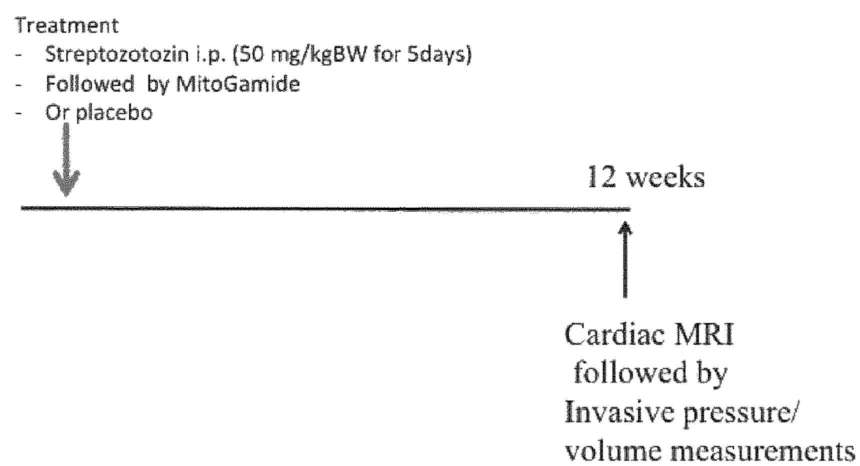
FIG. 13. shows a diagram of the experimental mouse model of diabetes mellitus Type I used for studying the effects of MitoG-amide on diabetic complications in the heart.
FIG. 14. shows a typical magnetic resonance imaging (MRI) image of a mouse heart.
Figure 15:
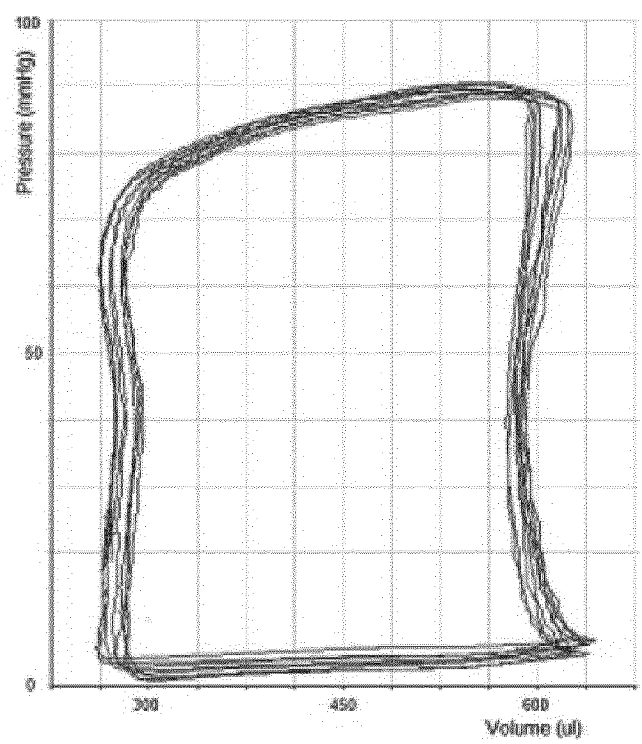
FIG. 15. shows a typical pressure [mmHG]/volume [μl] (P/V) loop measurement of a mouse heart.

To determine the effects of MitoG-amide on diabetic complications in the heart a well-established mouse model of type I diabetes was used, based on destruction of the beta-cells in the pancreas by administration of the beta-cell toxin streptozotocin (STZ; obtainable from Selleck Chemicals, Munich, Germany). Mice that were 6-7 week old C57Bl6/J mice (>20 g) were administered STZ (50 mg/kg by intraperitoneal injection) on 5 consecutive days. The death of the beta-cells and the induction of the high blood glucose associated with Type I diabetes was confirmed by weekly blood glucose tests on mice tail vein blood sample. A blood glucose level >17 mmol/l was considered diabetic. For experiments, mice were divided into three groups: (a) control; (b) STZ-induced Type I diabetes; and (c) STZ-induced Type I diabetic animals treated with MitoG-amide (10 mg/kg body weight once per day via gavage). This was repeated for 12 weeks (FIG. 13). At the end of the protocol, mice underwent cardiac magnetic resonance imaging (MRI) measurement (FIG. 14) followed by left ventricular catheter-based Pressure/Volume (P/V) measurement (FIG. 15). The MRI and P/V loop measurements were performed on the same day and the MRI volume measures were used as correction for the P/V loop.

For the cardiac magnetic resonance imaging (MRI) measurement a standard cardiac MRI protocol with a 4.7T Bruker BioSpec system was performed 24 h after surgery. Anaesthesia was induced with 3% and maintained with 1.25% isoflurane in oxygen. Temperature was monitored with a rectal probe and maintained constant via a heated water blanket, respiration was monitored using a pillow connected to a piezoelectric transducer. Electrocardiogram (ECG) signals were monitored with neonatal graphite (3M) electrodes, placed over the front left and rear right paws.

A 12 cm diameter birdcage was used to transmit the signal and a 4 channel cardiac array coil was used for signal reception. The imaging protocol consisted of scout scans followed by ECG-gated fast imaging with steady state precision (FISP) slices (repetition time/echo time TR/TE 6/2.4 ms 13-20 frames, 3.5 cm field of view (FOV), 256 matrix, 1 mm slice thickness, bandwidth 64.1 kHz, flip angle (FA) 20°, 2 sampling average [number of excitations, NEX]), in the long-axis and in the short-axis to cover the whole heart. In post processing, volumes during different phases of the ECG were delineated and integrated over whole heart using Simpson's rule. Global functional parameters were obtained including ejection fraction, the fraction of blood ejected into the circulation during one heartbeat.

For the Pressure/Volume (P/V) measurement, left ventricular catheterization via the right carotid artery was carried out using a 1.2 F pressure-catheter (Scisense Inc., London, Canada).

Figure 16:
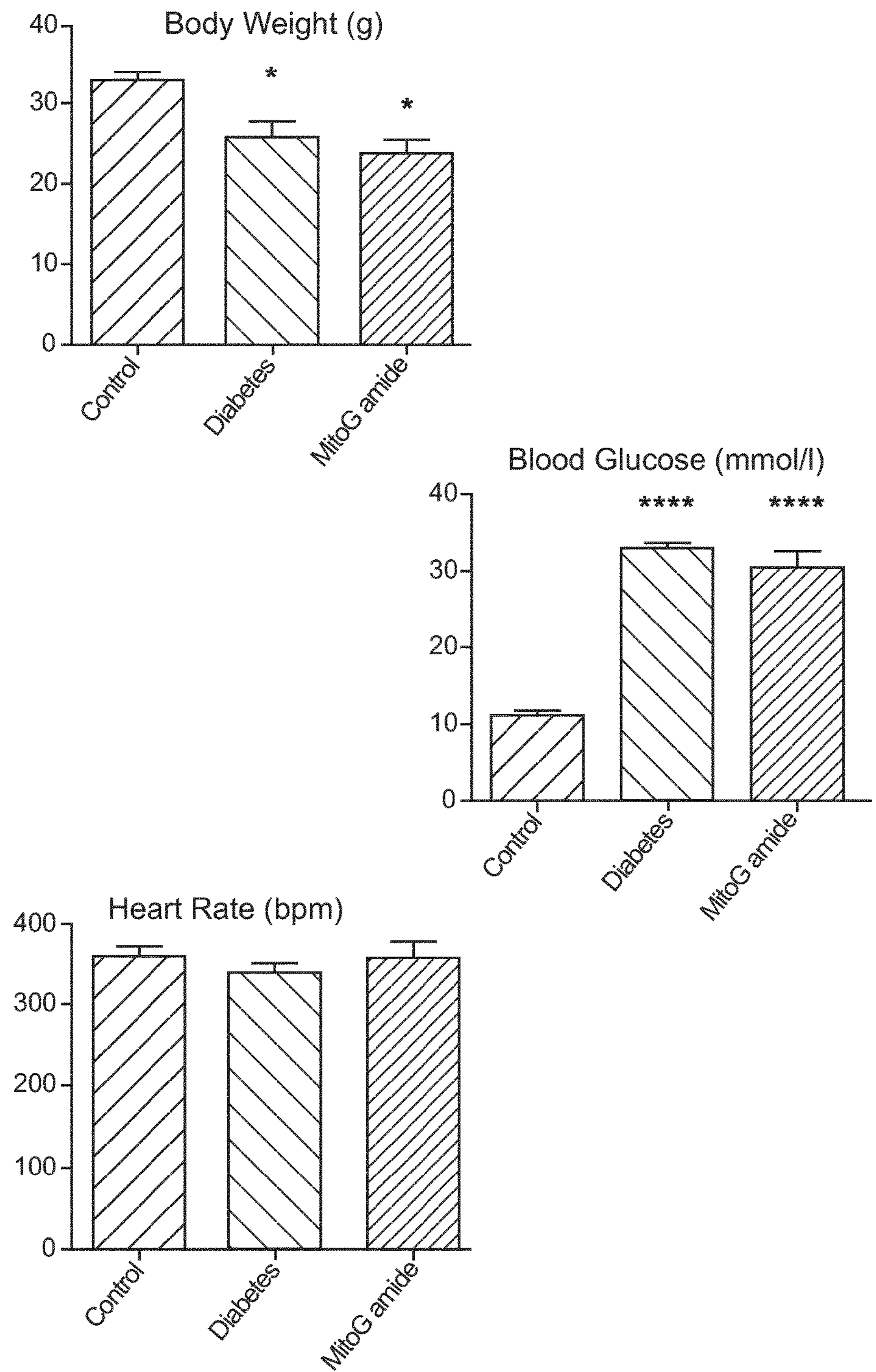
FIG. 16. shows the effect of streptozotocin (STZ) and MitoGamide on body weight, blood glucose and heart rate.

The results of the long-term treatment of the STZ-induced Type I diabetes administered with MitoGamide on body weight, blood glucose and heart rate were compared with placebo-treated STZ mice and controls (FIG. 16). The blood glucose was measured on whole blood using Johnson and Johnson's OneTouch® Ultra Blood Glucose Monitoring System. The heart rate was measured during use of the P/V loop catheter and recorded. This showed that the STZ treatment led to a decrease in body weight and an increase in blood glucose, neither of which were affected by MitoGamide treatment. In addition, neither STZ- or MitoG-amide-treatment affected heart rate in the mice, as was expected.

Study of the Effects of MitoG-Amide on Hyperglycaemia in Type I Diabetes

Figure 17:
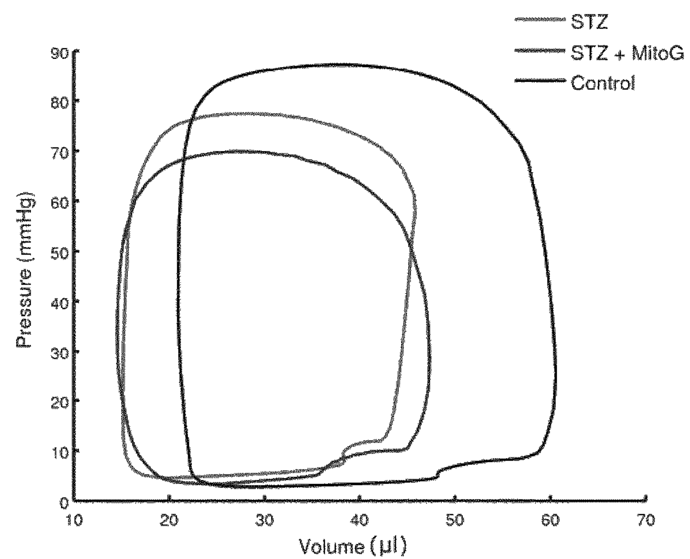
FIG. 17. shows the effect of streptozotocin (STZ)); and STZ and MitoGamide on mean PV-loop results.

To assess the effect of MitoGamide on the well-known detrimental effects of long-term hyperglycaemia in Type I diabetes heart function was measured by MRI and by P/V loop measurement (FIG. 17). Mice that were 6-7 week old C57Bl6/J mice (>20 g) were administered STZ (50 mg/kg by intraperitoneal injection) on 5 consecutive days. The death of the beta-cells and the induction of the high blood glucose associated with Type I diabetes was confirmed by weekly blood glucose tests on mice tail vein blood sample. A blood glucose level >17 mmol/l was considered diabetic. For experiments, mice were divided into three groups: (a) control; (b) STZ-induced Type I diabetes; and (c) STZ-induced Type I diabetic animals treated with MitoG-amide (10 mg/kg body weight once per day via gavage). At the end of the protocol, mice underwent cardiac magnetic resonance imaging (MRI) measurement followed by left ventricular catheter-based Pressure/Volume (P/V) measurement (as described above).

The systolic ejection fraction and the end diastolic volume were measured with MRI according to the procedures given in "Functional assessment of the mouse heart by MRI with a 1-min acquisition", Buonincontri, G.; Methner, C.; Krieg, T.; Carpenter, T. A. and Sawiak, S. J.; *NMR Biomed* (2014), Vol. 27; pages 733-7.

The left ventricular diastolic time constant (Tau Weiss) and the end diastolic pressure were measured from the P/V loop system using a Transonic ADV500 with the corresponding software LifeScribe2.

The diastolic stiffness was measured from the MRI-corrected P/V loops.

Figure 18:
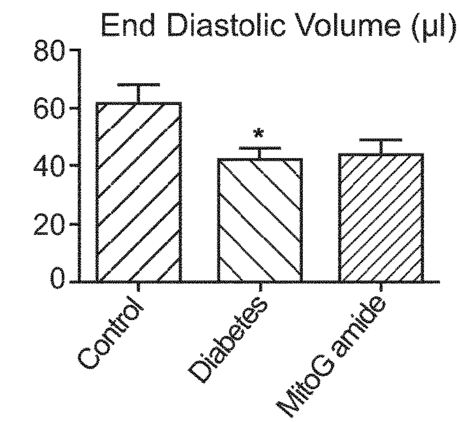
FIG. 18. shows the effect of streptozotocin (STZ); and STZ and MitoGamide on end diastolic volume (μl); ejection fraction (%); left ventricular diastolic time constant (Tau Weiss, ms), diastolic stiffness (1/μl) and end diastolic pressure (mmHg).
Figure 18:
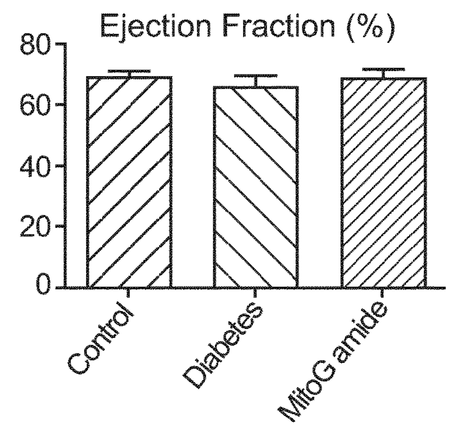
Figure 18:
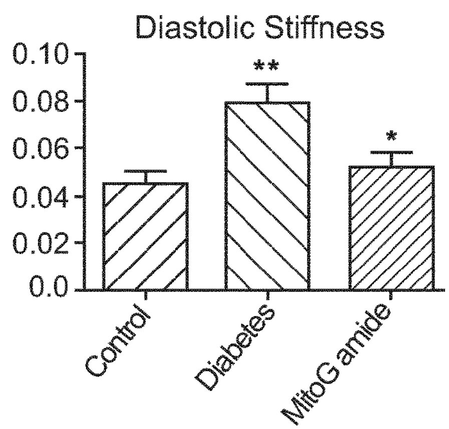
Figure 18:
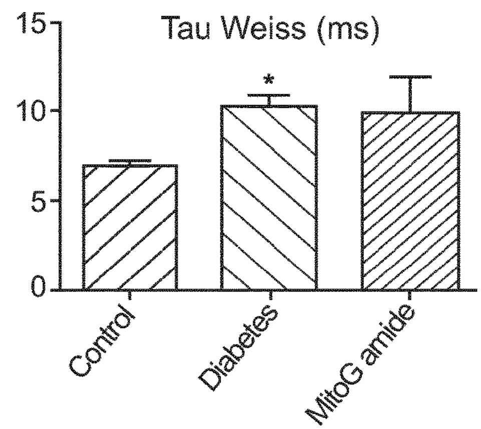
Figure 18:
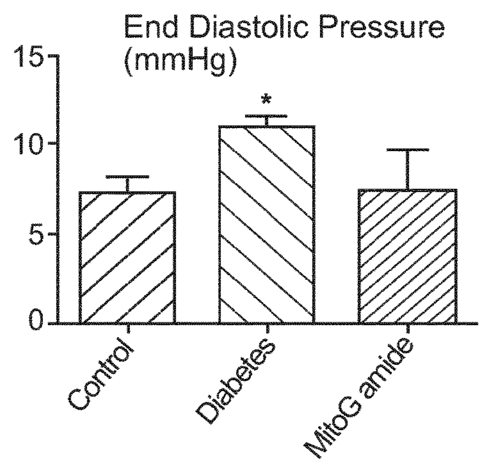

From this it was found that neither STZ nor MitoGamide had any effect on systolic ejection fraction. As expected, STZ treatment impaired end diastolic volume and the left ventricular diastolic time constant (Tau Weiss) but these were not ameliorated by MitoGamide (FIG. 18). However, the expected increase in diastolic stiffness and end diastolic pressure in the diabetic mice were prevented by MitoG-amide (FIG. 18), indicating a protective effect of the compound. MRI volume measures were used as correction for the P/V loop. The MRI-corrected diastolic stiffness is obtained by fitting an exponential to the filling phase, representing the compliance curve in a volume and pressure-dependent manner. The unit is 1/μl. The diastolic stiffness measurements are the most sensitive parameter to indicate early, diabetes-induced myocardial damage and is representative to the changes seen in patients with diabetes.

Finally, at the end of the analysis, hearts were excised and fixed with formalin and processed for histology and then cut into 10 m slices and Optimal Cutting Temperature (OCT) Embedded. To assess oxidative damage to the tissue an antibody against 4-hydroxynonenal, a marker of oxidative damage, (antibody ab48506 HNE-J-2, 1:5 in blocking buffer; obtainable from Abcam plc) was used. These experiments were performed as described in Kaludercic, N.; et al. (2014) "Monoamine oxidase B prompts mitochondrial and cardiac dysfunction in pressure overloaded hearts" *Antioxidants & Redox Signaling*, Vol. 20, pages 267-80, with the exception that 2nd AB Goat anti-mouse (Invitrogen F2761 available from Thermo Fischer Scientific Inc.)+fluorescein (molecular probes, obtainable from Sigma-Aldrich) and 10

M Hoechst stain 33342 (Sigma B2261 obtainable from Sigma-Aldrich) at room temperature was used as the secondary antibody solution.

Figure 19:
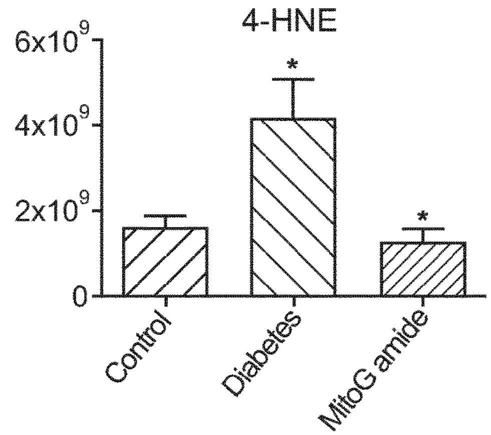
FIG. 19. shows the effect of MitoGamide on the oxidative stress marker 4-hydroxynonenal (4HNE).

The extent of staining was quantified and the data are presented in FIG. 19. These data indicate that MitoGamide decreased oxidative damage in the heart undergoing diabetic complications.

CONCLUSIONS

Disruption to mitochondrial function has been proposed to play a role in pathologies associated with hyperglycaemia. One plausible pathway by which this may occur is through damaging glycation reactions to mitochondrial components by the reactive 1,2-dicarbonyls methylglyoxal and glyoxal. However the importance of this pathway was difficult to assess in cells and in vivo due to the uncertainties about the levels of methylglyoxal and glyoxal that occur within mitochondria during hyperglycemia. To alleviate these problems a mass spectrometry approach has been developed to measure changes in the levels of these reactive 1,2-dicarbonyls within mitochondria in cells and in vivo.

In particular, it has been found that the combination of an o-phenylenediamine with a TPP moiety led to a molecule that accumulated within mitochondria where it reacted with methylglyoxal and glyoxal to form stable products. These products could then be extracted from cells and biological fluids and analyzed by LC/MS/MS relative to stable isotope internal standards. The selectivity of this assessment for methylglyoxal and glyoxal was based on the identification of the products by tandem mass spectrometry, and this was further demonstrated by the changes in their levels on pharmacological inhibition of the glyoxalase system and by addition of the dicarbonyl trap aminoguanidine. The ability of the TPP moiety to locate compounds to mitochondria in cells and in vivo is well established, suggesting that the formation of MQE/QE occurs predominantly due to the reaction with methylglyoxal/glyoxal within the mitochondrial matrix. This is supported by the inhibition of the formation of MQE/QE by addition of the uncoupler FCCP, which decreases the uptake of MitoG into mitochondria. Furthermore, as the reaction between MitoG and methylgloxal/glyoxal is second order, the ~1,000-fold concentration of MitoG within mitochondria will mean that the rate of formation of MQE/QE will be greater inside mitochondria by a similar factor. Thus formation of MQE/QE within a cell or tissue is largely due to changes in the amount of methylglyoxal/glyoxal within mitochondria. However, other reactive species within biological systems such as nitric oxide or reactive aldehydes such as 4-hydroxynonenal may also react with and deplete MitoG, although these reactions will not produce the diagnostic products formed from the reaction with glyoxal/methylglyoxal. Furthermore, while this approach will report on mitochondrial dicarbonyl exposure, it does not indicate the cellular source of the methylglyoxal/glyoxal, and they may be largely produced in the cytosol with subsequent diffusion into mitochondria.

The ability to use MitoG within living mice to generate MQE/QE as exomarkers to assess the changes in dicarbonyls that occurred within a model of type I diabetes was an important step. Hence, this approach will be useful in assessing the role of reactive dicarbonyls in the mitochondrial damage associated with diabetes and in developing specific therapies.

Figure 9:
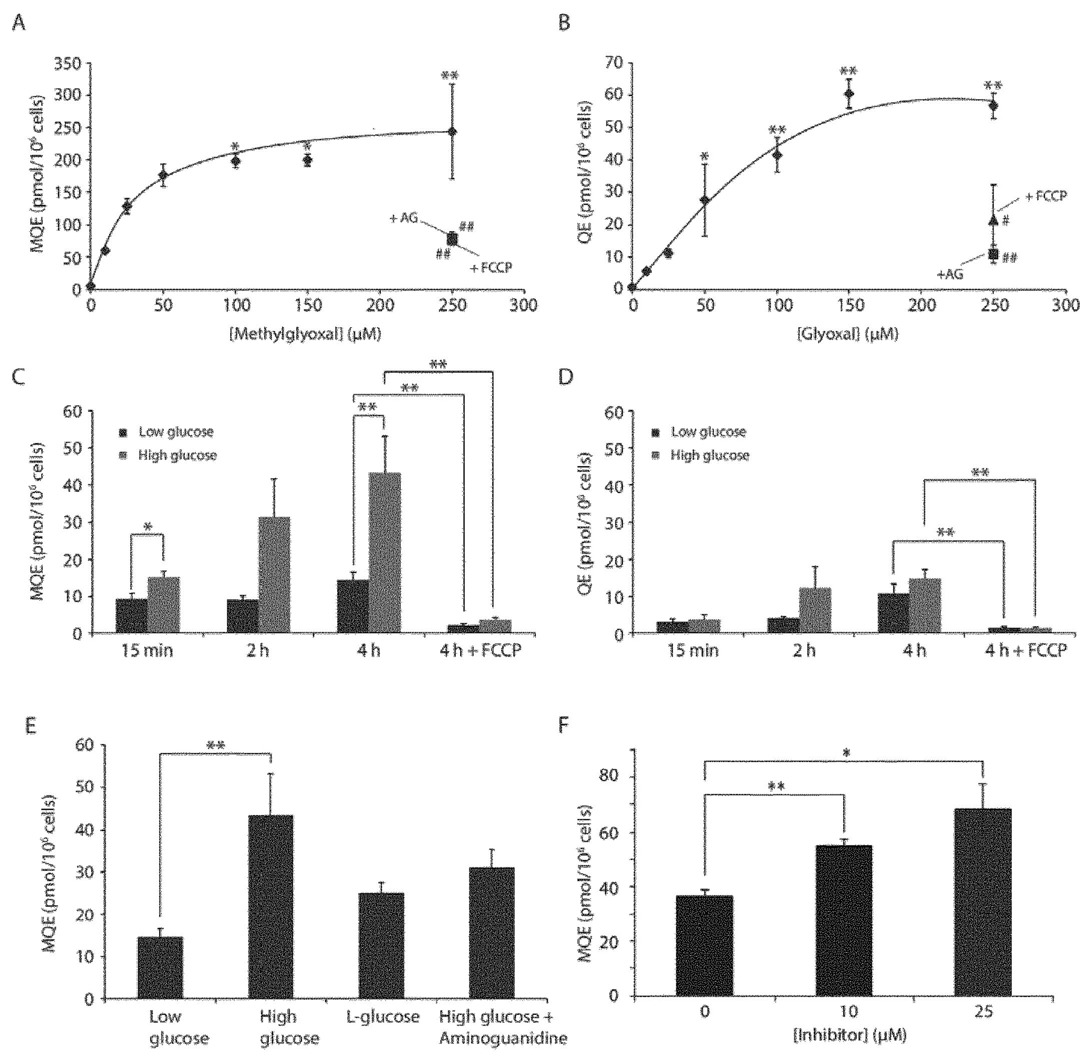
FIG. 9. shows the quantification of MQE and QE in cells. (A) and (B) BAECs were incubated with 2 μM MitoG for 1 h and sometimes supplemented with 10 mM AG or 2 μM FCCP. Methylglyoxal (A) or glyoxal (B) were then added, and after a further 3 h incubation the levels of MQE and QE in the cell layers were determined by LC-MS/MS relative to deuterated ISs. (C, D) BAECs were incubated in media containing low (5 mM) or high (30 mM) D-glucose with 2 μM MitoG for the times indicated. Levels of MQE (C) and QE (D) in the cell layers were determined by LC-MS/MS relative to deuterated ISs. Results are means±S.E. of four independent experiments. (E) BAECs were incubated for 4 h in the presence of 2 μM MitoG in media containing either 5 mM D-glucose (low), 30 mM D-glucose (high), 5 mM D-glucose/25 mM L-glucose (L-glucose), or 30 mM D-glucose/10 mM aminoguanidinium. Levels of MQE in the cell layers were determined by LC-MS/MS relative to deuterated ISs. Levels of MQE in the cell layers were determined by LC-MS/MS relative to deuterated ISs. (F) BAECs were incubated in media containing high (30 mM) D-glucose with 2 μM MitoG for 4 h with the indicated concentrations of the glyoxalase I inhibitor bromobenzyl glutathione cyclopentyl diester. Levels of MQE and QE in the cell layers were then determined by LC-MS/MS relative to deuterated ISs. Results are means±S.E. of three determinations. Results are means±S.E. of three (A, B) or four (C-E) independent experiments. *, P<0.05 or **, P<0.01, relative to untreated (A, B) or indicated (C-E) controls; ##, P<0.01 relative to cells treated with 250 μM 1,2-dicarbonyl.
Figure 10:
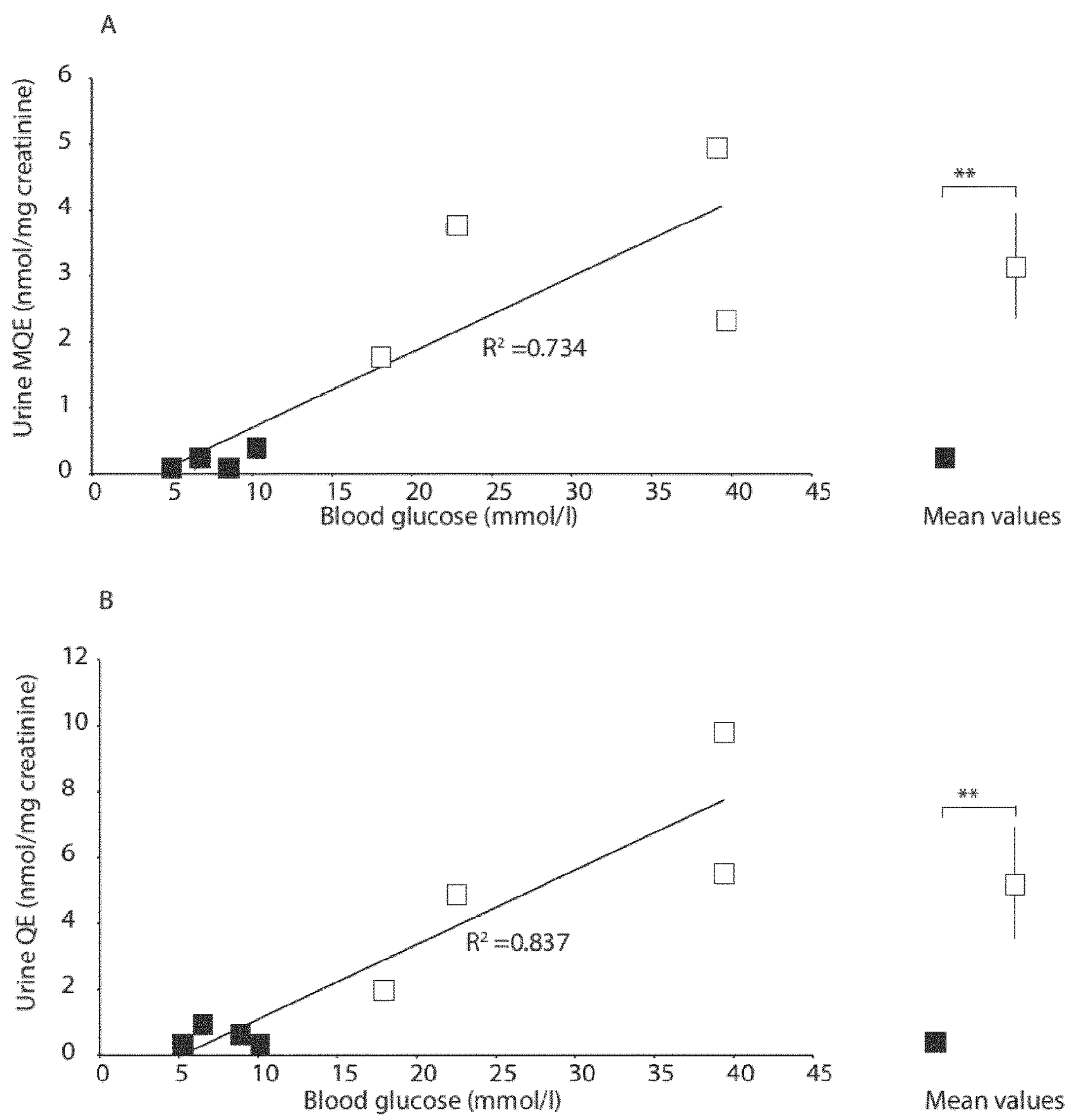
FIG. 10. shows the quantification of mitochondrial dicarbonyls in vivo. The levels of MQE (A) and QE (B) were quantified in urine of wild type and Akita mice relative to creatinine and compared with blood glucose levels of these mice. The data to the right of the plots are the means±S.E. of the two conditions. **, P<0.01.

The findings in FIGS. 9 & 10 show that the formation of MQE and QE from MitoG increased dramatically under conditions of hyperglycaemia in both cells and in vivo indicating that there is a large increase in the amount of methylglyoxal/glyoxal in mitochondria under these conditions. This is consistent with mitochondrial glycation due to the accumulation of methylglyoxal/glyoxal in the matrix contributing to the mitochondrial disruption seen in hyperglycaemia. To conclude, a new mitochondria-targeted mass spectrometric approach has been developed to assess levels of reactive dicarbonyls within mitochondria in cells and in vivo. This will be of use in assessing the contribution of these damaging species to mitochondrial dysfunction in diabetes and aging. Furthermore, compounds have been developed that react with methylglyoxal/glyoxal within mitochondria in cells and in vivo and so act as scavengers for methylglyoxal/glyoxal.

The results shown in FIG. 18 for diastolic stiffness and end diastolic pressure in the diabetic mice indicated that MitoGamide provided a protective effect. Furthermore, the results shown in FIG. 19 indicated that MitoGamide decreased oxidative damage in a heart undergoing diabetic complications.

REFERENCES

[1] Brownlee, M. Negative consequences of glycation. *Metabolism—Clin. Experiment.* 49:9-13; 2000.

[2] Thornalley, P. J. Protein and nucleotide damage by glyoxal and methylglyoxal in physiological systems—role in ageing and disease. *Drug Metabol. Drug Interact.* 23:125-150; 2008.

[3] Pun, P. B.; Murphy, M. P. Pathological significance of mitochondrial glycation. *Int. J. Cell Biol.* 2012:843505; 2012.

[4] Brownlee, M. Biochemistry and molecular cell biology of diabetic complications. *Nature* 414:813-820; 2001.

[5] Rabbani, N.; Thornalley, P. J. Glyoxalase in diabetes, obesity and related disorders. *Semin. Cell Dev. Biol.* 22:309-317; 2011.

[6] Phillips, S. A.; Thornalley, P. J. The Formation of methylglyoxal from triose phosphates—investigation using a specific assay for methylglyoxal. *Eur. J. Biochem.* 212:101-105; 1993.

[7] Casazza, J. P.; Felver, M. E.; Veech, R. L. The metabolism of acetone in rat. *J. Biol. Chem.* 259:231-236; 1984.

[8] Lo, T. W. C.; Westwood, M. E.; Mclellan, A. C.; Selwood, T.; Thornalley, P. J. Binding and modification of proteins by methylglyoxal under physiological conditions—a kinetic and mechanistic study with N-alpha-acetylarginine, N-alpha-acetylcysteine, and N-alpha-acetyllysine, and bovine serum-albumin. *J. Biol. Chem.* 269:32299-32305; 1994.

[9] Chaplen, F. W.; Fahl, W. E.; Cameron, D. C. Evidence of high levels of methylglyoxal in cultured Chinese hamster ovary cells. *Proc. Natl. Acad. Sci. USA* 95:5533-5538; 1998.

[10] Thornalley, P. J.; Battah, S.; Ahmed, N.; Karachalias, N.; Agalou, S.; Babaei-Jadidi, R.; Dawnay, A. Quantitative screening of advanced glycation endproducts in cellular and extracellular proteins by tandem mass spectrometry. *Biochem. J.* 375:581-592; 2003.

[11] Thornalley, P. J.; Waris, S.; Fleming, T.; Santarius, T.; Larkin, S. J.; Winklhofer-Roob, B. M.; Stratton, M. R.; Rabbani, N. Imidazopurinones are markers of physiological genomic damage linked to DNA instability and glyoxalase 1-associated tumour multidrug resistance. *Nucl. Acids Res.* 38:5432-5442; 2010.

[12] Kingkeohoi, S.; Chaplen, F. W. R. Analysis of methylglyoxal metabolism in CHO cells grown in culture. *Cytotechnology* 48:1-13; 2005.

[13] Dhar, A.; Desai, K.; Liu, J. H.; Wu, L. Y. Methylglyoxal, protein binding and biological samples: Are we getting the true measure? *J. Chromatog. B* 877:1093-1100; 2009.

[14] Thornalley, P. J. The glyoxalase system: new developments towards functional characterization of a metabolic pathway fundamental to biological life. *Biochem. J.* 269: 1-11; 1990.

[15] Morcos, M.; Du, X.; Pfisterer, F.; Hutter, H.; Sayed, A. A.; Thornalley, P.; Ahmed, N.; Baynes, J.; Thorpe, S.; Kukudov, G.; Schlotterer, A.; Bozorgmehr, F.; El Baki, R. A.; Stern, D.; Moehrlen, F.; Ibrahim, Y.; Oikonomou, D.; Hamann, A.; Becker, C.; Zeier, M.; Schwenger, V.; Miftari, N.; Humpert, P.; Hammes, H. P.; Buechler, M.; Bierhaus, A.; Brownlee, M.; Nawroth, P. P. Glyoxalase-1 prevents mitochondrial protein modification and enhances lifespan in *Caenorhabditis elegans. Aging Cell* 7:260-269; 2008.

[16] Green, K.; Brand, M. D.; Murphy, M. P. Prevention of mitochondrial oxidative damage as a therapeutic strategy in diabetes. *Diabetes* 53 Suppl 1:S110-118; 2004.

[17] Yoon, Y.; Galloway, C. A.; Jhun, B. S.; Yu, T. Mitochondrial dynamics in diabetes. *Antioxid. Redox Signal.* 14:439-457; 2011.

[18] Newsholme, P.; Gaudel, C.; Krause, M. Mitochondria and diabetes. An intriguing pathogenetic role. *Adv. Exp. Med. Biol.* 942:235-247; 2012.

[19] Baynes, J. W.; Thorpe, S. R. Role of oxidative stress in diabetic complications—A new perspective on an old paradigm. *Diabetes* 48:1-9; 1999.

[20] Rosca, M. G.; Mustata, T. G.; Kinter, M. T.; Ozdemir, A. M.; Kern, T. S.; Szweda, L. I.; Brownlee, M.; Monnier, V. M.; Weiss, M. F. Glycation of mitochondrial proteins from diabetic rat kidney is associated with excess superoxide formation. *Amer. J. Physiol.* 289:F420-F430; 2005.

[21] Ceriello, A.; Ihnat, M. A.; Thorpe, J. E. The "metabolic memory": is more than just tight glucose control necessary to prevent diabetic complications? *J. Clin. Endocrinol. Metab.* 94:410-415; 2009.

[22] Ray, S.; Dutta, S.; Halder, J.; Ray, M. Inhibition of electron flow-through complex I of the mitochondrial respiratory-chain of Ehrlich ascites-carcinoma cells by methylglyoxal. *Biochem. J.* 303:69-72; 1994.

[23] Biswas, S.; Ray, M.; Misra, S.; Dutta, D. P.; Ray, S. Selective inhibition of mitochondrial respiration and glycolysis in human leukaemic leucocytes by methylglyoxal. *Biochem. J.* 323 (Pt 2):343-348; 1997.

[24] Rosca, M. G.; Monnier, V. M.; Szweda, L. I.; Weiss, M. F. Alterations in renal mitochondrial respiration in response to the reactive oxoaldehyde methylglyoxal. *Am. J. Physiol.* 283:F52-59; 2002.

[25] Murphy, M. P. Development oflipophilic cations as therapies for disorders due to mitochondrial dysfunction. *Expert Opin. Biol. Ther.* 1:753-764; 2001.

[26] Smith, R. A.; Hartley, R. C.; Cocheme, H. M.; Murphy, M. P. Mitochondrial pharmacology. *Trends Pharmacol. Sci.* 33:341-352; 2012.

[27] Smith, R. A. J.; Porteous, C. M.; Gane, A. M.; Murphy, M. P. Delivery of bioactive molecules to mitochondria in vivo. *Proc. Natl. Acad. Sci. USA* 100:5407-5412; 2003.

[28] Chaplen, F. W.; Fahl, W. E.; Cameron, D. C. Method for determination of free intracellular and extracellular methylglyoxal in animal cells grown in culture. *Anal. Biochem.* 238:171-178; 1996.

[29] Yamaguchi, M.; Hara, S.; Nakamura, M. Determination of methylglyoxal in mouse blood by liquid chromatography with fluorescence detection *Anal. Chim. Acta* 221: 163-166; 1989.

[30] Cochemé, H. M.; Logan, A.; Prime, T. A.; Abakumova, I.; Quin, C.; McQuaker, S. J.; Patel, J. V.; Fearnley, I. M.; James, A. M.; Porteous, C. M.; Smith, R. A. J.; Hartley, R. C.; Partridge, L.; Murphy, M. P. Using the mitochondria-targeted ratiometric mass spectrometry probe MitoB to measure $H_2O_2$ in living *Drosophila. Nat. Protocols* 7:946-958; 2012.

[31] Cochemé, H. M.; Quin, C.; McQuaker, S. J.; Cabreiro, F.; Logan, A.; Prime, T. A.; Abakumova, I.; Patel, J. V.; Fearnley, I. M.; James, A. M.; Porteous, C. M.; Smith, R. A. J.; Saeed, S.; Carre, J. E.; Singer, M.; Gems, D.; Hartley, R. C.; Partridge, L.; Murphy, M. P. Measurement of $H_2O_2$ within living *Drosophila* during aging using a ratiometric mass spectrometry probe targeted to the mitochondrial matrix. *Cell Metab.* 13:340-350; 2011.

[32] Carrigan, C. N.; Bartlett, R. D.; Esslinger, C. S.; Cybulski, K. A.; Tongcharoensirikul, P.; Bridges, R. J.; Thompson, C. M. Synthesis and in vitro pharmacology of substituted quinoline-2,4-dicarboxylic acids as inhibitors of vesicular glutamate transport. *J. Med. Chem.* 45:2260-2276; 2002.

[33] Fanta, P. E.; Tarbell, D. S. 2-Nitro-4-methoxyaniline. *Organic Synth.* 25:78-80; 1945.

[34] Barton, J. K.; Shao, F.; Elias, B.; Lu, W. Synthesis and characterization of iridium(III) cyclometalated complexes with oligonucleotides: insights into redox reactions with DNA. *Inorg. Chem.* 46:10187-10199; 2007.

[35] Thornalley, P. J.; Edwards, L. G.; Kang, Y.; Wyatt, C.; Davies, N.; Ladan, M. J.; Double, J. Antitumour activity of S-p-bromobenzylglutathione cyclopentyl diester in vitro and in vivo. Inhibition of glyoxalase I and induction of apoptosis. *Biochem. Pharmacol.* 51:1365-1372; 1996.

[36] Twibanire, J. D.; Grindley, T. B. Efficient and controllably selective preparation of esters using uronium-based coupling agents. *Org. Lett.* 13:2988-2991; 2011.

[37] Kelso, G. F.; Porteous, C. M.; Coulter, C. V.; Hughes, G.; Porteous, W. K.; Ledgerwood, E. C.; Smith, R. A. J.; Murphy, M. P. Selective targeting of a redox-active ubiquinone to mitochondria within cells—Antioxidant and antiapoptotic properties. *J. Biol. Chem.* 276:4588-4596; 2001.

[38] Asin-Cayuela, J.; Manas, A. R.; James, A. M.; Smith, R. A.; Murphy, M. P. Fine-tuning the hydrophobicity of a mitochondria-targeted antioxidant. *FEBS Lett.* 571:9-16; 2004.

[39] Choi, S. W.; Gerencser, A. A.; Nicholls, D. G. Bioenergetic analysis of isolated cerebrocortical nerve terminals on a microgram scale: spare respiratory capacity and stochastic mitochondrial failure. *J. Neurochem.* 109:1179-1191; 2009.

[40] Dranka, B. P.; Benavides, G. A.; Diers, A. R.; Giordano, S.; Zelickson, B. R.; Reily, C.; Zou, L.; Chatham, J. C.; Hill, B. G.; Zhang, J.; Landar, A.; Darley-Usmar, V. M. Assessing bioenergetic function in response to oxidative stress by metabolic profiling. *Free Radic. Biol. Med.* 51:1621-1635; 2011.

[41] Hill, B. G.; Benavides, G. A.; Lancaster, J. R., Jr.; Ballinger, S.; Dell'Italia, L.; Jianhua, Z.; Darley-Usmar, V. M. Integration of cellular bioenergetics with mitochondrial quality control and autophagy. *Biol. Chem.* 393: 1485-1512; 2012.

[42] Brand, M. D.; Nicholls, D. G. Assessing mitochondrial dysfunction in cells. *Biochem. J.* 435:297-312; 2011.

[43] Yoshioka, M.; Kayo, T.; Ikeda, T.; Koizumi, A. A novel locus, Mody4, distal to D7Mit189 on chromosome 7 determines early-onset NIDDM in nonobese C57BL/6 (Akita) mutant mice. *Diabetes* 46:887-894; 1997.

[44] Izumi, T.; Yokota-Hashimoto, H.; Zhao, S.; Wang, J.; Halban, P. A.; Takeuchi, T. Dominant negative pathogenesis by mutant proinsulin in the Akita diabetic mouse. *Diabetes* 52:409-416; 2003.

[45] Chacko, B. K.; Reily, C.; Srivastava, A.; Johnson, M. S.; Ye, Y.; Ulasova, E.; Agarwal, A.; Zinn, K. R.; Murphy, M. P.; Kalyanaraman, B.; Darley-Usmar, V. Prevention of diabetic nephropathy in $Ins^{2(+/)(AkitaJ)}$ mice by the mitochondria-targeted therapy MitoQ. Biochem. J. 432:9-19; 2010.

[46] Murata-Kamiya, N.; Kamiya, H. Methylglyoxal, an endogenous aldehyde, crosslinks DNA polymerase and the substrate DNA. *Nucl. Acids Res.* 29:3433-3438; 2001.

[47] Murata-Kamiya, N.; Kamiya, H.; Kaji, H.; Kasai, H. Mutations induced by glyoxal and methylglyoxal in mammalian cells. *Nucl. Acids Symp. Ser:* 3-4; 2000.

[48] Pampati, P. K.; Suravajjala, S.; Dain, J. A. Monitoring nonenzymatic glycation of human immunoglobulin G by methylglyoxal and glyoxal: A spectroscopic study. *Anal. Biochem.* 408:59-63; 2011.

[49] Fedoronko, M.; Konigstein, J.; Linek, K. Determination of dl-glyceraldehyde, dihydroxyacetone and methylglyoxal in a mixture. *J. Electroanalytical Chem. Interfacial Electrochem.* 14:357-367; 1967.

[50] Chouchani, E. T.; Methner, C.; Nadtochiy, S. M.; Logan, A.; Pell, V. R.; Ding, S.; James, A. M.; Cochemé, H. M.; Reinhold, J.; Lilley, K. S.; Partridge, L.; Fearnley, I. M.; Robinson, A. J.; Hartley, R. C.; Smith, R. A. J.; Krieg, T.; Brookes, P. S.; Murphy, M. P. Cardioprotection by S-nitrosation of a cysteine switch on mitochondrial complex I. *Nat. Med.* 19: 753-759; 2013.

[51] Logan, A.; Cochemé, H. M.; Boon Li Pun, P.; Apostolova, N.; Smith, R. A. J.; Larsen, L.; Larsen, D. S.; James, A. M.; Fearnley, I. M.; Rogatti, S.; Prime, T. A.; Finichiu, P.; Dare, A.; Chouchani, E. T.; Pell, V. R.; Methner, C.; Quin, C.; McQuaker, S. J.; Krieg, T.; Hartley, R. C.; Murphy, M. P. Using exomarkers to assess mitochondrial reactive species in vivo. *Biochim. Biophys. Acta* In press; 2013.

[52] Porteous, C. M.; Logan, A.; Evans, C.; Ledgerwood, E. C.; Menon, D. K.; Aigbirhio, F.; Smith, R. A.; Murphy, M. P. Rapid uptake of lipophilic triphenylphosphonium cations by mitochondria in vivo following intravenous injection: implications for mitochondria-specific therapies and probes. *Biochim. Biophys. Acta* 1800:1009-1017; 2010.

[53] Li, Y.; Zhang, H.; Fawcett, J. P.; Tucker, I. G. Effect of cyclosporin A on the pharmacokinetics of mitoquinone (MitoQ10), a mitochondria-targeted antioxidant, in rat. *Asian J. Pharmaceut. Sci.* 5:106-113; 2010.

[54] Beia, M; Afonso, C. A. M.; Martinho, J. M. G.; Synthesis and applications of Rhodamine derivatives as fluorescent probes. *Chem. Soc. Rev.,* 38, 2410-2433, 2009.

[55] Wu C. H.; Yen G. C.; Inhibitory effect of naturally occurring flavonoids on the formation of advanced glycation endproducts. *J Agric Food Chem.,* 53, 3167-73; 2005.

[56] Lo C. T.; Li S.; Tan D.; Pan M. H.; Ho C. T.; Trapping reactions of reactive carbonyl species with tea polyphenols in simulated physiological conditions. *Mol Nutr Food Res.,* 50, 1118-28; 2006.

[57] Tan D.; Wang Y.; Lo C. Y.; Ho C. T.; Methylglyoxal: its presence and potential scavengers.

[58] Brill, A. S.; Weinryb, I.; Reactions of horseradish peroxidase with azide. Evidence for a methionine residue at the active site. *Biochemistry,* 6, 3528-3535; 1967.

[59] Ortiz de Montellano, P. R.; David, S. K.; Ator, M. A.; Tew, D.; Mechanism-based inactivation of orseradish-peroxidase by sodium azide—Formation of meso-azidoprotophorphyrin-IX; *Biochemistry,* 27, 5470-5476; 1988.

[60] Thornalley, P. J.; Protein and nucleotide damage by glyoxal and methylglyoxal in physiological systems—Role in ageing and disease. *Drug Metabol Drug Interact,* 23, 125-150; 2008.

[61] Lo, T. W.; Westwood, M. E.; McLellan, A. C.; Selwood, T.; Thornalley, P. J. Binding and modification of proteins by methylglyoxal under physiological conditions. A kinetic and mechanistic study with N-alpha-acetylarginine, N-alpha-acetylcysteine, and N alpha-acetyllysine, and bovine serum albumin. *J. Biol. Chem.* 269:32299-32305; 1994.

[62] Adachi, K.; Shishido, T.; Hirose, T. Benzotriazole derivatives. *Jpn. Kokai Tokkyo Koho* 1977. Japanese Patent JP 52093771 A 19770806.

[63] Tetraazaannulene cobalt complexes. In: Koho, J. K. T., ed.; 1983.

[64] Chaplen, F. W.; Fahl, W. E.; Cameron, D. C. Method for determination of free intracellular and extracellular methylglyoxal in animal cells grown in culture. *Anal. Biochem.* 238:171-178; 1996.

[65] Katre, N. V.; Knauf, M. J.; Laird, W. J.; Chemical Modification of Recombinant Interleukin 2 by Polyethylene Glycol Increases its Potency in the Murine Meth A Sarcoma Model, *Proc. Natl. Acad. Sci. U.S.A.,* 84: 1487-1491; 1987.

All publications mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

The invention claimed is:

1. A compound of Formula 1:

A-L-B  Formula 1 or a pharmaceutically acceptable salt thereof, wherein:

A is a dicarbonyl sequestering moiety that is a substituted aryl group selected from substituted phenyl, biphenyl and naphthalenyl; or a substituted heteroaryl group selected from substituted pyrrolyl, furanyl, thiophenyl, pyrazolyl, imidazolyl, pyridinyl, pyridazinyl, pyrimidinyl, chromanyl, 2-phenylchromanyl, 3-phenylchromanyl, 4-phenylchromanyl, chromen-4-onyl, 2-phenylchromen-4-onyl, 3-phenylchromen-4-onyl, coumarinyl, 3-phenylcoumarinyl, 4-phenylcoumarinyl and 1,8-bis[2-chromanyl]-6-benzo[7]annuleonyl;

wherein the substituted aryl group, or the substituted heteroaryl group comprises two or more substituent groups independently selected from $—NH_2$, $—NHR_1$, $—NR_1R_1$, $—{}^1X—NH_2$, $—{}^1X—NHR_1$, $—O—NH_2$, $—O—NHR_1$, $—{}^1X—O—NH_2$, $—{}^1X—O—NHR_1$, —NR'—NHR', —$^{1}$X—NR'—NHR', and —NHC(O)$R_1$;

and wherein the substituted aryl group, or the substituted heteroaryl group may optionally comprise one or more optional substituent groups selected from —$C_{1-6}$ alkyl, —$C_{2-6}$ alkenyl, —$C_{2-6}$ alkynyl, -halogen, —$^{1}$X—OH, —$^{1}$X—O—$R_1$, —$CO_2H$, —$^{1}$X—$CO_2H$, —$CO_2R_1$, —$^{1}$X—$CO_2R_1$, —$^{1}$X—O—C(O)—$R_1$, —CH(OH)—C(O)—$R_1$, —$CO_2H$, —$^{1}$X—CH(OH)—C(O)—$R_1$, —CHO, —C(O)—$R_1$, —C(O)$NH_2$, —C(O)$NHR_1$, —$SO_2NH_2$ and —$SO_2NHR_1$; and wherein each $R_1$ is independently selected from —$C_{1-6}$ alkyl, —$C_{2-6}$ alkenyl, —$C_{2-6}$ alkynyl and Formula 2:

Formula 2

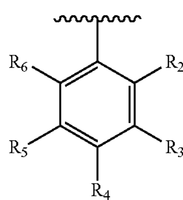

wherein each group $R_2$-$R_4$ is independently selected from —H, —$C_{1-6}$ alkyl, —$C_{2-6}$ alkenyl, —$C_{2-6}$ alkynyl, -halogen, —OH, —$^{1}$X—OH, —O—$C_{1-6}$ alkyl, —$^{1}$X—O—$C_{1-6}$ alkyl, —NR'R', —$^{1}$X—NR'R', —$^{1}$X—NH—$C_{1-6}$ alkyl, —O—$NH_2$, —O—NH—$C_{1-6}$ alkyl, —$^{1}$X—O—$NH_2$, —$^{1}$X—O—NH—$C_{1-6}$ alkyl, —NR'—NHR', —$^{1}$X—NR'—NHR', —NHC(O)—$C_{1-6}$ alkyl, —O—C(O)—$C_{1-6}$ alkyl, —$CO_2H$, —$^{1}$X—$CO_2H$, —$CO_2C_{1-6}$ alkyl, —$^{1}$X—$CO_2C_{1-6}$ alkyl, —$^{1}$X—O—C(O)—$C_{1-6}$ alkyl, —CH(OH)—C(O)—$C_{1-6}$ alkyl, —CHO, —C(O)—$C_{1-6}$ alkyl, —$^{1}$X—CH(OH)—C(O)—$C_{1-6}$ alkyl, —C(O)$NH_2$, —C(O)NH $C_{1-6}$ alkyl, —$SO_2NH_2$ and —$SO_2$NH $C_{1-6}$ alkyl;

each R' is independently selected from —H and —$C_{1-6}$ alkyl; and each $^{1}$X is independently selected from $C_{1-6}$ alkylene, $C_{2-6}$ alkenylene and $C_{2-6}$ alkynylene;

L is a linker moiety of Formula 6:

$$—(Z_1)_m—X_1—(Z_2)_t— \quad \text{Formula 6}$$

wherein:

$Z_1$ and $Z_2$ are independently selected from O, $NR_{12}$, $NR_{12}$-C(O), C(O)$NR_{12}$, O—C(O), C(O)—O and S;

$X_1$ is selected from $C_1$-$C_p$ alkylene, $C_2$-$C_p$ alkenylene, $C_2$-$C_p$ alkynylene and $C_3$-$C_p$ cycloalkylene;

each of m and t is independently selected from 0 or 1;

wherein p=30 and wherein $X_1$ is optionally substituted with one or more functional groups independently selected from the group consisting of hydrogen, alkyl, cycloalkyl, alkenyl, alkynyl, haloalkyl, aryl, aminoalkyl, hydroxyalkyl, alkoxyalkyl, alkylthio, alkylsulfonyl, alkylsulfonyl, carboxyalkyl, cyano, oxy, amino, alkylamino, aminocarbonyl, alkoxycarbonyl, aryloxycarbonyl, alkylaminocarbonyl, arylaminocarbonyl, aralkylaminocarbonyl, alkylcarbonylamino, arylcarbonylamino, aralkylcarbonylamino, alkylcarbonyl, heterocyclocarbonyl, aminosulfonyl, alkylaminosulfonyl, alkylsulfonyl, and heterocyclosulfonyl; and B is a mitochondrial targeting moiety that is a lipophilic cation selected from:

(i) a quaternary phosphonium cation;

(ii) a 1,4a,8-triaza-2,3,4,5,6,7-hexahydro-1H-napthalene compound; and (iii) a Rhodamine compound of Formula 13:

Formula 13

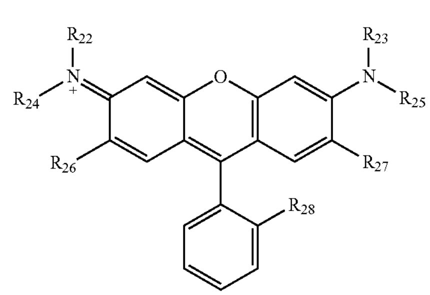

wherein $R_{22}$, $R_{23}$ and $R_{24}$ are independently selected from —H and —$C_1$-$C_6$ alkyl;

$R_{26}$ and $R_{27}$ are independently selected from —H or —$CH_3$;

$R_{28}$ is selected from —$CO_2R_{29}$, —O—C(O)—$R_{29}$, —C(O)—$NHR_{29}$ and —NH—C(O)—$R_{29}$; and one of $R_{25}$ and $R_{29}$ is a bond to the linker L and the other of $R_{25}$ and $R_{28}$ is selected from —H and —$C_1$-$C_6$ alkyl.

2. A compound of Formula 1 or pharmaceutically acceptable salt thereof according to claim 1, wherein A is a substituted aryl group of Formula 3:

Formula 3

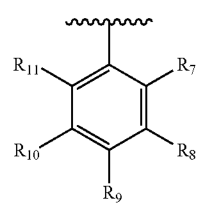

wherein two or more of $R_7$-$R_{11}$ are independently selected from —$NH_2$, —$NHR_1$, —$NR_1R_1$, —$C_{1-6}$ alkylene-$NH_2$, —$C_{1-6}$ alkylene-$NHR_1$, —O—$NH_2$, —O—$NHR_1$, —$C_{1-6}$ alkylene-O—$NH_2$, —$C_{1-6}$ alkylene-O—$NHR_1$, —NHCOR1, —NR'—NHR' and —$C_{1-6}$ alkylene —NR'—NHR'; and the remaining groups $R_7$-$R_{11}$ are independently selected from —H, —$C_{1-6}$ alkyl, —$C_{2-6}$ alkenyl, —$C_{2-6}$ alkynyl, -halogen, —$C_{1-6}$ alkylene-OH, —$C_{1-6}$ alkylene-O—$R_1$, —$CO_2H$, —$C_{1-6}$ alkylene-$CO_2H$, —$CO_2R_1$, —$C_{1-6}$ alkylene-$CO_2R_1$, —$C_{1-6}$ alkylene-O—C(O)—$R_1$, —CH(OH)—C(O)—$R_1$, —$C_{1-6}$ alkylene-CH(OH)—C(O)—$R_1$, —CHO, —C(O)—$R_1$, —C(O)$NH_2$, —C(O)$NHR_1$, —$SO_2NH_2$ and —$SO_2NHR_1$.

3. A compound of Formula 1 or pharmaceutically acceptable salt thereof according to claim 1, wherein B is a mitochondrial targeting moiety of Formula 10:

Formula 10

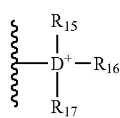

wherein:

D is phosphorous; and each of $R_{15}$, $R_{16}$ and $R_{17}$ is independently selected from substituted or unsubstituted alkyl, benzyl, aryl and heteroaryl.

4. A compound of Formula 1 or pharmaceutically acceptable salt thereof according to claim 1, wherein B is a triphenylphosphonium cation.

5. A compound of Formula 1 or pharmaceutically acceptable salt thereof according to claim 1, wherein the compound is:

(a)

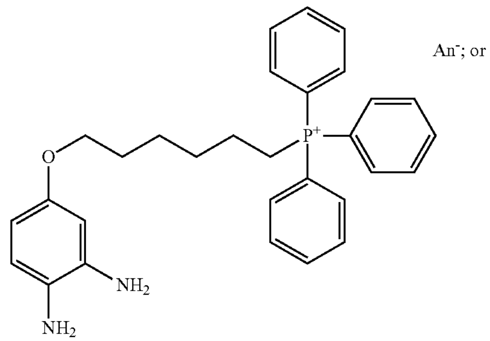

(b)

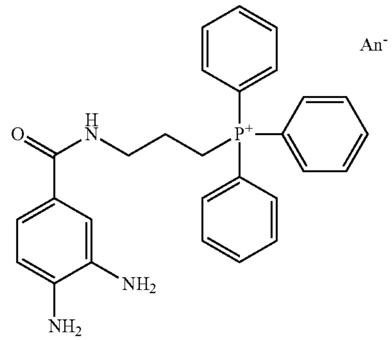

wherein $An^-$ represents an optional pharmaceutically acceptable anion.

6. A compound of Formula 1 or pharmaceutically acceptable salt thereof according to claim 2, wherein $R_7$=—H, $R_{10}$=—H, and $R_{11}$=—H, and $R_8$ and $R_9$ are independently selected from —OH, —$OR_1$, —$NH_2$, —$NHR_1$, —$C_{1-6}$ alkylene-NH2, —$C_{1-6}$ alkylene-$NHR_1$, —O—$NH_2$, —O—$NHR_2$, —$C_{1-6}$ alkylene-O—$NH_2$, —$C_{1-6}$ alkylene-O—$NHR_1$, —$NHCOR_1$ and —O—C(O)—$R_1$.

7. A compound of Formula 1 or pharmaceutically acceptable salt thereof according to claim 1, wherein -L- is a linker moiety of Formula 7:

$$—(Z_1)_m(C_1\text{-}C_p)\text{ alkylene-} \qquad \text{Formula 7.}$$

8. A compound Formula 1 or pharmaceutically acceptable salt thereof according to claim 3, wherein the compound is a salt of Formula 15:

Formula 15

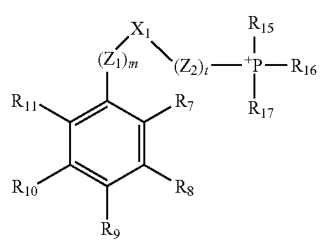

wherein:

each of $R_{15}$, $R_{16}$ and $R_{17}$ is independently selected from substituted or unsubstituted alkyl, benzyl, aryl and heteroaryl; and the compound optionally further includes a pharmaceutically acceptable anion.

9. A compound of formula 1, or a pharmaceutically acceptable salt thereof, according to claim 1, for use in the preservation of organ and tissue for surgical transplants, or in the storage of blood.

10. A compound of Formula 1 or a pharmaceutically acceptable salt thereof according to claim 1, for use as a mass spectrometry probe.

11. A compound of Formula 1 or pharmaceutically acceptable salt thereof according to claim 1, for use as a medicament.

12. A pharmaceutical composition comprising: a compound of Formula 1 or a pharmaceutically acceptable salt thereof according to claim 1, and a pharmaceutically acceptable excipient, carrier or diluent.

13. A method of reversing, alleviating, or inhibiting the progress of a disease or condition in a subject, the method comprising administering to the subject an effective amount of a compound of Formula 1, according to claim 1, or a pharmaceutically acceptable salt thereof, wherein the disease or condition is diabetes.

14. A method according to claim 13, wherein the disease or condition is hyperglycemic diabetes.

15. A method of labelling a biological molecule for mass spectrometry detection comprising contacting said molecule with a compound according to claim 1.

16. A method according to claim 15 wherein said biological molecule comprises a dicarbonyl group.

* * * * *